(12) United States Patent
Han et al.

(10) Patent No.: US 9,944,939 B2
(45) Date of Patent: *Apr. 17, 2018

(54) CSLA9 GLUCO-MANNAN SYNTHASE GENE

(71) Applicant: Board of Trustees of Michigan State University, East Lansing, MI (US)

(72) Inventors: Kyung-Hwan Han, Okemos, MI (US); Won-Chan Kim, Okemos, MI (US); Ida-Barbara Reca, Martina Franca (IT); Kenneth Keegstra, La Valle, WI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 43 days.

This patent is subject to a terminal disclaimer.

(21) Appl. No.: 14/540,320

(22) Filed: Nov. 13, 2014

(65) Prior Publication Data

US 2015/0133651 A1 May 14, 2015

Related U.S. Application Data

(60) Provisional application No. 61/903,709, filed on Nov. 13, 2013.

(51) Int. Cl.
*C12N 15/82* (2006.01)
*C12N 15/67* (2006.01)

(52) U.S. Cl.
CPC ..... *C12N 15/8246* (2013.01); *C12N 15/8217* (2013.01)

(58) Field of Classification Search
None
See application file for complete search history.

(56) References Cited

U.S. PATENT DOCUMENTS

| 7,223,904 B2 | 5/2007 | Heard et al. |
| 8,173,866 B1 * | 5/2012 | Bao ..................... C12N 9/1077 435/320.1 |
| 2010/0107279 A1 | 4/2010 | Ratcliffe et al. |
| 2015/0052641 A1 | 2/2015 | Han et al. |

FOREIGN PATENT DOCUMENTS

| EP | 2410060 A1 | 1/2012 |
| WO | WO-2012103555 A2 | 8/2012 |
| WO | WO-2013130456 A2 | 9/2013 |
| WO | WO-2013130456 A3 | 9/2013 |

OTHER PUBLICATIONS

Ko et al 2009 The Plant Journal 60:649-665, provided in IDS.*
Kim et al 2014 Plant Mol Biol 84:577-587.*
"*Arabidopsis thaliana* MYB transcription factor (At5g12870) mRNA, complete cds", XP002714414,accession No. EM_STD:AY519621 Database accession No. AY519621 sequence, (Feb. 7, 2004).
"International Application Serial No. PCT/US2013/027777, International Preliminary Report on Patentability dated Sep. 12, 2014", 11 pgs.
"International Application Serial No. PCT/US2013/027777, International Search Report dated Feb. 11, 2014", 9 pgs.
"International Application Serial No. PCT/US2013/027777, Invitation to Pay Additional Fees and Partial Search Report dated Nov. 20, 2013", 6 pgs.
"International Application Serial No. PCT/US2013/027777, Written Opinion dated Feb. 11, 2014", 9 pgs.
"PCT Application Serial No. PCT/US2013/027777, Corrected International Search Report dated Mar. 24, 2014", 9 pgs.
Ko, et al., "Ectopic expression of MYB46 identifies transcriptional regulatory genes involve din secondary wall biosynthesis in *Arabidopsis*", The Plant Journal, vol. 60, No. 4, (Nov. 1, 2009), 649-665.
Ko, Jae-Heung, et al., "MYB46-Mediated Transcriptional Regulation of Secondary Wall Biosynthesis", Molecular Plant, vol. 5, No. 5, (Sep. 2012), 961-963.
Zhong, R., et al., "The MYB46 Transcription Factor Is a Direct Target of SND1 and Regulates Secondary Wall Biosynthesis in *Arabidopsis*", The Plant Cell Online, vol. 19, No. 9, (Sep. 1, 2007), 2776-2792.
"U.S. Appl. No. 14/381,040, Non Final Office Action dated Apr. 22, 2016", 6 pgs.
"U.S. Appl. No. 14/381,040, Preliminary Amendment filed Aug. 26, 2014", 3 pgs.
"U.S. Appl. No. 14/381,040, Response filed Mar. 15, 2016 to Restriction Requirement dated Jan. 15, 2016", 6 pgs.
"U.S. Appl. No. 14/381,040, Restriction Requirement dated Jan. 15, 2016", 4 pgs.
"U.S. Appl. No. 14/381,040, Response filed Sep. 22, 2016 to Non Final Office Action Apr. 22, 2016", 8 pgs.
"U.S. Appl. No. 14/381,040, Notice of Allowance dated Jan. 9, 2017", 7 pgs.
"U.S. Appl. No. 14/381,040, Notice of Allowance dated Oct. 5, 2016", 7 pgs.
"U.S. Appl. No. 14/381,040, Response filed Sep. 22, 2016 to Non Final Office Action dated Apr. 22, 2016", 8 pgs.

* cited by examiner

*Primary Examiner* — Brent T Page
(74) *Attorney, Agent, or Firm* — Schwegman Lundberg & Woessner, P.A.

(57) ABSTRACT

The invention relates to plants that contain higher proportions of mannans. Such plants express transcription factors that increase the expression of CSLA9, a mannan synthase.

7 Claims, 12 Drawing Sheets
(3 of 12 Drawing Sheet(s) Filed in Color)

MYB46RE

[A/G][G/T]T[A/T]GGT[G/A]

ProCSLA9

Effector

Reporter

US 9,944,939 B2

CSLA9 GLUCO-MANNAN SYNTHASE GENE

CLAIM OF PRIORITY

This patent application claims the benefit of priority to U.S. Provisional Patent Application Ser. No. 61/903,709, filed Nov. 13, 2013, which is incorporated by reference herein in its entirety.

This invention was made with government support under DE-FC02-07ER64494 awarded by the U.S. Department of Energy. The government has certain rights in the invention.

BACKGROUND

Plant biomass can be a source of fermentable sugar for production of biofuels such as ethanol. A large proportion of plant biomass is cellulose, which is crystallized and densely packed into tight, ordered bundles resistant to water and other solvents. This bundling may help build strong plant cell walls, but strong chemicals, expensive enzymes, and additional energy expenditure is generally needed to break down and separate the bundles and the crystalline cellulose to extract the sugars used to generate biofuels. Incorporation of mannan can alter the structure and assembly of the cellulose so that chemicals and enzymes can break down the cellulose more easily. However, the mechanisms that control mannan synthesis in plant tissues are not understood.

SUMMARY

Plants, plant cell, and plant seeds with heterologous transcription factors such as MYB46, ANAC041 and bZIP1 are described herein. Such plants have increased mannan content when any of these transcription factors are expressed, for example, by transgenic introduction of an expression cassette that has a heterologous promoter operably linked to a nucleic acid segment encoding any of the these transcription factors.

Methods for increasing the mannan content of plant biomass are also described herein that can facilitate recovery of useful products from such plant biomass. For example, increased mannan content can improve recovery of fermentable sugars useful for biofuel production. The methods involve inducing expression of transcription factors such as MYB46, ANAC041 and bZIP1.

For example, one aspect of the invention is an isolated nucleic acid that includes a nucleic acid segment encoding an ANAC041, bZIP1, or MYB46 transcription factor operably linked to a heterologous promoter.

Another aspect of the invention is plant, plant cell or plant seed that includes a nucleic acid segment encoding an ANAC041, bZIP1, or MYB46 transcription factor operably linked to a heterologous promoter.

Another aspect of the invention is a method of generating a transgenic plant that involves recombinantly transforming a plant with a nucleic acid segment encoding an ANAC041, bZIP1, or MYB46 transcription factor operably linked to a heterologous promoter, to thereby generate the transgenic plant.

Another aspect of the invention is a method of increasing expression of CSLA9 enzyme(s) in a plant comprising recombinantly transforming the plant with a nucleic acid segment encoding an ANAC041, bZIP1, or MYB46 transcription factor operably linked to a heterologous promoter, to thereby increase expression of CSLA9 enzyme(s) in the plant.

Another aspect of the invention is a method of generating mannose and/or mannan-containing saccharides comprising: digesting plant biomass comprising a nucleic acid segment encoding an ANAC041, bZIP1, or MYB46 transcription factor operably linked to a heterologous promoter, under conditions sufficient to release mannose sugars and/or mannan-containing oligosaccharides from the plant biomass.

DESCRIPTION OF THE FIGURES

The patent or application file contains at least one drawing executed in color. Copies of this patent or patent application publication with color drawing(s) will be provided by the Office upon request and payment of the necessary fee.

FIG. 1A is an image of electrophoretically separated products from real-time polymerase chain reaction (PCR) quantification of CSLA9, MYB46, and ACT8 mRNA in wild type plants compared to mutant OX#8 and OX#9 plants, which overexpress the MYB46 protein. Total RNAs (500 ng) extracted from 5-week-old stems were used in the RT-PCR (28-31 cycles of amplification). WT, wild-type; OX#8, MYB46 overexpression plant line 8; OX#9, MYB46 overexpression plant line 9. ACT8 (Actin 8) was used as a control. FIG. 1B and FIG. 1C graphically illustrate that the expression levels of CSLA9 are up-regulated by MYB46. Three-week-old wild type and transgenic plants were used. FIG. 1B graphically illustrates over-expression of MYB46 in the transgenic plants as measured by real-time quantitative PCR analysis. FIG. 1C graphically illustrates expression of CSLA9 when MYB46 expression is up-regulated, where expression levels were measured by real-time PCR analysis. The expression of MYB46 and CSLA9 in wild-type plants (WT) was set to 1, and expression in the transgenic plants was relative to wild type expression. Error bars represent the standard deviation of three biological replicates. WT, wild-type; OX#8, MYB46 over-expression line 8; OX#9, MYB46 over-expression line 9;−DEX, inducible MYB46 expression line after 24 h of mock treatment with 0.05% ethanol and 0.02% Silwet surfactant; +DEX, inducible MYB46 expression line after 24 h dexamethasone (DEX) treatment.

FIG. 2A shows the sequence of the MYB46-Responsive cis-Regulatory Element ([A/G][G/T]T[A/T]GGT[G/A], SEQ ID NO:1). FIG. 2B is a schematic diagram of the CslA9 promoter region, showing that the two M46REs are located at nucleotide positions between −640 to −633 and between −1446 to −1439.

FIG. 3A shows binding by GST-MYB46 and GST-MYB83 to the CslA9 −705 to −556 promoter fragment. FIG. 3B shows binding by the GST-ANAC041 to the CslA9 −1312 to −1013 promoter fragment, as well as binding by GST-AtbZIP1 to the CslA9 −762 to −463 promoter fragment. GST-MYB46, GST-MYB83, GST-ANAC041, and GST-AtbZIP1 recombinant proteins were incubated with $^{32}$P-labeled DNA fragments (CslA9 promoter fragments) and then were subjected to polyacrylamide gel electrophoresis. The type of protein added to the $^{32}$P-labeled DNA CslA9 promoter fragment is indicated at the top left of the gel. The GST protein was used as control protein. Competition for the protein-DNA binding was performed using 50× unlabeled probes. The migration position of free unbound DNA probes is indicated by an arrow. FIG. 3C is a schematic diagram of the CSLA9 promoter region, illustrating locations of promoter fragments used in the EMSA assays.

FIG. 4A is a schematic diagram of the vector construct used for inducible expression of the MYB46-GFP protein in *Arabidopsis thaliana* (Col-0) plants. FIG. 4B graphically illustrates enrichment of CslA9 promoter DNA obtained by chromatin immunoprecipitation using a GFP antibody followed by quantitative real-time PCR amplification of the precipitated CslA9 promoter DNA. The values of bound fragments over input fragments of CslA9, C3H14, and MYB54 promoters were normalized against that of the control DNA (MYB46 promoter). C3H14 and MYB54 promoters were used as positive and negative control, respectively. Error bars represent standard deviation of three biological replicates. The symbol * indicates $P<0.01$ by Student's t-test relative to control. FIG. 4C is a schematic diagram of the promoter regions available in the ChIP analysis (the triangles indicate the M46RE location with the numbers identifying nucleotide positions in the promoters; the arrows (→←) indicate primer positions used for real-time PCR).

FIG. 5A graphically illustrates cell-wall mannan content in wild-type plants compared to two plant strains, OX#8 and OX#9, which overexpress MYB46. Mannan content was analyzed in 3-week-old *Arabidopsis* leaves. The mannan content was increased in the MYB46 overexpression lines OX#8 and OX#9. WT indicates wild-type; OX#8 indicates MYB46 overexpression line 8; OX#9 indicates MYB46 overexpression line 9; –DEX indicates inducible MYB46 expression line after 24 h of mock treatment with 0.05% ethanol and 0.02% Silwet surfactant; +DEX indicates inducible MYB46 expression line after 24 h dexamethasone (DEX) treatment. The symbol * indicates $P<0.05$ by Student's t-test relative to control. FIG. 5B shows stem sections from wild type (WT, left two panels), OX#8 (middle two panels), and OX#9 (right two panels) *Arabidopsis* plants after immunofluorescence labeling with antibodies (LM21 and 22) that are specific for mannan (bottom three panels) and cellulose (top three panels). Primary antibody binding was detected using a fluorescent-labeled second antibody (green) as described in Example 1. Cellulose was visualized by staining with Calcofluor white. All images were obtained using the same exposure time. Scale bar=50 mm. FIG. 5C graphically illustrates in vitro mannan synthase activity in microsomes prepared from the leaves of wild-type plants (WT); MYB46 overexpression plant line 8 (OX#8); MYB46 overexpression plant line 9 (OX#9); and boiled wild-type control microsomes (Boiled). The specific activity is shown as pmol GDP-Man incorporation per hour per mg protein. Error bars represent the standard deviation of three biological replicates. Asterisks indicate statistically significant differences relative to the wild-type (Student's t test, $P<0.001$).

FIG. 6A shows schematic diagrams of the reporter and effector constructs used in transient trans-activation assays. The reporter construct consists of GUS reporter gene driven by CSLA9 promoter. The effector constructs contain MYB46, ANAC041 and bZIP1 genes driven by the CaMV35S promoter. FIG. 6B shows GUS expression in tobacco leaves co-transformed with reporter and effector plasmids, as detected by GUS immunostaining Panel 1: CslA9 promoter; Panel 2: MYB46; Panel 3: ANAC041; Panel 4: bZIP1; Panel 5: CslA9 promoter reporter with MYB46 effector; Panel 6: CSlA9 promoter reporter with ANAC041 effector; Panel 7: CSlA9 promoter reporter with AtbZIP1 effector.

DESCRIPTION

Figure 1A:
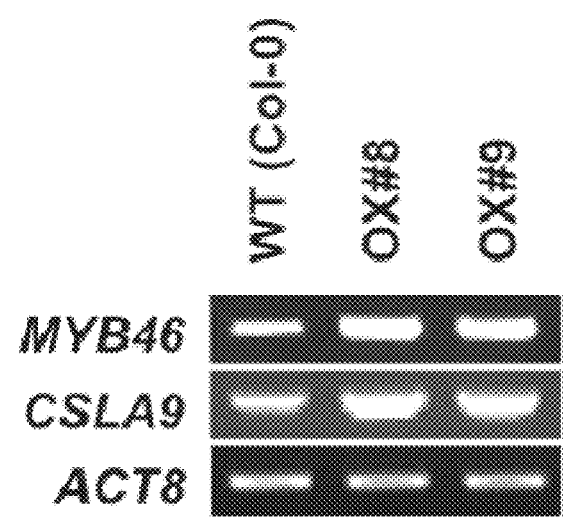
FIG. 1A-1C illustrate that overexpression of the MYB46 protein increases expression of CSLA9.

As described herein, mannan content can be increased in plant tissues by incorporation and expression of transcription factors such as MYB46, ANAC041 and bZIP1 in plant species. Mannans are entirely composed of easily digestible hexoses, and are therefore a preferred source of sugars for biofuel production from plant biomass (Pauly and Keegstra, 2008). These transcription factors can activate expression of the CSLA9 gene in plants, which increases the mannan content of plant tissues.

Hemicelluloses and Mannans

Plant cell walls contain a variety of polysaccharides that constitute the most abundant biomass on Earth. Hemicellulose is the second most abundant component of plant walls, making up to 35% of the wall material (Pauly and Keegstra 2008). Based on compositional and structural differences, hemicelluloses are mostly composed of xylans, xyloglucans, mixed-linkage β-glucans and mannans (Scheller and Ulvskov 2010).

Mannans are hemicellulosic polysaccharides that have a structural role and serve as storage reserves during plant growth and development. Mannan polysaccharides are present in all land plants studied so far. Several types of mannan polymers have been found and classified as mannans, glucomannans, galactomannans and galactoglucomannans (Scheller and Ulvskov 2010). Mannans contain a β-1,4 linked backbone composed of mannose (Man), whereas glucomannans contain a backbone composed of both mannose and glucose (Glc). Substitutions of mannosyl residues of the mannan or glucomannan backbone by single-unit α-1,6 linked galactose (Gal) give rise to galactomannans or galactoglucomannans (Scheller and Ulvskov 2010).

Mannan polysaccharides are functionally distinct. Glucomannan is found in plant secondary cell walls and believed to have a structural role (Meier and Reid, 1982). They are also found as storage carbohydrates in the seeds of some legumes and palms (Buckeridge et al., 2000). Relatively small quantity of galactoglucomannan can be found widely in plant cell walls, but its function is not clear. Oligosaccharides from galactoglucomannan may function as signaling molecules in development as they have been shown to influence in vitro differentiation of tracheary elements in *Zinnia*.

Alkaline conditions can be used to isolate hemicellulose from some forms of plant biomass. For example, alkaline hydrogen peroxide (AHP) extraction for 24 hr extraction at 25° C. or for 2 hr at 60° C. convert most of the hemicellulose in corn fiber to a soluble form (see, e.g., Doner & Hicks, Cereal Chemistry 74(2): 176-181 (1997)). The protocol can include, for example, mixing corn fiber, with NaOH solution, and $H_2O_2$ at a ratio of 1:25:0.25 (w/v/w), followed by incubation at pH 11.5 at 25° C. or 60° C. Alternatively, 25-28% ammonia can be used with incubation at about 120° C. for as little as 20 minutes (see e.g., Kurakake et al., App. Biochem. Biotech. 90: 251 (2001)).

A variety of enzymes can be used to digest hemicellulose and thereby release mannans as free sugars, disaccharides or short oligosaccharides. For example, hemicellulose can be digested under rather mild conditions by use of a variety of enzymes such as β-mannanase, β-xylanase, β-mannosidase, α-galactosidase, β-glucosidase and mixtures thereof. The Mannan endo-1,4-β-mannosidase or 1,4-β-D-mannanase (EC 3.2.1.78), commonly named β-mannanase, is an enzyme that can catalyze random hydrolysis of β-1,4-mannosidic linkages in the main chain of mannans, glucomannans and galactomannans. This enzyme can be used to digest mannans, glucomannans and galactomannans so that the mannan-containing oligosaccharides and sugars can be employed in different industries, including food, feed, pharmaceutical, pulp/paper, and biofuel industries.

Mannose and mannan oligosaccharides can also be released from mannan-containing polysaccharides by treatment of the polysaccharides with 100/100/1 acetic anhydride, acetic acid, and sulfuric acid (v/v) at 40° C. for 12-48 hours, or about 36 hours. See, e.g., Kobayashi et al., Arch Biochem Biophys 245(2): 494-503 (1986).

Control of Cellulose Synthase Expression

Formation of secondary wall requires a coordinated transcriptional activation of the genes involved in the biosynthesis of secondary wall components such as cellulose, hemicellulose and lignin. Recent studies on transcription factors have provided some insight into the complex process of transcriptional regulation of secondary wall biosynthesis (Demura & Ye, *Curr Opin Plant Biol* 13(3):299-304 (2010); Ko et al. *Plant J* 50(6):1035-1048 (2007); Ko et al. *Plant J* 60(4):649-665 (2009); Mitsuda et al., *Plant Cell* 17(11): 2993-3006 (2005); Mitsuda et al., *Plant Cell* 19(1):270-280 (2007); Zhong & Ye, *Curr Opin Plant Biol* 10(6):564-572 (2007); Zhong et al., *Plant Cell* 19(9):2776-2792 (2007); Zhong et al., *Plant Cell* 20(10):2763-2782 (2008); and Zhong et al., *Trends Plant Sci* 15(11):625-632 (2010)).

The cellulose synthase-like A (CSLA) family of enzymes is involved in the synthesis of mannan polysaccharides. Insertion mutants in the *Arabidopsis* csla9 gene exhibited substantially reduced glucomannan, and triple csla2csla3csla9 mutants lacked detectable glucomannan in stems. Overexpression of CSLA2, CSLA7 and CSLA9 increased the glucomannan content in stems. Increased glucomannan synthesis can also lead to defective embryogenesis, with delayed development and occasional embryo death. The embryo lethality of csla7 loss can be complemented by overexpression of CSLA9, suggesting that the glucomannan products are similar. CSLA2, CSLA3 and CSLA9 may be responsible for synthesis of glucomannan in *Arabidopsis* stems, while CSLA7 synthesizes glucomannan in embryos.

Recent studies have indicated that CSLA9, a mannan synthase, is responsible for majority of glucomannan synthesis in both primary and secondary cell walls in inflorescence stems (Dhugga et al. 2004; Liepman et al. 2005; Suzuki et al. 2006; Liepman et al. 2007; Goubet et al. 2009).

The data described herein show that several transcription factors selectively bind to discrete CSLA9 promoters. The transcription factors active in production of CSLA9 include ANAC041, bZIP1 and MYB46, as well as other transcription factors with at least 40%, at least 50%, at least 60%, at least 70%, or at least 75%, or at least 80%, or at least 85%, or at least 90%, or at least 95%, or at least 97% sequence identity to any of SEQ ID NO:3, 5, 7, 9, 11, 13, 15, 17, 19, 21, 23, 24, 25, 27, 29, 31, 33, or 35. In some instances, the transcription factors have at least 40%, at least 50%, at least 60%, at least 70%, at least 75%, or at least 80%, or at least 85%, or at least 90%, or at least 95%, or at least 97% sequence identity to any of SEQ ID NO:3, 17, or 27.

ANAC041 Transcription Factor

The ANAC041 transcription factor binds to the promoter of CslA9. For example, electrophoretic mobility shift assays (EMSA) described herein have confirmed that the ANAC041 factor binds to the CSLA9 promoter (FIG. 3). Transcriptional activation analyses also verify that the ANAC041 protein activates transcription of the CSLA9 gene in vivo (FIG. 6).

Sequences for the ANAC041 transcription factor are available from the National Center for Biotechnology Information (NCBI) database (see, e.g., the website at ncbi.nlm.nih.gov). Genes encoding ANAC041 typically have several introns. Accordingly, a cDNA encoding ANAC041 may conveniently be employed for expression of the ANAC041 protein. For example, one sequence of an ANAC041 (At2g33480) cDNA from *Arabidopsis thaliana*, which is assigned accession number AF325080.1 (GI: 13272418) in the NCBI database, is shown below, and is assigned SEQ ID NO:2 herein.

```
  1  ATGGAGAAGA GGAGCTCTAT TAAAAACAGA GGAGTACTTA
 41  GATTACCACC AGGGTTCCGA TTTCACCCGA CCGATGAAGA
 81  GCTAGTGGTT CAATATTTAC GTCGAAAAGT AACCGGTTTA
121  CCCTTACCAG CTTCTGTAAT ACCGGAAACC GATGTTTGTA
181  AATCCGATCC ATGGGATTTA CCAGGTGATT GTGAATCAGA
201  GATGTATTTT TTTAGCACGA GGGAAGCTAA ATACCCGAAC
241  GGAAACCGGT CGAACCGGTC TACCGGTTCG GGTTATTGGA
281  AAGCGACTGG TCTCGATAAG CAGATCGGTA AGAAGAAGCT
321  TGTCGTGGGG ATGAAGAAAA CTCTTGTTTT CTACAAAGGT
361  AAACCACCAA ACGGAACAAG AACTAACTGG GTTCTTCATG
401  AATATCGTCT TGTTGATTCA CAACAAGATT CATTATATGG
441  ACGGAACAAG AATTGGGTTT TGTGTAGAGT GTTCTTGAAG
481  AAGAGAAGCA ATAGTAATAG TAAGAGGAAA GAAGATGAGA
521  AAGAAGAGGT GGAGAATGAG AAAGAGACAG AGACAGAGAG
561  AGAACGTGAG GAGGAGAACA AGAAGAGTAC TTGTCCCATA
601  TTTTATGACT TTATGAGAAA AGACACGAAG AAAAAGAGAA
641  GGAGAAGAAG ATGCTGTGAT TTGAATTTGA CTCCTGCTAC
681  TTGTTGTTGT TGCTCTTCTT CGACTTCTTC GTCGTCTGTT
721  TGCTCAAGTG CTTTAACTCA CACATCTTCT AATGATAATC
761  GTCAAGAAAT CAGTTATCGG GAAAATAAGT TTTGTTTGTT
801  TCTATAG
```

The SEQ ID NO:2 nucleic acid encodes a protein with NCBI accession number AAK17148.1 (GI:13272419), and the following sequence (SEQ ID NO:3).

```
  1  MEKRSSIKNR GVLRLPPGFR FHPTDEELVV QYLRRKVTGL
 41  PLPASVIPET DVCKSDPWDL PGDCESEMYF FSTREAKYPN
 81  GNRSNRSTGS GYWKATGLDK QIGKKKLVVG MKKTLVFYKG
121  KPPNGTRTNW VLHEYRLVDS QQDSLYGQNM NWVLCRVFLK
161  KRSNSNSKRK EDEKEEVENE KETETERERE EENKKSTCPI
```

```
201  FYDFMRKDTK KKRRRRCCD LNLTPATCCC CSSSTSSSSV

241  CSSALTHTSS NDNRQEISYR ENKFCLFL
```

Nucleic acids and proteins related to the foregoing *Arabidopsis thaliana* ANAC041 are also useful in the methods described herein. For example, a nucleic acid sequence for another ANAC041 transcription factor from *Arabidopsis thaliana* is available as accession number NM_001124963.1 (GI:186505012), and reproduced below as SEQ ID NO:4.

```
   1  TAAAATAAGC CAAACTTTAC CTCTCCATTT TCAATAATCT
  41  CTCATCTTCT TTCGTCTCTC TTTCTACGGT TCAAACATTA
  61  AAAAGATAGA TGGAGAAGAG GAGCTCTATT AAAAACAGAG
 121  GAGTACTTAG ATTACCACCA GGGTTCCGAT TCACCCGAC
 161  CGATGAAGAG CTAGTGGTTC AATATTTACG TCGAAAAGTA
 201  ACCGGTTTAC CCTTACCAGC TTCTGTAATA CCGGAAACCG
 241  ATGTTTGTAA ATCCGATCCA TGGGATTTAC CAGGTGATTG
 281  TGAATCAGAG ATGTATTTTT TTAGCACGAG GGAAGCTAAA
 321  TACCCGAACG GAAACCGGTC GAACCGGTCT ACCGGTTCGG
 361  GTTATTGGAA AGCGACTGGT CTCGATAAGC AGATCGGTAA
 401  GAAGAAGCTT GTCGTGGGGA TGAAGAAAAC TCTTGTTTTC
 441  TACAAGGTA AACCACCAAA CGGAACAAGA ACTAACTGGG
 481  TTCTTCATGA ATATCGTCTT GTTGATTCAC AACAAGATTC
 521  ATTATATAAC ATGAATTGGG TTTTGTGTAG AGTGTTCTTG
 561  AAGAAGAGAA GCAATAGTAA TAGTAAGAGG AAAGAAGATG
 601  AGAAAGAAGA GGTGGAGAAT GAGAAAGAGA CAGAGACAGA
 641  GAGAGAACGT GAGGAGGAGA ACAAGAAGAG TACTTGTCCC
 681  ATATTTATG ACTTTATGAG AAAAGACACG AAGAAAAAGA
 721  GAAGGAGAAG AAGATGCTGT GATTTGAATT TGACTCCTGC
 761  TACTTGTTGT TGTTGCTCTT CTTCGACTTC TTCGTCGTCT
 801  GTTTGCTCAA GTGCTTTAAC TCACACATCT TCTAATGATA
 841  ATCGTCAAGA AATCAGTTAT CGGGAAAATA AGTTTTGTTT
 881  GTTTCTATAG ATTAACAAAC TTGGGAACAA CTTCTATTAA
 921  CTTTAATAAA TTAGATTATG ATTGTTTCCA AAGTTAATTA
 961  TGCAATCCAG GAGTCTTTCT TGGTTTTGGT AATTAATAGC
1001  CATATTTTAT AGCTTATCTA ATTGTATCAA ATATTGAAAA
1041  CTGGT
```

The amino acid sequence of the *Arabidopsis thaliana* ANAC041 polypeptide encoded by the SEQ ID NO:4 nucleic acid has NCBI accession number NP_001118435.1 (GI:186505013), with SEQ ID NO:5 as follows.

```
   1  MEKRSSIKNR GVLRLPPGFR FHPTDEELVV QYLRRKVTGL

61  PLPASVIPET DVCKSDPWDL PGDCESEMYF FSTREAKYPN

61  GNRSNRSTGS GYWKATGLDK QIGKKKLVVG MKKTLVFYKG

121  KPPNGTRTNW VLHEYRLVDS QQDSLYNMNW VLCRVFLKKR

161  SNSNSKRKED EKEEVENEKE TETEREREEE NKKSTCPIFY

201  DFMRKDTKKK RRRRCCDLN LTPATCCCCS SSTSSSSVCS

241  SALTHTSSND NRQEISYREN KFCLFL
```

The SEQ ID NO:5 polypeptide has 99% sequence identity to the SEQ ID NO:3 polypeptide.

Another ANAC041-like factor nucleic acid from *Populus trichocarpa* has NCBI accession number XM_002297824.1 (GI:224053532) encodes a protein with 56% overall sequence identity to the ANAC041 polypeptide with SEQ ID NO:3. The *Populus trichocarpa* ANAC041 (referred to as a NAC domain protein) nucleic acid sequence has the following SEQ ID NO:6 sequence.

```
   1  CACCTCTTTG ATTCCCTCTC TCACCCTTTT CTCCCCTCTT
  41  TACATCTCTT TCCATACTCT AATAATTTAT CTATTGCTCT
  61  CCTTTTCTTC TTCTTCTTGA GGCTCTTTGT CTAATATTCT
 121  CTTTGTGTAA AACTTTAATG GGTTATTACA ACTATAAGAA
 161  GTGTGCATGA GTTTTTAGAC TTTGAGCTAG AATTGCGCAG
 201  CTCCAATAGC TGGTGGAGAC ATTTTTGAGC CACAAGGCAC
 241  ATACATACAC ATACAGTCTT TTTTTGTTCC TTTTGAAGTT
 281  CTTGTGAGGT GCTTTCATAA GGGTATGGAG AAGCTTAGTT
 321  TTGTTAAGAA TGGTGTGCTT AGATTGCCTC CTGGATTTAG
 361  GTTCCACCCA ACAGATGAGG AGCTTGTTGT CCAGTACTTG
 401  AAGAGAAAGG TGTTTGCTTG CCCCTTGCCT GCTTCCATAA
 441  TCCCTGAAGT CGATGTTTGC AAGTCTGATC CTTGGGATTT
 481  GCCAGGTGAT TTGGAGCAAG AACGGTACTT TTTCAGCACC
 521  AGAGAAGCCA AATATCCCAA TGGGAATCGA TCCAACAGAG
 561  CCACAGGCTC TGGCTACTGG AAGGCAACTG GAAAAGAAAA
 601  GCAAATTGTG ACTTCTAAGG GCCACCAAGT TGTGGGGATG
 641  AAGAAAACTC TGGTTTTTTA CAGAGGAAAG CCCCCCCATG
 681  GCACTAGGAC TGATTGGATC ATGCATGAAT ACCGCCTTGC
 721  AAGCACTGAA ACCACAGCCT GCAATACCCT GAAAAGAAAA
 761  AATTCAACTC AGGGCCCTGT TGTGGTGCCA ATGGAAATT
 801  GGGTTCTATG CCGCATATTT TTGAAGAAGA GAGGCACAAA
 841  AAATGAGGAG GAAAACATTC AAGTTGGCAA TGATAATAGA
 881  CTGCCCAAAC TCAGGGCCAC TGAGCCTGTT TTCTATGATT
 921  TCATGACAAA GGAGAAGACA ACTGATTTGA ATCTAGCTCC
 961  TTCCTCTTCA TCCTCAGGAT CCAGTGGAAT CACAGAGGAG
1001  GTGTCCTGTA ATGAATCAGA TGATCACGAA GAGAGTAGTA
1041  GTTGCAATAG TTTTCCTTAC GTTAGAAGAA AACCATAGCT
1081  AGAATGGCCC TCTTAATTAG TCTTTAGTTC TTGTATCCGT
1121  ATTTAGGGGT TCTGGCTTCT CAACCAGAAT AGTCATCTTA
1161  AGCAATCTAA TGCTTGTGTC TTTCGTTTC GTCTCTCTCA
```

```
1201  TCTGTGAGTT CACAAGAAAA GAAAAGAAAA ACAAACCCGG

1241  CATTAACTGT TACCAGTAAT GTAGAGAGGA AGTATGGATG

1281  TCAAGTTGTC ATGTAATCAA AAATTTCAAA GT
```

The amino acid sequence of the *Populus trichocarpa* NAC (ANAC041-like) polypeptide encoded by the SEQ ID NO:6 nucleic acid has NCBI accession number XP_002297860.1 (GI:224053533), with amino acid sequence SEQ ID NO:7 as follows.

```
  1  MEKLSFVKNG VLRLPPGFRF HPTDEELVVQ YLKRKVFACP

41  LPASIIPEVD VCKSDPWDLP GDLEQERYFF STREAKYPNG

81  NRSNRATGSG YWKATGIDKQ IVTSKGHQVV GMKKTLVFYR

121  GKPPHGTRTD WIMHEYRLAS TETTACNTLK NKNSTQGPVV

161  VPMENWVLCR IFLKKRGTKN EEENIQVGND NRLPKLRATE

201  PVFYDFMTKE KTTDLNLAPS SSSSGSSGIT EEVSCNESDD

241  HEESSSCNSF PYVRRKP
```

Another ANAC041-like factor (called NAC5) is available from *Brassica napus*, which is encoded by a nucleic acid with NCBI accession number JF957837.1 (GI:385271602). The protein from *Brassica napus* has 55% overall sequence identity to the ANAC041 polypeptide with SEQ ID NO:5. The NAC5 (ANAC041-like) nucleic acid from *Brassica napus* has the following sequence SEQ ID NO:8.

```
  1  ATGGATAAGG TTAAACTTGT AAAGAATGGT GTTATGAGAT

41  TACCACCTGG ATTCAGATTT CATCCCACTG ATGAGGAACT

61  TGTGGTTCAG TATCTCAAGA GAAAAGTCTT GTCTTCTCCA

121  TTACCAGCTT CCATCATTCC TGACTTTGAT GTTTGCAGAG

161  CTGATCCTTG GGACTTGCCT GGCAATTTGG AGAAGGAGAG

201  GTACTTCTTC AGCACAAGGG AAGCCAAGTA CCCAAATGGG

241  AACCGGTCTA ACCGAGCAAC CGGTTCGGGT TATTGGAAAG

281  CTACCGGTAT TGATAAACGG GTTGTGACCT CTCGAGGAAA

321  TCAAATCGTT GGTTTGAAGA AAACACTCGT TTTCTACAAA

361  GGCAAACCAC CTCATGGCTC AAGAACCGAT TGGATCATGC

401  ATGAATATCG TCTCTCTTCC TCTCCTCCGA GTTCAATGGG

441  TCCTACTCAG AACTGGGTTC TTTGTCGTAT CTTCCTTAAA

481  AAGAGAGCTG GCAGCAAGAG CGACGGCGAC GAGGGAGATA

521  ACCGGAATAT AAGATATGAT AAGGACCACA TTGAAATAAT

561  TACAACAAAC CAAACTGAAG ATAAAACTAA ACCAATCTTC

601  TTCGATTTCA TGAGAAAAGA AAGGACCACA GACTTGAACC

641  TTTTGCCAAG CTCTTCTTCT TCCGACCACG CTTCAAGTGG

681  ACTCACGACG GAGATATTCT CTTCTGATGA AGAGACCAGT

721  AGTTGCAATA GTTTCAGACG AAATCTTTAA
```

The amino acid sequence of the *Brassica napus* ANAC041 polypeptide encoded by the SEQ ID NO:8 nucleic acid has NCBI accession number AFI56995.1 (GI: 385271603), with amino acid sequence SEQ ID NO:9 as follows.

```
  1  MDKVKLVKNG VMRLPPGFRF HPTDEELVVQ YLKRKVLSSP

41  LPASIIPDFD VCRADPWDLP GNLEKERYFF STREAKYPNG

61  NRSNRATGSG YWKATGIDKR VVTSRGNQIV GLKKTLVFYK

121  GKPPHGSRTD WIMHEYRLSS SPPSSMGPTQ NWVLCRIFLK

161  KRAGSKSDGD EGDNRNIRYD NDHIEIITTN QTEDKTKPIF

201  FDFMRKERTT DLNLLPSSSS SDHASSGLTT EIFSSDEETS

241  SCNSFRRNL
```

Another ANAC041-related factor is available from soybean *Glycine max*, which is encoded by a nucleic acid with NCBI accession number NM_001251149.1 (GI: 351724342). The protein from *Glycine max* has 53% overall sequence identity to the ANAC041 polypeptide with SEQ ID NO:5. The ANAC041-related nucleic acid from *Glycine max* is referred to as a NAC14 domain protein, and the nucleic acid that encodes this protein has the following sequence SEQ ID NO:10.

```
  1  CTTTTTCCCT CTCCATACCC TTTTGCTTTC TTTATCCAAT

41  AATAAGAACT TCCCACGAGT GGCTTTAACT GGTCTGGTCT

61  GGTCTGGTCT GGTCGGACAC ACAAAAATAT TAGTATGGAG

121  AAGGTGAGTT TTGTGAAGAA TGGAGAGCTT AGATTGCCTC

161  CGGGGTTTCG TTTCCACCCG ACTGATGAGG AGCTGGTTTT

201  GCAGTACTTG AAGCGCAAGG TCTTCTCCTG CCCTCTGCCA

241  GCCTCTATCA TTCCTGAGGT TGATGTTTGC AAGTCTGATC

281  CTTGGGATTT GCCAGGTGAT TTGGAGCAAG AGAGATACTT

321  CTTTAGCACC AAAGAGGCCA AATATCCCAA CGGAAATCGC

361  TCTAACAGAG CCACAAATTC GGGTTATTGG AAGGCAACTG

401  GCTTGGACAA ACAAATTGTT ACTTCAAAAG GGAACCAAGT

441  TGTGGGGATG AAGAAGACAC TTGTTTTCTA CAGAGGCAAG

481  CCTCCTCATG GATCCAGAAC TGATTGGATC ATGCATGAGT

521  ATCGCCTCAA CATCCTTAAC GCCTCTCAGA GCCATGTTCC

561  CATGGAAAAT TGGGTTCTAT GTCGCATATT TTTGAAGAAG

601  AGAAGCGGTG CTAAAAATGG GGAGGAGAGC AACAAGGTGA

641  GGAACTCTAA GGTGGTTTTC TATGACTTCC TAGCGCAGAA

681  CAAGACTGAT TCCTCATCCT CGGCCGCCAG TGGAATTACA

721  CATGAACATG AATCAGATGA ACATGACCAT GAAGAGAGCA

761  GTAGCTCCAA CACCTTCCCT TATACTATTA GAACGAAACC

801  TTAACAACCA AGTCAACAAC CACCTTCCTT AAAAAGTTGA

841  TTATCACCTA GTTTTTTTTT TTTTAATTCT CTTTCCCTTT

881  CCCTGTAATC ATCAACAACC ACTTGTTGAA AGGAAGCATC

921  CCTCCCAATG AGACCGGCAT TAGTTAAAGG GTAGCCTGCA

961  GAGTATGGTA CTGATAGTAG CAGTGTGTAA TGGACTCCCC
```

-continued

```
1001 ATTTTCCTTC AATTTAACCT TTTTTTCTAA TGCCCATGCT

1021 TCTTCTTTTA AAAAAAAAAA AAAAAAA
```

The amino acid sequence of the *Glycine max* ANAC041-related polypeptide encoded by the SEQ ID NO:10 nucleic acid has NCBI accession number NP_001238078.1 (GI: 351724343), with amino acid sequence SEQ ID NO:11 as follows.

```
  1 MEKVSFVKNG ELRLPPGFRF HPTDEELVLQ YLKRKVFSCP

41 LPASIIPEVD VCKSDPWDLP GDLEQERYFF STKEAKYPNG

61 NRSNRATNSG YWKATGLDKQ IVTSKGNQVV GMKKTLVFYR

121 GKPPHGSRTD WIMHEYRLNI LNASQSHVPM ENWVLCRIFL

161 KKRSGAKNGE ESNKVRNSKV VFYDFLAQNK TDSSSSAASG

201 ITHEHESDEH DHEESSSSNT FPYTIRTKP
```

Another ANAC041-related factor is available from soybean *Glycine max*, which is encoded by a nucleic acid with NCBI accession number NM_001251701.1 (GI: 351725494). The protein from *Glycine max* has 59% overall sequence identity to the ANAC041 polypeptide with SEQ ID NO:5. The ANAC041-related nucleic acid from *Glycine max* is referred to as NAC15 and has the following nucleic acid sequence with SEQ ID NO:12.

```
  1 ACACAAAAAT ATTATTAGCA TGGACAAGGT GAATTTTGTG

41 AAGAATGGAG AGCTTAGATT GCCTCCGGGG TTCCGTTTCC

81 ACCCGACTGA TGAGGAGCTG GTTCTGCAAT ACTTGAAGCG

121 CAAGGTCTTC TCCTGCCCTT TGCCAGCCTC TATCATTCCT

161 GAGCTTCATG TTTGCAAGTC TGATCCTTGG GATTTGCCAG

201 GTGATTTGGA GCAAGAGAGA TACTTCTTTA GCACCAAAGT

241 GGCCAAATAT CCCAACGGAA ATCGCTCCAA CAGAGCCACA

281 AATTCGGGTT ATTGGAAGGC AACTGGCTTG ACAAACAAA

321 TTGTTACTTC AAAAGGCAAC AACCAAGTTG TCGGAATGAA

361 GAAGACACTT GTTTTCTACA GAGGCAAGCC TCCTAATGGA

401 TCCAGAACTG ATTGGATCAT GCACGAGTAT CGCCTCATCC

421 TTAACGCCTC TCAGTCTCAG AGCCATGTTG TTCCCATGGA

481 AAATTGGGTT CTGTGTCGCA TATTTTGAA GAGGAGAATT

521 GGTGCTAAAA ATGGGGAGGA GAGCAACTCT AAGGTGGTTT

561 TCTATGACTT CTTAGCGCAG AACAAGACCG ATTCCTCCTC

601 ATCGGTCGCC AGTGGAATTA CACATGAATC AGATGAACAT

641 GAAGAGAGCA GTAGCTCCAA CACCTTCCCT TATACTATTA

681 GAAGAAACC TTAACAACCT TCCTTAAAAA TTTAAGTTCA

721 TTATCTAGTT GTTGTTTTTA ATTGTCTTTC CCTTTCCCTG

761 TAATTATCAT CAATCACTTG TTGAAAGGAA GCATCCTCTT

801 CCCAAATGAG ACCGGCATTA AGGGTAGTCT GGAGAGTATG

841 GTACTAATAC TAGTAGTAGT GTGTAATACA
```

The amino acid sequence of the *Glycine max* ANAC041-related polypeptide encoded by the SEQ ID NO:12 nucleic acid has NCBI accession number NP_001238630.1 GI:351725495), with amino acid sequence SEQ ID NO:13 as follows.

```
  1 MDKVNFVKNG ELRLPPGFRF HPTDEELVLQ YLKRKVFSCP

41 LPASIIPELH VCKSDPWDLP GDLEQERYFF STKVAKYPNG

61 NRSNRATNSG YWKATGLDKQ IVTSKGNNQV VGMKKTLVFY

121 RGKPPNGSRT DWIMHEYRLI LNASQSQSHV VPMENWVLCR

161 IFLKRRIGAK NGEESNSKVV FYDFLAQNKT DSSSSVASGI

201 THESDEHEES SSSNTFPYTI RRKP
```

Another ANAC041-related factor is available from sunflower *Helianthus annuus*, which is encoded by a nucleic acid with NCBI accession number AY730866.1 (GI: 56718884). The protein from *Helianthus annuus* has 57% overall sequence identity to the ANAC041 polypeptide with SEQ ID NO:5. The ANAC041-related nucleic acid from *Helianthus annuus* has the following sequence SEQ ID NO:14.

```
  1 ACATCACATG GAGAAGCTGC AAAACGCAAA TGCTGTGCTG

41 CGGAGATTGC CTCCCGGTTT CAGGCTTCAC CCAACAGATG

81 AAGAACTTGT TGTACAATAC TTAAAGCGCA GGGTCCACTC

121 TTCTCCTCTG CCTGCTTCCA TCATCCCTGA GGTGGATGTC

161 TGCAAGTCTG ATCCATGGGA CCTGCCCGGA GACTCTGATC

201 AGCAGGAGGA GAGGTTCTTC TTTAGCACCA GAGAGATCAA

241 GTACCCCAAT GGAAACCGAT CCAACAGGGC CACCCAATCC

281 GGTTACTGGA AAGCAACCGG CCTGAGTAGG CAAATTATGG

321 GGGCCAACCA AGTTGGATTG GTTGGCATCA AGAAAACTCT

361 AGTTTTCTAT AAGGGAAAGC CCCCCACCGG CTCCCGAACT

401 GATTGGATCA TGCATGAGTA TCGTCTTGCT ACCACGCAAC

441 CAACTCAGGG TCTGGAAAAG TGGGTACTGT GCAAAATCTT

481 TTTGAAGAAA AGAGGGAACT ACAAGGACGA GAAAAAAAT

521 GTGCCGGTTT TCTATGATTT TCTGGCTACA CCCAAGGTGA

561 AGACGTCGTC GTCGTCGTCA TCAGGCTCAA GTGGGATCAC

601 AGAAGAGAGC AGCACAAATT GTTAATTAGG AGAAATGAAG

641 AATAATGTTT CTTAGTTTTC TAGTACTAGT ATCGATGTTG

681 GAGTTGAAAT TTAGATAGAG TTTGTAATCT CATCTTGTTA

721 AGTGTTAACT TGACTTTTTG CCC
```

The amino acid sequence of the *Helianthus annuus* ANAC041-related polypeptide encoded by the SEQ ID NO:14 nucleic acid has NCBI accession number AAW28153.1 (GI:56718885), with amino acid sequence SEQ ID NO:15 as follows.

```
  1 MEKLQNANAV LRRLPPGFRL HPTDEELVVQ YLKRRVHSSP

41 LPASIIPEVD VCKSDPWDLP GDSDQQEERF FFSTREIKYP
```

-continued

```
 81 NGNRSNRATQ SGYWKATGLS RQIMGANQVG LVGIKKTLVF

121 YKGKPPTGSR TDWIMHEYRL ATTQPTQGLE KWVLCKIFLK

161 KRGNYKDEKK NVPVFYDFLA TPKVKTSSSS SSGSSGITEE

201 SSTNC
```

Any of the ANAC041 and ANAC041-related sequences described herein can be used in the expression cassettes, compositions and methods described herein.

bZIP1 Transcription Factor

The bZIP1 transcription factor binds to the promoter of CslA9. For example, electrophoretic mobility shift assay (EMSA) analysis described herein have confirmed that the bZIP1 factor binds to the CSLA9 promoter (FIG. 3). Transcriptional activation analyses also verify that the bZIP1 protein activates transcription of the CSLA9 gene in vivo (FIG. 6).

Sequences for the bZIP1 transcription factor are available from the National Center for Biotechnology Information (NCBI) database (see, e.g., the website at ncbi.nlm.nih.gov). Genes encoding bZIP1 typically have several introns. Accordingly, a cDNA encoding bZIP1 may conveniently be employed for expression of the bZIP1 protein. For example, a cDNA sequence for an AtbZIP1 (At5g49450) transcription factor from *Arabidopsis thaliana* is available as accession number BT000400.1 (GI:23198383) in the NCBI database, is shown below as SEQ ID NO:16.

```
  1 ATGGCAAACG CAGAGAAGAC AAGTTCAGGT TCCGACATAG

41 ATGAGAAGAA AAGAAAACGC AAGTTATCAA ACCGCGAATC

81 TGCAAGGAGG TCGCGTTTGA AGAAACAGAA GTTAATGGAA

121 GACACGATTC ATGAGATCTC CAGTCTTGAA CGACGAATCA

161 AAGAGAACAG TGAGAGATGT CGAGCTGTAA AACAGAGGCT

201 TGACTCGGTC GAAACGGAGA ACGCGGGTCT TAGATCGGAG

241 AAGATTTGGC TCTCGAGTTA CGTTAGCGAT TTAGAGAATA

281 TGATTGCTAC GACGAGTTTA ACGCTGACGC AGAGTGGTGG

321 TGGCGATTGT GTCGACGATC AGAACGCAAA CGCGGGAATA

361 GCGGTTGGAG ATTGTAGACG TACACCGTGG AAATTGAGTT

401 GTGGTTCTCT ACAACCAATG GCGTCCTTTA AGACATGAGA

441 TTTGTGTATT AGTGTGTGTT TTACTTTGGT CATT
```

The SEQ ID NO:16 nucleic acid encodes a protein with NCBI accession number AAN15719.1 (GI:23198384), which has the following protein sequence (SEQ ID NO:17).

```
  1 MANAEKTSSG SDIDEKKRKR KLSNRESARR SRLKKQKLME

41 DTIHEISSLE RRIKENSERC RAVKQRLDSV ETENAGLRSE

61 KIWLSSYVSD LENMIATTSL TLTQSGGGDC VDDQNANAGI

121 AVGDCRRTPW KLSCGSLQPM ASFKT
```

An AtbZIP1-related factor is available from *Arabidopsis thaliana*, with nucleic acid sequence accession number NM_124322.3 (GI:42568420), provided below as SEQ ID NO:18.

```
  1 TTCTCCCACT TTCCTTATTT TCGATCTTAT CCTTATCTTC

41 TTCCTTGTTC TATTTCTCTT CTAACTAATC TCTTCTCTTC

81 TCTTAAAATC AAACGTAATC ATAAATAAAG ATCTTCTTGT

121 TTAATTTCTC TTGATCCTCG CAAAATCACA GATTCTTGAA

161 ATTCTTTTTT CTTGTCTTGA AATTCTTGAG TTCTTGAGTT

201 ATGAAAAGAC AATGGACAGA GTTATGAAAT GATAAATCTC

241 AACCAATTCC TTGTTTATCA TTCTATATCA GTTGTGATTC

281 TTCATTGGTT TTACGTTATC TCTTGAACAA AAAAACATGG

321 CAAACGCAGA GAAGACAAGT TCAGGTTCCG ACATAGATGA

361 GAAGAAAAGA AAACGCAAGT TATCAAACCG CGAATCTGCA

401 AGGAGGTCGC GTTTGAAGAA ACAGAAGTTA ATGGAAGACA

441 CGATTCATGA GATCTCCAGT CTTGAACGAC GAAGAAAAGA

481 GAACAGTGAG AGATGTCGAG CTGTAAAACA GAGGCTTGAC

521 TCGGTCGAAA CGGAGAACGC GGGTCTTAGA TCGGAGAAGA

561 TTTGGCTCTC GAGTTACGTT AGCGATTTAG AGAATATGAT

601 TGCTACGACG AGTTTAACGC TGACGCAGAG TGGTGGTGGC

641 GATTGTGTCG ACGATCAGAA CGCAAACGCG GAATAGCGG

681 TTGGAGATTG TAGACGTACA CCGTGGAAAT TGAGTTGTGG

721 TTCTCTACAA CCAATGGCGT CCTTTAAGAC ATGAGATTTG

761 TGTATTAGTG TGTGTTTTAC TTTGGTCATT TTATAGTTTT

801 TGTAATCTTT TTATATCGAA TTGTTTCTTC TCATTACTTT

841 CTGAATTCTG ATACAATTGC ATATCTTATT GTTTTCAACA

881 TTTTCATTTA ACGTTATATG ATTTTCG
```

The amino acid sequence of the *Arabidopsis thaliana* AtbZIP1 polypeptide encoded by the SEQ ID NO:18 nucleic acid has 100% sequence identity to the SEQ ID NO:17 protein. The protein encoded by the SEQ ID NO:18 nucleic acid has NCBI accession number NP_199756.1 (GI: 15239895), with SEQ ID NO:19 as follows.

```
  1 MANAEKTSSG SDIDEKKRKR KLSNRESARR SRLKKQKLME

41 DTIHEISSLE RRIKENSERC RAVKQRLDSV ETENAGLRSE

81 KIWLSSYVSD LENMIATTSL TLTQSGGGDC VDDQNANAGI

121 GDCRRTPW KLSCGSLQPM ASFKT
```

A bZIP1 factor is available from black cottonwood *Populus trichocarpa*, which is encoded by a nucleic acid with NCBI accession number XM_002314899.1 (GI: 224108688). The protein from *Populus trichocarpa* has 38% overall sequence identity to the AtbZIP1 polypeptide with SEQ ID NO:17 and 19. The bZIP1-related nucleic acid from *Populus trichocarpa* has the following sequence SEQ ID NO:20.

```
  1 CCTCCGCACC TTTCCTATTT CCTCTTCCAT TAATTAACTC

41 TTTCAGGATT TTCCTTCCCT TTCCTTTTTC TTATTCACAG

81 GATTTTAGTC ATGTTTTCAA AATCATAGAC CTTTCTTGCA
```

-continued

```
121 TGATATGAAC CATCTCAGAC TGTTCTGTCG AATGAAAATT

161 TCCCATTCAG TATCAGTTGT CCTTCTGTAT TGGTTCTATG

201 TCTTTTCTTG AACTTGTCTA ATTTTCAGTC TCACACAACA

241 ACATTTACGT TTTCATTATT TAAGGCTAGC TAGCAACCGT

281 AGTTATATAT TATAATCAGT CCAGTGATCA ATCAAAGAAA

321 ATGCCACCAT CCTTTGCAAA GGCAGGTTCG TCAGGCTCTG

361 AAATTGACCC ACCAAATGCT ATGGTTGATG AGAAGAGAAG

401 AAAAAGAATG ATCTCAAATA GAGAATCTGC AAGGCGGTCG

441 AGAATGAAGA GGCAAAAGTA TATGGAAGAT TTGGTTACTG

481 AAAAATCTAT CTTGGAGAGA AAGATATATG AAGACAATAA

521 AAAATATGCT GCACTTTGGC AAAGGCATTT TGCTCTCGAA

561 TCAGACAACA AAGTTTTGAC GGATGAAAAG TTGAAGCTGG

601 CAGAATATTT GAAGAACTTG CAACAAGTTC TTGCAAGTTA

641 TAATGTCATT GAATCTGATC AGGATCTAGA AGTTTCAGAC

681 CGATTTTTGA ACCCATGGCA AGTTCATGGT TCAGTGAAGT

721 CCATCACAGC TTCTGGGATG TTCAAAGTTT AGTTGTTCTA

761 GTTTTATTTC CATGATTTAT TGTCTTGGGA TTGAGCTTTT

801 GATTTCTCTG GTTATGCTGT TCACATTTGT TTCGGTTT
```

The amino acid sequence of the *Populus trichocarpa* bZIP1 polypeptide encoded by the SEQ ID NO:20 nucleic acid has NCBI accession number XP_002314935.1 (GI:224108689), with SEQ ID NO:21 as follows.

```
  1 MPPSFAKAGS SGSEIDPPNA MVDEKRRKRM ISNRESARRS

41 RMKRQKYMED LVTEKSILER KIYEDNKKYA ALWQRHFALE

81 SDNKVLTDEK LKLAEYLKNL QQVLASYNVI ESDQDLEVSD

121 RFLNPWQVHG SVKSITASGM FKV
```

A bZIP1 factor is available from soybean (*Glycine max*), which is encoded by a nucleic acid with NCBI accession number NM_001249636.1 (GI:351724990). The protein from *Glycine max* has 40% overall sequence identity to the AtbZIP1 polypeptide with SEQ ID NO:17 and 19. The bZIP1-related nucleic acid from *Glycine max* has the following sequence SEQ ID NO:22.

```
  1 CTCTAACCAA GTAGAAGTGC AATAATTAAA TGTCCAACAT

41 CTTCTTGTTG TTGATGTTTG AGATTCATGT ATCCGATTCT

61 CAGTGAAATC TTCTTTTCCG GGTGTATGAT CAATTCCACT

121 GCTAGGCGCA GGACCCATTT AGTTCAATCC TTCTCAGTTG

161 CCTTCCTCTA TTGGTTGTAC TACGTTTCAT GATTTCTAAC

201 CCTTCCTTAG CTTAATAATC ATCTATCTAA AATATCATAA

241 TATCTTCTAC TAGCTAGTTT TATTTTTATT ATCACAATAA

281 AATCTATCTG CAATATATTG TTATTTTTAT TTTCTGAGAA

321 ATTTGTGTCT AGTTATAAGT GTCTGGGTCC TGGTCCTGCC

361 TATTGTGTCA ATTAAATTGA GAAGGGTTGT ATTGCATAGA

401 ATCATATATC GTATCATATA AACATGGCTT GTTCAAGTGG

441 AACATCTTCA GGGTCATTAT CTCTGCTTCA GAACTCTGGT

481 TCTGAGGAAG ATTTGCAGGC GATGATGGAA GATCAGAGAA

521 AGAGGAAGAG AATGATATCA AACCGCGAAT CTGCACGCCG

561 ATCTCGCATG AGGAAGCAGA AGCACTTGGA CGATCTTGTT

601 TCCCAAGTGG CTCAGCTCAG AAAAGAGAAC CAACAAATAC

641 TCACAAGCGT CAACATCACC ACGCAACAGT ACTTAAGCGT

681 TGAGGCTGAG AACTCGGTGC TTAGGGCTCA GGTGGGTGAG

721 TTGAGTCACA GGTTGGAGTC TCTGAACGAG ATCGTTGACG

761 TGTTGAATGC CACCACCACT GTGGCGGGTT TTGGAGCAGC

801 AGCATCGAGC ACCTTCGTTG AGCCAATGAA TAATAATAAT

841 AATAGCTTCT TCAACTTCAA CCCGTTGAAT ATGGGGTATC

881 TGAACCAGCC TATTATGGCT TCTGCAGACA TATTGCAGTA

921 TTGATTGAGA TGCTTCATCT CTGAGATTTG ATGAGGATTT

961 CTTCTTCTTC TTCTTCTGGG TTTGAGTCTG TCGAGAAATT

1001 GTAATCACTA CCATATGATG GTGATAAGGA ATAATATTAA

1041 TAATGAATGT GTATCATAAA AACGGGTGGG ATTGTTAATG

1081 TTAGGTGCTG GTTCCGTAAA TGGGGCATGG GGCATGGGCC

1121 ATTACTGTAA TTTGTCACCC TCCTTTCCTA TATAATAATA

1161 ATAATAATAA TAATAATACT GCCCTCTCTA TGTTATTATT

1201 CTCCCCAAAA AAAAAAAAA AAAAAAAAA AAAAA
```

The amino acid sequence of the *Glycine max* bZIP1 polypeptide encoded by the SEQ ID NO:22 nucleic acid has NCBI accession number NP_001236565.1 (GI:351724991), with SEQ ID NO:23 as follows.

```
  1 MACSSGTSSG SLSLLQNSGS EEDLQAMMED QRKRKRMISN

41 RESARRSRMR KQKHLDDLVS QVAQLRKENQ QILTSVNITT

61 QQYLSVEAEN SVLRAQVGEL SHRLESLNEI VDVLNATTTV

121 AGFGAAASST FVEPMNNNNN SFFNFNPLNM GYLNQPIMAS

161 ADILQY
```

Another bZIP1-like factor is available from sorghum (*Sorghum bicolor*) has NCBI accession number AY730866.1 (GI:56718884 which has 34% overall sequence identity to the AtbZIP1 polypeptide with SEQ ID NO:17 and 19. This sorghum protein bZIP1-like factor has the following sequence SEQ ID NO:24.

```
  1 MSSSRRSSSP DSNNNTDVSG GGGGGFAADE RKRKRMLSNR

41 ESARRSRAKK QQRLEELVAE VARLQAENAA AQSRIAAFER

81 EFAKVDGDNA VLRARHGELS SRLESLGGVL EVLQMAGAAV

121 DIPEMVTEDP MLRPWQPSFP PMQPIGF
```

Another bZIP1-like factor is available from *Capsella rubella*, has 83% overall sequence identity to the AtbZIP1 polypeptide with SEQ ID NO:17 and 19. The amino acid sequence of this *Capsella rubella* bZIP1 polypeptide has NCBI accession number EOA14152.1 GI:482549958), with SEQ ID NO:25 as follows.

```
  1 MANAEKTTTS SGSDIDEKKR KRKLSNRESA RRSRLKKQKQ

41 MEDTIHEISS LERRIKENGE RCKVVKERLD SLETENALLR

81 SEKTWLSSYV CDLENMIATT TLTLTHSGGG GGCDGDEDEN

121 ANAEIAVGDC RRRRPWKLLS CDSLQPMASF KT
```

Any of the bZIP1 and AtbZIP1 sequences described herein can be used in the expression cassettes, compositions and methods described herein.

MYB46 Transcription Factor

As shown herein, the promoter sequence of CSLA9 contains multiple copies of MYB46 binding element, M45RE, which has SEQ ID NO:1 (Kim et al., 2012). Electrophoretic mobility shift assay (EMSA) analyses described herein have confirmed that MYB46 binds to the CSLA9 promoter (FIG. 3). In addition, ChIP experiments followed by real-time PCR provide in vivo confirmation of the interaction between MYB46 and CSLA9 promoter (FIG. 4), and transcriptional activation analyses also verify that the MYB46 protein activates transcription of the CSLA9 gene in vivo (FIG. 6).

Sequences for the MYB46 transcription factor are available from the National Center for Biotechnology Information (NCBI) database (see, e.g., the website at ncbi.nlm.nih.gov). Genes encoding MYB46 typically have several introns. Accordingly, a cDNA encoding MYB46 may conveniently be employed for expression of the MYB46 protein. For example, a cDNA sequence for the *Arabidopsis thaliana* MYB46 transcription factor is available as accession number AT5G12870, and reproduced below as SEQ ID NO:26.

```
  1 ATGAGGAAGC CAGAGGTAGC CATTGCAGCT AGTACTCACC

41 AAGTAAAGAA GATGAAGAAG GGACTTTGGT CTCCTGAGGA

81 AGACTCAAAG CTGATGCAAT ACATGTTAAG CAATGGACAA

121 GGATGTTGGA GTGATGTTGC GAAAAACGCA GGACTTCAAA

161 GATGTGGCAA AAGCTGCCGT CTTCGTTGGA TCAACTATCT

201 TCGTCCTGAC CTCAAGCGTG GCGCTTTCTC CCTCAAGAA

241 GAGGATCTCA TCATTCGCTT TCATTCCATC CTCGGCAACA

281 GGTGGTCTCA GATTGCAGCA CGATTGCCTG GTCGGACCGA

321 TAACGAGATC AAGAATTTCT GGAACTCAAC AATAAAGAAA

361 AGGCTAAAGA AGATGTCCGA TACCTCCAAC TTAATCAACA

401 ACTCATCCTC ATCACCCAAC ACAGCAAGCG ATTCCTCTTC

441 TAATTCCGCA TCTTCTTTGG ATATTAAAGA CATTATAGGA

481 AGCTTCATGT CCTTACAAGA ACAAGGCTTC GTCAACCCTT

541 CCTTGACCCA CATACAAACC AACAATCCAT TTCCAACGGG

581 AAACATGATC AGCCACCCGT GCAATGACGA TTTTACCCCT

601 TATGTAGATG GTATCTATGG AGTAAACGCA GGGGTACAAG

641 GGGAACTCTA CTTCCCACCT TTGGAATGTG AAGAAGGTGA
```

681 TTGGTACAAT GCAAATATAA ACAACCACTT AGACGAGTTG

721 AACACTAATG GATCCGGAAA CGCACCTGAG GGTATGAGAC

761 CAGTGGAAGA ATTTTGGGAC CTTGACCAGT TGATGAACAC

801 TGAGGTTCCT TCGTTTTACT TCAACTTCAA ACAAAGCATA

841 TGA

The amino acid sequence of the *Arabidopsis thaliana* MYB46 polypeptide encoded by the SEQ ID NO:26 nucleic acid is as follows (SEQ ID NO:27).

```
  1 MRKPEVAIAA STHQVKKMKK GLWSPEEDSK LMQYMLSNGQ

41 GCWSDVAKNA GLQRCGKSCR LRWINYLRPD LKRGAFSPQE

121 EDLIIRFHSI LGNRWSQIAA RLPGRTDNEI KNFWNSTIKK

161 RLKKMSDTSN LINNSSSSPN TASDSSSNSA SSLDIKDIIG

201 SFMSLQEQGF VNPSLTHIQT NNPFPTGNMI SHPCNDDFTP

241 YVDGIYGVNA GVQGELYFPP LECEEGDWYN ANINNHLDEL

281 NTNGSGNAPE GMRPVEEFWD LDQLMNTEVP SFYFNFKQSI
```

Nucleic acids and proteins related to the MYB46 are also useful in the methods described herein. For example, a soybean transcription factor with NCBI accession number XM_003543852.1 (GI:356551067) has encodes a protein with 87% overall sequence identity to the MYB46 polypeptide with SEQ ID NO:27. The soybean MYB46-related nucleic acid has the following sequence with SEQ ID NO:28.

```
  1 ATGAACAACA ACATTAAGAG CAAGCTAAGG AAGGGATTGT

41 GGTCACCTGA GGAAGATGAA AAACTCCTAA GGTACATGAT

81 CACTAAGGGA CAAGGGTGTT GGAGTGACAT TGCTAGGAAT

121 GCTGGCCTTC AAAGGTGCGG CAAGAGTTGC CGGCTTCGTT

161 GGATTAACTA CTTGAGACCT GATCTCAAAC GTGGTGCATT

201 TTCACCCCAA GAGGAAGAAC TCATCATTCA TTTGCACTCT

241 ATTCTTGGCA ACAGATGGTC TCAGATTGCG GCACGTCTCC

281 CTGGTCGCAC AGACAATGAG ATCAAGAATT TCTGGAACTC

321 CACTCTGAAG AAAAGGTTGA AAATGAACAA CAATATTAAC

361 GCCACTTCAT CACCAAACAA TAGCTACTCA TCATCAGAGC

401 CTAGAGATGT CAATGTCATG GGTGGGATCA TGCCCATGAA

441 CGAGCATGAC CTCATGACCA TGTGCATGGA CTCCTCCTCA

481 TCAACATCAT CATCATGCAT GCAATCCATG CATACAACCA

521 ACATGGTACT AACTGACCAA TTTGATCCCT TTCCCTTGTT

561 GTCCAACAAC CGTTACGACA TGACCGGCGC AACCGATTTC

601 CTTGACAACA TGGCTGCATG CTTAACCCAA GTTGGCATGG

641 TAGATCATGA TCATGGGGTT GTTCATGATG GTTATGGGAC

681 ATTGGAGCCT AACAAAACGG GTTTAGAAAG TGACTTTTCC

721 CTTCCTCCAC TAGAAAGTAG AAGCATTGAC GACAATAGTA

761 GTACCCCAAT TGATCATGTG AAAAGCCATA ACAACAACAA
```

```
801  CCACTTCAAG AATAGTTGCT TCAATAACAC TGATCATCAC

841  CATCATATCC AATGCTCCAA CAACGTAGTT GTAGAGGATT

881  TGTTTGGGTT TGGAAATCAT GGACATGGAG AAAGCTTTAG

921  AATGGAAGAA TGGGACTTTG AGGGTTTGAT TCAAGATATT

961  CCCTATTTTT CTTCCCTTGA TTTCCAAGTT TAA
```

The protein sequence for the soybean nucleic acid with SEQ ID NO:28 has accession number XP_003543900.1 (GI:356551068) in the NCBI database, and the following sequence (SEQ ID NO:29).

```
  1  MNNNIKSKLR KGLWSPEEDE KLLRYMITKG QGCWSDIARN

41  AGLQRCGKSC RLRWINYLRP DLKRGAFSPQ EEELIIHLHS

61  ILGNRWSQIA ARLPGRTDNE IKNFWNSTLK KRLKMNNNIN

121  ATSSPNNSYS SSEPRDVNVM GGIMPMNEHD LMTMCMDSSS

161  STSSSCMQSM HTTNMVLTDQ FDPFPLLSNN RYDMTGATDF

181  LDNMAACLTQ VGMVDHDHGV VHDGYGTLEP NKTGLESDFS

241  LPPLESRSID DNSSTPIDHV KSHNNNNHFK NSCFNNTDHH

281  HHIQCSNNVV VEDLFGFGNH GHGESFRMEE WDFEGLIQDI

301  PYFSSLDFQV
```

Another MYB46-related protein is available from *Populus trichocarpa*, which is encoded by a nucleic acid with NCBI accession number XM_002313298.1 (GI:224104138). The protein from *Populus trichocarpa* has 90% overall sequence identity to the MYB46 polypeptide with SEQ ID NO:27. The MYB46-related nucleic acid from *Populus trichocarpa* has the following sequence SEQ ID NO:30.

```
  1  AAGTTCAGAA AGGGCTTGTG GTCACCAGAG GAAGATGACA

41  AGCTCATGAA CTACATGCTA AACAATGGAC AAGGTTGCTG

81  GAGTGATGTG GCAAGGAATG CTGGTTTGCA GCGATGCGGC

121  AAGAGTTGCC GGCTTCGTTG GATTAATTAC TTGAGGCCTG

161  ATCTCAAGAG AGGTGCATTT TCACCCCAAG AAGAAGAGAT

201  GATCATCCAT TTGCATTCCC TTCTCGGCAA TAGGTGGTCT

241  CAAATTGCGG CTCGCTTGCC AGGAAGAACG GACAATGAAA

281  TCAAGAATTT TTGGAATTCA ACAATAAAGA AGAGATTAAA

321  G
```

The protein sequence for the *Populus trichocarpa* nucleic acid with SEQ ID NO:30 has accession number XP_002313334.1 (GI:224104139) in the NCBI database, and the following sequence (SEQ ID NO:31).

```
  1  KFRKGLWSPE EDDKLMNYML NNGQGCWSDV ARNAGLQRCG

41  KSCRLRWINY LRPDLKRGAF SPQEEEMIIH LHSLLGNRWS

81  QIAARLPGRT DNEIKNFWNS TIKKRLK
```

Another MYB46-related protein is available from *Zea mays*, which is encoded by a nucleic acid with NCBI accession number NM_001254930.1 (GI:363543286). The protein from *Zea mays* has 65% overall sequence identity to the MYB46 polypeptide with SEQ ID NO:27. The MYB46-related nucleic acid from *Zea mays* has the following sequence SEQ ID NO:32.

```
   1  GTACCCAGCT ATAGGACGGC AATGAGGAAA CCGGAACGCC

41  CAGCGGCGAA CAGCAGCAAT GCGGGGCGG CGGCCGCGAA

81  GCTGCGGAAG GGGCTGTGGT CGCCGGAGGA GGACGAGAGG

121  CTGGTGGCGT ACATGCTGCG GAGTGGACAG GGTTCTTGGA

161  GCGATGTGGC CCGGAACGCC GGGTTGCAGC GGTGCGGCAA

201  GAGCTGCCGC CGCCGGAGGA TCAACTACCT CCGGCCGGAC

241  CTCAAGCGCG GCGCCTTCTC GCCGCAGGAG GAGGAGCTCA

281  TCGTCAGCCT CCACGCCATC CTGGGAAACA GGTGGTCTCA

321  GATTGCTGCC CGGTTGCCGG GGCGCACCGA CGACGACGAC

361  AAGAACTTCT GGAACTCCAC CATCAAGAAG CGGCTCAAGA

401  ACAGCTCGGC AGCTTCGTCA CCAGCAGCTA CGGACTGCGC

441  GCCGCAGGAG CCTAATAACA AGGTCGCCGC CGCCGGTAGC

481  TGCCCGGATC TTTCCGTCCT AGATCATCAG GACGGTGGCC

521  ACCACCACGC AATGACGACG ACGACTGCAG GTTTGTGGAT

561  GGTGGACTCA TCCTCCTCTT GTACCTCGTC GACCTCGCCA

601  ATGCATCAGT TTCAGAGGCC GACGACGACG ATGGCAGCGG

641  CCGTGGCCAG CGGGAGCTAT GGAGGTCTCG TCCCCTTCCC

681  TGACCAGGTC CGTGGTGTTG TGGCCGACAC GGGAGGGTTC

721  TTTCATGGCC ACGCGGCGCC AGCGTTCAAG CACCAAGTTG

761  CCGCATTGCA CGGTGGTGGT TATTACTACG GCAGCGCTCC

801  TCGTCACCAT GGAATGACGA CGACGACGAC GACGGTGGCA

841  TTGGAAGGAA GCGGTGGATG CTTCATATCT GGCGAAGGCA

881  TGCTTGGTGT GCCCCCTCTG CTGTTAGAGC CCATGTCAGC

921  AGCGCTAGAG CAAGACCAAG GCCAGACCTT GATGGCATCA

961  AGTGGTAACA ACAACCCTAA AAACAACAGC AGCAGCAACA

1001  CTACTGATAC TACGACTACC ACGACACTGA GCAACAATGA

1041  GAGCAACGTC ACAGACACCA CCACCAAGGA CAACACCACC

1081  AACACCATCA GCCAAGTGAA CAGTGGCAGC AATAATGTCT

1121  ACTGGGAGGG GGCCCGCCAG CAGTACATGA GCAGGAATGT

1161  CATGCATGGG GAGTGGGACC TGGAGGAGCT GATGAAAGAT

1201  GTGTCATCCT TGCCTTTTCT TGATTTCCAA GTTGAATGAT

1241  TGGGAGGGCC GTGTTGCATC TCCAGC
```

The protein sequence for the *Zea mays* nucleic acid with SEQ ID NO:32 has accession number NP_001241859.1 (GI:363543287) in the NCBI database, and the following sequence (SEQ ID NO:33).

```
  1 MRKPECPAAN SSNAGAAAAK LRKGLWSPEE DERLVAYMLR

41 SGQGSWSDVA RNAGLQRCGK SCRLRWINYL RPDLKRGAFS

81 PQEEELIVSL HAILGNRWSQ IAARLPGRTD NEIKNFWNST

121 IKKRLKNSSA ASSPAATDCA SPEPNNKVAA AGSCPDLSVL

161 DHQDGGHHHA MTTTTAGLWM VDSSSSCTSS TSPMHQFQRP

201 TTTMAAAVAS GSYGGLVPFP DQVRGVVADT GGFFHGHAAP

241 AFKHQVAALH GGGYYYGSAP RHHGMTTTTT TVALEGSGGC

281 FISGEGMLGV PPLLLEPMSA ALEQDQGQTL MASSGNNNPK

321 NNSSSNTTDT TTTTTLSNNE SNVTDTTTKD NTTNTISQVN

361 SGSNNVYWEG ARQQYMSRNV MHGEWDLEEL MKDVSSLPFL

401 DFQVE
```

Another MYB46-related protein is available from barley (*Hordeum vulgare*), which is encoded by a nucleic acid with NCBI accession number AY672068.1 (GI:52352764). The protein from *Hordeum vulgare* has 68% overall sequence identity to the MYB46 polypeptide with SEQ ID NO:27. The MYB46-related nucleic acid from *Zea mays* has the following sequence SEQ ID NO:34.

```
  1 GTACTTGCAG CCTTGGAGAT CGACCTGGTC TCTAGATAGG

41 ATAGCTAGTA CAGTCCATAA CTACATCTTT GCTAGGAGAT

81 CGGGCTGGGC AATGAGGAAG CCCGTGGAGT GCCCGGCGAC

121 GAAGTGCAGT GGTGGTGTGG CGCCAGGAAA CAGCAATGTG

161 GCTGCAGCGG CGGCCAAGCT GCGGAAGGGG CTGTGGTCGC

201 CGGAGGAGGA CGAGAGGCTT GTGGCGTACA TGCTGCGGAG

241 CGGTCAGGGG TCGTGGAGCG ACGTGGCACG CAACGCCGGG

281 TTACAGCGGT GCGGCAAGAG CTGCCGCCTC CGGTGGATCA

321 ACTACCTCCG TCCGGACCTC AAGCGCGGCG CCTTCTCGCC

361 ACATGAGGAG GACCTCATCG TCAACCTCCA CGCCATCCTC

401 GGCAACAGAT GGTCTCAGAT CGCAGCCAGG TTACCGGGGC

421 GCACCGACAA CGAGATCAAG AACTTCTGGA ACTCCACCAT

481 CAAGAAGCGG CTGAAGATGA ACTCGGCCGC TTCGTCTCCG

521 GCGACCACGG AATGTGCGTC ACCGCCCGAG CCCAACCTCG

561 ACGGCGGCAG TGCCAGCTGC CTCGACCTCA CCAGCCAGGA

601 GGACGGGAGC CACCACGCAA TGAAAAGCAT GTGGATGGAC

641 TCATCCTCCT CCTCCTCTTC GTCTTCGTCG ATGCAGCAGG

681 GGAGCCGACC GTCAACAATG GCTCCGGCGG CAAACAGGGG

721 CTACGGGGGC CTCCTCCTGC CCCTCCCGGA CCAAGTCTGC

761 GGCGTCGCAC CTTCCACCCA CACGTCGTTG CCGCCGTTCT

801 TCCAAGACCA TTCATCGTTT AAGCAGGTTT CTCCCTTGCG

841 GGACGGGAGC TACTACCCTC ACGGAATGGC AATGGAAGGA

881 GCAGGTGGCT GCTTCATGGG AGAAGAAGCT GTAGGCGGTG

921 GAGGCGAACG TAGTGTCGTC TTCAACGTGC CCCCTCTACT

961 AGAGCCCATG GCAGTAGCAT TGCAAGACCA AACCTTAATG

1001 GCATCAACTG GTAACAGCAA CAATAACCAT CGAAACACTA

1041 ACAGTACTGC AGAGGGCACC ACACTGAGCA GCAAAAATGG

1081 CTGCAACATC AATGACGACA ACACCAGTAA GAACAACATC

1121 AACAGTGTGG TCTCGTACTG GGAGCAGCAT GGTCAGCAGC

1161 AGCACATGAG CAGGAACGTA GTCATGGGGG AGTGGGACTT

1201 GGAGGAGCTC ATGAAAGACG TGTCATGCTT GCCTTTCCTT

1241 GATTTCCAAG TTGAGTGATG ACACGCTGTT GGGGGCCACC

1281 TCCTACCTGC GTGCCTAAAC TACATGCATA TACGAATATA

1321 CATATATAAT TAAGTATATA TACACATGCA TACGTTAAAG

1361 GTAGTCTTTT TTTCCTTGAC ATTATTTACA TGATGTACGC

1401 AAGATTTCTT CAGCAGCCAC TACTTCACTT TTGATACTAC

1441 ATATATCTTT GATGAATTCA TTCTTGTATA CAGATACTCA

1481 TGCCTATGCA AATAATTCAA GCAAAGTTAC TTGAGTTAAT

1521 AAAAAAAAAA AAAAAAAAAA AA
```

The protein sequence for the barley nucleic acid with SEQ ID NO:34 has accession number AAU43823.1 (GI: 52352765) in the NCBI database, and the following sequence (SEQ ID NO:35).

```
  1 MRKPVECPAT KCSGGVAPGN SNVAAAAAKL RKGLWSPEED

41 ERLVAYMLRS GQGSWSDVAR NAGLQRCGKS CRLRWINYLR

81 PDLKRGAFSP HEEDLIVNLH AILGNRWSQI AARLPGRTDN

121 EIKNFWNSTI KKRLKMNSAA SSPATTECAS PPEPNLDGGS

161 ASCLDLTSQE DGSHHAMKSM WMDSSSSSSS SSSMQQGSRP

201 STMAPAANRG YGGLLLPLPD QVCGVAPSTH TSLPPFFQDH

241 SSFKQVSPLR TGGYYPHGMA MEGAGGCFMG EEAVGGGGER

281 SVVFNVPPLL EPMAVALQDQ TLMASTGNSN NNHRNTNSTA

321 EGTTLSSKNG CNINDDNTSK NNINSVVSYW EQHGQQQHMS

361 RNVVMGEWDL EELMKDVSCL PFLDFQVE
```

Any of the MYB46, and MYB46-related sequences described herein can be used in the expression cassettes, compositions and methods described herein.

CSLA9

The transcription factors described herein can increase expression of the CSLA9 gene product, also referred to as glucomannan 4-beta-mannosyltransferase 9. CSLA9 has glucomannan synthase and mannan synthase activities. Such a mannan synthase involves 4-beta-mannosyltransferase activity on mannan using GDP-mannose as a substrate. The beta-1,4-mannan product is the backbone for galactomannan synthesis by galactomannan galactosyltransferase. Galactomannan is a noncellulosic polysaccharide of plant cell wall.

Sequences of the CSLA9 polypeptide are available, for example, in the NCBI database. One example, of an *Arabidopsis thaliana* CSLA9 polypeptide sequence is available as NCBI accession number Q9LZR3.1 (GI:75181330), which has the following sequence (SEQ ID NO:36).

```
  1  MELGDTTSVI PDSFMGYRDD ITMQMSMVLD QIRAPLIVPA
 41  LRLGVYICLT MSVMLFVERV YMGIVISLVK LFGRKPDKRF
 81  KYEPIKDDIE LGNSAYPMVL IQIPMFNERE VYQLSIGAAC
121  GLSWPSDRIV IQVLDDSTDP TIKDLVEMEC SRWASKGVNI
161  KYEIRDNRNG YKAGALKEGM KKSYVKSCDY VAIFDADFQP
201  EADFLWRTVP YLLHNPKLAL VQARWKFVNS DECLMTRMQE
241  MSLDYHFTVE QEVGSSTYAF FGFNGTAGIW RISALNEAGG
281  WKDRTTVEDM DLAVRASLKG WKFLYLGSLK VKNELPSTFK
321  AYRYQQHRWS CGPANLFRKM AFEIMTNKNV TLWKKVHVIY
361  SFFVVRKLVA HIVTFIFYCV ILPATVLVPE VTVPKWGAVY
401  IPSVITLLNA VGTPRSLHLM VFWILFENVM SLHRTKATFI
441  GLLEGGRVNE WIVTEKLGDV KAKSATKTSK KVIRFRFGDR
481  IHVLELGVGM YLLFVGCYDA FFGKNHYYLY LFAQAIAFFI
521  AGFGQIGTIV PNH
```

Genes encoding CSLA9 typically have several introns. Accordingly, a cDNA encoding CSLA9 may conveniently be employed for expression of the CSLA9 protein. A nucleic acid encoding the *Arabidopsis thaliana* CSLA9 polypeptide shown above (SEQ ID NO:6). This CSLA9 cDNA has a sequence with accession number NM_120457.3 (GI: 145357607) is also available in the NCBI database, and is provided below as SEQ ID NO:37.

```
   1 CACACACACA CACACACACA CAACACTGTG TCTTCTCTCC
  41 CTCTGTTTCT GTTTTTAGAT CTCTCTTCTC TCTTCTTTCT
  81 TTCCAAAAAT CATCTTCTCC TTCTCCACCT TTCATTATCT
 121 TTCTTCTCTT ACCAAAACCC TTTAAATACA AAAAAAAACT
 161 AAAAACGAAA AAAAAAATAT TGAATTCTCC TTTTTCCCGA
 201 CAATCTGAGT TTCTCAGGCA GAGAAGACAG AGATTTTCAC
 241 CGTAAGGGCA AAAAACGAAA AACTCTGTCT CTCTGTTTCT
 281 GTTTCGTCCT TCCTTGGCTT TGATTTCTTA CACCAAAAGA
 321 GACATCTTTA AAGAATCTCA CATTGTTCCC TATTGCTTGT
 361 CTCACAAGAG AATCCTTGAT CTAGGGTTCT TGCTTCCCTC
 401 CTCTGTTTCT TTCTTTAAAT TCCTCCTCTG TTTTCTTTTT
 441 GTTCTCGTCG GAGTAAGAAG AGATGGAGCT AGGAGATACG
 481 ACGTCGGTGA TTCCAGACTC GTTCATGGGA TACAGAGACG
 521 ACATAACAAT GCAAATGTCA ATGGTTTTGG ATCAGATACG
 561 AGCTCCATTG ATTGTTCCAG CCCTTAGGCT CGGTGTTTAC
 601 ATCTGTTTGA CAATGTCGGT GATGCTCTTT GTTGAAAGGG
 641 TTTACATGGG AATTGTTATC TCTCTTGTGA AGCTGTTTGG
 681 TCGAAAACCA GATAAACGTT TCAAATATGA ACCAATCAAA
 721 GATGACATCG AGCTTGGAAA CTCTGCTTAC CCGATGGTTC
 761 TTATTCAAAT CCCAATGTTC AACGAACGAG AGGTTTATCA
 801 ACTATCTATT GGAGCTGCTT GTGGACTCTC ATGGCCTTCT
 841 GATCGAATCG TTATTCAAGT TCTTGATGAT TCCACTGATC
 881 CAACGATCAA AGATCTAGTG GAGATGGAGT GTAGCAGGTG
 921 GGCGAGTAAA GGAGTAAACA TCAAGTATGA GATCAGAGAC
 961 AACAGAAATG GATACAAAGC AGGAGCTTTG AAAGAAGGAA
1001 TGAAGAAGAG TTATGTCAAA AGCTGCGATT ACGTTGCAAT
1041 CTTCGACGCT GATTTTCAAC CTGAAGCGGA TTTTCTATGG
1081 AGAACCGTAC CGTATCTACT CCATAACCCT AAGCTTGCTC
1121 TTGTTCAAGC TCGCTGGAAA TTCGTAAATT CGGATGAATG
1161 TTTGATGACA AGGATGCAAG AAATGTCTTT GGATTATCAT
1201 TTTACGGTGG AACAAGAAGT TGGTTCTTCT ACTTACGCTT
1241 TCTTCGGATT CAATGGAACT GCGGGAATAT GGAGAATATC
1281 GGCATTAAAC GAAGCTGGTG GTTGGAAAGA TAGAACGACC
1321 GTGGAAGATA TGGATTTGGC CGTGAGAGCT AGTCTCAAGG
1361 GTTGGAAATT CTTGTACCTC GGTTCTTTGA AGGTTAAAAA
1401 CGAGTTGCCA AGTACATTCA AGGCTTATAG GTATCAACAG
1441 CACAGGTGGT CATGTGGTCC AGCTAATCTT TTCAGGAAAA
1481 TGGCATTCGA AATCATGACT AATAAGAACG TGACTTTGTG
1521 GAAGAAAGTT CATGTGATAT ATAGCTTCTT CGTGGTTAGA
1561 AAGCTAGTGG CACACATTGT TACCTTCATC TTCTACTGTG
1601 TGATCTTACC CGCTACAGTT CTTGTACCGG AAGTTACTGT
1641 TCCGAAATGG GGAGCGGTTT ACATTCCTTC AGTCATTACT
1681 CTCCTCAACG CCGTTGGGAC ACCAAGGTCA TTGCATCTTA
1721 TGGTCTTTTG GATTCTGTTC GAGAATGTGA TGTCTCTTCA
1761 CAGAACAAAA GCTACCTTTA TCGGTTTACT CGAAGGAGGA
1801 AGAGTTAATG AGTGGATTGT TACAGAGAAG CTGGGAGATG
1841 TTAAGGCTAA ATCAGCCACC AAGACTTCAA AGAAGGTTAT
1881 TCGTTTTAGA TTTGGAGATA GAATTCATGT GTTGGAACTC
1921 GGTGTAGGAA TGTATCTGTT ATTTGTGGGA TGTTATGACG
1961 CGTTTTTTGG GAAGAATCAT TATTATCTAT ACCTTTTCGC
2001 ACAAGCAATC GCGTTCTTCA TTGCGGGATT CGGGCAAATT
2041 GGGACAATTG TGCCTAACCA TTGAAGGGAA AAAGGAGTTT
2081 TCGAGCGACG AATTGCTCGA GGATAAGAAG ATGATTTGTT
2121 TTCTTTCTTT TTGGATTCGC TAGCTATTTA AATTCTTGTT
2161 GGTGTGAATA GAGAGAATTG ATGATACCAT TGTTACAGAA
2201 ATGGTGTGTG TAGTGTGGAA GATAAAGGAT ACTTATAGTA
2241 AAGAAGAAAT ATACTTTGAA GGTTTTTTTC AGATTCCTTG
2281 AAGGCAAATG ATTTTTGAC
```

One example of a structure for the promoter region of a CSLA9 gene is the following promoter sequence (SEQ ID NO:38) from an *Arabidopsis thaliana* CSLA9 gene (containing 1500 base pair UP plus 5'UTR, where the 5'UTR is underlined)

```
   1 ATCACCAAGAGA AGCAACGA AATGTTTGGA TCACATGGAT
  41 CCTTTTCCTT TAACCCAAAA CTAATGACCG TATAAGAGTC
  81 AACTTCAGCC GTTGAGCAGT CCTTATTTTC CAGCTATGTG
 121 TTTCATTTTA TCATCGTTTT AAAAATGATC GAGATCCATT
 161 TACTTTTTTA GTCAACATTA TTTCCTTTAA ATTGCGATTT
 201 GAATATATTA ACTTAAAAGA TTACGAAGTA AAAATGATTG
 241 ATGAACGAAG TCGAAACGTG CTTCGAAGTT TATGAAATAA
 281 TTGACTTTTT GTATACTTAA AAAAATTTGA CTTTAAACAA
 321 ACAGAAAACT TTTTATTTAT GGTACTTAAT TAGAATATAA
 361 CAAACTGGAC CGTCGGTGGG ATTTGAAGCA TCATGGCAAA
 401 TGTGCGTTGT TTTAAAATGT CTTGAATATT CATCTTCTCC
 441 TTTGGAGAGC TTCTGTTCGA TTTTGATTGG TCGAAATATA
 481 TGACATAACA TATTTCCACT GAATTGTAAA TAATGTATTA
 521 GGTATAGTGG CATATAACTC AATGCTAAAA ACATATATCA
 561 ATTTACTGGA TTTCACAAAA TTGTAACTCA ATGTTACTCT
 601 ATATATGGAC CACTGCATGA TATCCATGTC TTGTACTAAG
 641 GATTCGATCA TTCGATTATC CTCACAAGAG ATGTTCGCTA
 681 TCTTGTCAAT AGATGAGGAC AAACAATATG AGACGATATA
 721 TTTTTCCCGA GAAATGAACC ATTAGAATCA CTCTGTTTCT
 761 GGAATTAACC GGTTATGCAA GTCCATATGA TTTGTATAAA
 801 TACTGATATA CATAATGCTC ATCTATAATG CCCTGTTTTT
 841 TCATTCAGCT CTAAAATATT ATAAGTAATG TTATTGAGCC
 881 TCGATTGATT GATTGACAAA AAAAAAAAAT GTTATTGAGC
 921 CTCTGTTTCT TTTTTTGAGC CTTTAATTGG TAGTTCTATA
 961 TTTAAATACA TATTATATCA ACTGATTAAT CTTCGATTTC
1001 TTGAGCTTAA AAATAAAATA AAAAACGAAA CGCTGGCTAG
1041 CAAATTGTTT TGACTGAGAT GGTCCTATAG TTTTGGACGC
1081 CTAGACGGCT ATAAACTATC GAGTTTTAAC CTTATACATA
1121 ATTCATAGTT GTTACGAATT ATAATTAGGC AATTACACAT
1161 TTGTATTATA TTCATTATCT ATGTCACCTC GAGAAGACAG
1201 AAGCATTTTT TTTAACAATG ACATTTTTAT TTTTTAAGAA
1241 AATTATTTTA TCAGAAACTT AAAAACGAAA TTTTCTTTTT
1281 ATCTTCGCCT GGACGTCATT AATGTTTGTG TCGTTCAATA
1321 ATGTTTGGTA GTTATATATA GAAAGAGCAA ATTTATGGTT
1361 GATTGATGGT GCAAAAAAT TCATTTCTCT ATATTCTAGA
1401 GAAATAAAAT AAAAACGAAA TGGAATATTA AATAGAGTCT
1441 AAAACAATAT ACACAAGGAC AGAGCCTTTA TATATAAAGA
1481 CATTGATCTC TCTCTGATTT CTCACACACA CACACACACA
1521 CAACACTGTG TCTTCTCTCC CTCTGTTTCT GTTTTTAGAT
1561 CTCTCTTCTC TCTTCTTTCT TTCCAAAAAT CATCTTCTCC
1601 TTCTCCACCT TTCATTATCT TTCTTCTCTT ACCAAAACCC
1641 TTTAAATACA AAAAAAAACT AAAACACATA AAAAAAATAT
1681 TGAATTCTCC TTTTTCCCGA CAATCTGAGT TTCTCAGGCA
1721 GAGAAGACAG AGATTTTCAC CGTAAGGGCA AAAAACGAAA
1761 AACTCTGTCT CTCTGTTTCT GTTTCGTCCT TCCTTGGCTT
1801 TGATTTCTTA CACCAAAAGA GACATCTTTA AAGAATCTCA
1841 CATTGTTCCC TATTGCTTGT CTCACAAGAG AATCCTTGAT
1881 CTAGGGTTCT TGCTTCCCTC CCCTGTTTTT TTCTTTAAAT
1921 TCCTCCTCTG TTTTCTTTTT GTTCTCGTCG GAGTAAGAAG
1961 AGATG
```

This sequence contains two binding sites for transcription factors such as MYB46, bZIP1, and ANAC041, as shown herein.

Such promoter sequences can be used in expression cassettes to drive the expression of selected coding regions. Such expression of an operably linked coding region can be inducibly expressed. For example, the expression of a selected coding region can be induced by any of the MYB46, ANAC041, bZIP1, and related transcription factors described herein.

Related Nucleic Acids or Polypeptides

The nucleic acids, polypeptides, promoters, plants, and seeds, can also include transcription factors and promoters that have sequences related to any of the sequences described herein. For example, related nucleic acids can be isolated and identified by mutation of the SEQ ID NO:3, 5, 7, 9, 11, 13, 15, 17, 19, 21, 23, 24, 25, 27, 29, 31, 33, or 35 amino acid sequence and/or by hybridization to DNA and/or RNA isolated from other plant species using any of SEQ ID NO:2, 4, 6, 8, 10, 12, 14, 16, 18, 20, 22, 26, 28, 30, 32, 34, 35, 37, or 38 nucleic acids (or portions thereof) as probes.

In some embodiments, the related nucleic acids and proteins are identified by hybridization of any of SEQ ID NO:2, 4, 6, 8, 10, 12, 14, 16, 18, 20, 22, 26, 28, 30, 32, 34, 35, 37, or 38 nucleic acids (or portions thereof) as probes under stringent hybridization conditions. The terms "stringent conditions" or "stringent hybridization conditions" include conditions under which a probe will hybridize to its target sequence to a detectably greater degree than other sequences (e.g., at least 2-fold over background). Stringent conditions are somewhat sequence-dependent and can vary in different circumstances. By controlling the stringency of the hybridization and/or washing conditions, target sequences can be identified with up to 100% complementarity to the probe (homologous probing). Alternatively, stringency conditions can be adjusted to allow some mismatching in sequences so that lower degrees of sequence similarity are detected (heterologous probing). The probe can be approximately 20-500 nucleotides in length, but can vary greatly in length from about 18 nucleotides to equal to the entire length of the target sequence. In some embodiments, the probe is about 10-50 nucleotides in length, or about 18-25 nucleotides in length, or about 18-50 nucleotides in length, or about 18-100 nucleotides in length.

Typically, stringent conditions will be those where the salt concentration is less than about 1.5 M Na ion (or salts thereof), typically about 0.01 to 1.0 M Na (sodium) ion concentration (or salts thereof), at pH 7.0 to 8.3 and the temperature is at least about 30° C. for shorter probes (e.g., 10 to 50 nucleotides), and at least about 60° C. for longer probes (e.g., greater than 50 nucleotides). Stringent conditions may also be achieved with the addition of destabilizing agents such as formamide or Denhardt's solution. Exemplary low stringency conditions include hybridization with a buffer solution of 30 to 35% formamide, 1M NaCl, 1% SDS (sodium dodecyl sulfate) at 37° C., and a wash in 1×SSC to 2×SSC (where 20×SSC is 3.0 M NaCl, 0.3 M trisodium citrate) at 50 to 55° C. Exemplary moderate stringency conditions include hybridization in 40 to 45% formamide, 1M NaCl, 1% SDS at 37° C., and a wash in 0.5×SSC to 1×SSC at 55 to 60° C. Exemplary high stringency conditions include hybridization in 50% formamide, 1M NaCl, 1% SDS at 37° C., and a wash in 0.1×SSC at 60 to 65° C. Specificity is typically a function of post-hybridization washes, where the factors controlling hybridization include the ionic strength and temperature of the final wash solution.

For DNA-DNA hybrids, the $T_m$ can be approximated from the equation of Meinkoth and Wahl (Anal. Biochem. 138: 267-84 (1984)):

$$T_m = 81.5° C. + 16.6(\log M) + 0.41(\% GC) - 0.61(\% \text{formamide}) - 500/L$$

where M is the molarity of monovalent cations; % GC is the percentage of guanosine and cytosine nucleotides in the DNA, % formamide is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. The $T_m$ is reduced by about 1° C. for each 1% of mismatching. Thus, the $T_m$, hybridization and/or wash conditions can be adjusted to hybridize to sequences of the desired sequence identity. For example, if sequences with greater than or equal to 90% sequence identity are sought, the $T_m$ can be decreased 10° C. Generally, stringent conditions are selected to be about 5° C. lower than the thermal melting point $(T_m)$ for the specific sequence and its complement at a defined ionic strength and pH. However, severely stringent conditions can include hybridization and/or a wash at 1, 2, 3 or 4° C. lower than the thermal melting point $(T_m)$. Moderately stringent conditions can include hybridization and/or a wash at 6, 7, 8, 9 or 10° C. lower than the thermal melting point $(T_m)$. Low stringency conditions can include hybridization and/or a wash at 11, 12, 13, 14, 15 or 20° C. lower than the thermal melting point $(T_m)$. Using the equation, hybridization and wash compositions, and a desired $T_m$, those of ordinary skill can identify and isolate nucleic acids with sequences related to any of SEQ ID NO:2, 4, 6, 8, 10, 12, 14, 16, 18, 20, 22, 26, 28, 30, 32, 34, 35, 37, or 38 nucleic acids.

Those of skill in the art also understand how to vary the hybridization and/or wash solutions to isolate desirable nucleic acids. For example, if the desired degree of mismatching results in a $T_m$ of less than 45° C. (aqueous solution) or 32° C. (formamide solution) it is preferred to increase the SSC concentration so that a higher temperature can be used.

An extensive guide to the hybridization of nucleic acids is found in Tijssen, LABORATORY TECHNIQUES IN BIOCHEMISTRY AND MOLECULAR BIOLOGY—HYBRIDIZATION WITH NUCLEIC ACID PROBES, part 1, chapter 2, "Overview of principles of hybridization and the strategy of nucleic acid probe assays," Elsevier, N.Y. (1993); and in CURRENT PROTOCOLS IN MOLECULAR BIOLOGY, chapter 2, Ausubel, et al., eds, Greene Publishing and Wiley-Interscience, New York (1995).

For example, high stringency can be defined as hybridization in 4×SSC, 5×Denhardt's (5 g Ficoll, 5 g polyvinylpyrrolidone, 5 g bovine serum albumin in 500 ml of water), 0.1 mg/ml boiled salmon sperm DNA, and 25 mM Na phosphate at 65° C., and a wash in 0.1×SSC, 0.1% SDS at 65° C. However, the stringency of hybridization is actually determined by the wash conditions. Thus, wash conditions in 0.1×SSC, 0.1% SDS at 65° C. are a sufficient definition of stringent hybridization conditions.

Such selective hybridization substantially excludes non-target nucleic acids. Selectively hybridizing sequences typically have about at least 40% sequence identity, at least about 50% sequence identity, at least 55% sequence identity, at least about 60% sequence identity, at least 70% sequence identity, at least about 80% sequence identity, at least 90% sequence identity, at least about 95% sequence identity, or 40-95% sequence identity, or 50-95% sequence identity, or 60-90% sequence identity, or 90-95% sequence identity, or 90-99% sequence identity, or 95-97% sequence identity, or 98-99% sequence identity, or 100% sequence identity or complementarity with any of the SEQ ID NO:2, 4, 6, 8, 10, 12, 14, 16, 18, 20, 22, 26, 28, 30, 32, 34, 35, 37, or 38 nucleic acids.

The nucleic acids of the invention include those with about 500 of the same nucleotides as any of SEQ ID NO:2, 4, 6, 8, 10, 12, 14, 16, 18, 20, 22, 26, 28, 30, 32, 34, 35, 37, or 38 nucleic acids, or about 600 of the same nucleotides, or about 700 of the same nucleotides, or about 800 of the same nucleotides, or about 900 of the same nucleotides, or about 1000 of the same nucleotides, or about 1100 of the same nucleotides, or about 1200 of the same nucleotides, or about 1300 of the same nucleotides, or about 500-1325 of the same nucleotides. The identical nucleotides or amino acids can be distributed throughout the nucleic acid, and need not be contiguous.

The transcription factor polypeptides of the invention include those with about 50 of the same amino acids as any of SEQ ID NO:3, 5, 7, 9, 11, 13, 15, 17, 19, 21, 23, 24, 25, 27, 29, 31, 33, 35, or 36 polypeptides, or about 60 of the same amino acids, or about 70 of the same amino acids, or about 80 of the same amino acids, or about 90 of the same amino acids, or about 100 of the same amino acids, or about 110 of the same amino acids, or about 120 of the same amino acids, or about 130 of the same amino acids, or about 140 of the same amino acids, or about 150 of the same amino acids, or about 50-80 of the same amino acids, or about 150-325 of the same amino acids as any of any of SEQ ID NO:3, 5, 7, 9, 11, 13, 15, 17, 19, 21, 23, 24, 25, 27, 29, 31, 33, 35, or 36 polypeptides. The identical amino acids can be distributed throughout the nucleic acid, and need not be contiguous.

The transcription factor polypeptides have about at least 40% sequence identity, at least about 50% sequence identity, at least 50% sequence identity, at least about 60% sequence identity, at least 70% sequence identity, at least about 80% sequence identity, at least 90% sequence identity, at least about 95% sequence identity, or 40-95% sequence identity, or 50-95% sequence identity, or 60-90% sequence identity, or 90-95% sequence identity, or 90-99% sequence identity, or 95-97% sequence identity, or 98-99% sequence identity, or 100% sequence identity with any of the SEQ ID NO:3, 5, 7, 9, 11, 13, 15, 17, 19, 21, 23, 24, 25, 27, 29, 31, 33, 35, or 36 polypeptides.

Note that if a value of a variable that is necessarily an integer, e.g., the number of nucleotides or amino acids in a nucleic acid or protein, is described as a range, e.g., or 90-99% sequence identity, what is meant is that the value can be any integer between 90 and 99 inclusive, i.e., 90-99% sequence identity means any of 90, 91, 92, 93, 94, 95, 96, 97, 98 or 99% sequence identity.

Plants Modified to Contain Transcription Factors and/or Promoter Sequences

In order to engineer plants with desired quantities of glucomannan, one of skill in the art can introduce transcription factors or nucleic acids encoding transcription factors into the plants. Such transcription factors can bind to the promoter regions of the CSLA9 gene and stimulate expression of the CSLA9 protein, which can synthesize glucomannan. Any of the MYB46, ANAC041, bZIP1, and related nucleic acid sequences described herein can be incorporated into the expression cassettes, plants and seeds described herein. Such transcription factors can bind to promoter regions of the CSLA9 gene and stimulate the expression of the CSLA9 protein.

In some embodiments, one of skill in the art could inject transcription factors or nucleic acids encoding such transcription factors into young plants, or into selected regions of plants. Alternatively, one of skill in the art can generate genetically-modified plants that contain nucleic acids encoding transcription factors within their somatic and/or germ cells. For example, any of the transcription factors nucleic acids described herein can be operably linked to a selected promoter (e.g., a heterologous promoter), to generate an expression cassette that can be used to generate transgenic plants and/or seeds. Examples of transcription factor coding regions that can be used in such expression cassettes include any of the following SEQ ID NOs: 2, 4, 6, 8, 10, 12, 14, 16, 18, 20, 22, 26, 28, 30, 32, 34, or any combination thereof. The expression cassettes can be introduced into plants to increase the glucomannan content of the plant's tissues.

In addition, those of skill in the art can use the CSLA9 promoter sequences to drive expression of other coding regions of interest, for example, by genetically modifying a plant to contain a nucleic acid segment that includes the CSLA9 promoter upstream of the coding region of interest. Such a CSLA9 promoter operably linked to a coding region of interest can be part of an expression cassette for expressing any coding region of interest. To facilitate expression of a coding region of interest, a separate expression cassette can be made that encodes any of the MYB46, ANAC041, bZIP1, and related transcription factors. Expression of any of these transcription factors can increase the expression of the selected coding region, because the MYB46, ANAC041, bZIP1, and related transcription factors will bind to the CSLA9 promoter and promote such transcription. The genetic modifications involved can be accomplished by procedures available in the art. For example, one of skill in the art can prepare an expression cassette or expression vector that can express one or more encoded transcription factors and separately construct an expression vector containing the CSLA9 promoter operably linked to a coding region of interest. In general, a nucleic acid segment encoding a CSLA9 promoter described herein can be operably linked to a selected coding region of interest, for example, by inserting the CSLA9 promoter nucleic acid segment upstream of a selected coding region nucleic acid.

Plant cells can be transformed by the expression cassettes or expression vector, and whole plants (and their seeds) can be generated from the plant cells that were successfully transformed with the promoter and/or transcription factor nucleic acids. Some procedures for making such genetically modified plants and their seeds are described in more detail below.

Heterologous Promoters:

The transcription factor nucleic acids (e.g., any of those encoding MYB46, bZIP1, ANAC041, or related proteins) can be operably linked to a promoter, such as a heterologous promoter, which provides for expression of mRNA encoding the transcription factors. The heterologous promoter employed is typically a promoter functional in plants and/or seeds, and can be a promoter functional during plant growth and development. The heterologous promoter is a promoter that is not operably linked to MYB46, bZIP1, ANAC041, or a related protein in nature. A transcription factor nucleic acid is operably linked to the promoter when it is located downstream from the promoter, so that the promoter is configured to express the transcription factor.

Promoters regulate gene expression. Promoter regions are typically found in the flanking DNA upstream from the coding sequence in both prokaryotic and eukaryotic cells. A promoter sequence provides for regulation of transcription of the downstream gene sequence and typically includes from about 50 to about 2,000 nucleotide base pairs. Promoter sequences can also contain regulatory sequences such as enhancer sequences that can influence the level of gene expression. Some isolated promoter sequences can provide for gene expression of heterologous DNAs, that is a DNA different from the native or homologous DNA.

Promoter sequences can be strong or weak, or inducible. A strong promoter provides for a high level of gene expression, whereas a weak promoter provides for a very low level of gene expression. An inducible promoter is a promoter that provides for the turning on and off of gene expression in response to an exogenously added agent, or to an environmental or developmental stimulus. For example, expression can be stimulated from an inducible promoter by factors such as alcohol, acetaldehyde, antibiotics (e.g., tetracycline), steroids, metals and other compounds. An environmentally inducible promoter can induce expression of a gene in response to environmental stimuli such as drought, cold, heat, longer exposure to light, or shorter exposure to light. A bacterial promoter such as the $P_{tac}$ promoter can be induced to vary levels of gene expression depending on the level of isothiopropylgalactoside added to the transformed cells. Steroid inducible promoters have also been employed in plants. Dexamethasone-inducible promoters are activated by introduction of dexamethasone to a cell, tissue, cell culture, or tissue culture. The alc promoter system from the filamentous fungi *Aspergillus nidulans* can be induced by alcohol (e.g., ethanol) or acetaldehyde (see, e.g., Schaarschmidt et al., Plant & Cell Physiol 45(11): 1566-77 (2004). The nopaline synthase (nos) promoter is inducible by hydrogen peroxide and/or methyl jasmonate (see, e.g., Sai & An, *Plant Physiol.* 109(4): 1191-97 (1995)).

Promoters can also provide for tissue specific or developmental regulation. In some embodiments, an isolated promoter sequence that is a strong promoter for heterologous DNAs is advantageous because it provides for a sufficient level of gene expression for easy detection and selection of transformed cells and provides for a high level of gene expression when desired.

Expression cassettes encoding a transcription factor can include, but are not limited to, a plant promoter such as the CaMV 35S promoter (Odell et al., *Nature.* 313:810-812 (1985)), or others such as CaMV 19S (Lawton et al., *Plant Molecular Biology.* 9:315-324 (1987)), nos (Ebert et al., *Proc. Natl. Acad. Sci. USA.* 84:5745-5749 (1987)), Adh1 (Walker et al., *Proc. Natl. Acad. Sci. USA.* 84:6624-6628 (1987)), sucrose synthase (Yang et al., *Proc. Natl. Acad. Sci. USA.* 87:4144-4148 (1990)), α-tubulin, ubiquitin, actin (Wang et al., *Mol. Cell. Biol.* 12:3399 (1992)), cab (Sullivan et al., *Mol. Gen. Genet.* 215:431 (1989)), PEPCase (Hudspeth et al., *Plant Molecular Biology.* 12:579-589 (1989)), GAL4/UAS (Brand & Perrimon, Development 118: 401-15

(1993); and/or those associated with the R gene complex (Chandler et al., *The Plant Cell*. 1:1175-1183 (1989)). Further suitable promoters include the poplar xylem-specific secondary cell wall specific cellulose synthase 8 promoter, cauliflower mosaic virus promoter, the Z10 promoter from a gene encoding a 10 kD zein protein, a Z27 promoter from a gene encoding a 27 kD zein protein, inducible promoters, such as the light inducible promoter derived from the pea rbcS gene (Coruzzi et al., *EMBO J.* 3:1671 (1971)) and the actin promoter from rice (McElroy et al., *The Plant Cell.* 2:163-171 (1990)). Seed specific promoters, such as the phaseolin promoter from beans, may also be used (Sengupta-Gopalan, *Proc. Natl. Acad. Sci. USA*. 83:3320-3324 (1985). Other promoters useful in the practice of the invention are available to those of skill in the art.

Alternatively, novel tissue specific promoter sequences may be employed for the expression of the transcription factor(s). cDNA clones from a particular tissue can be isolated and those clones that are expressed specifically in a tissue of interest are identified, for example, using Northern blotting, quantitative PCR and other available methods. In some embodiments, the gene isolated is not present in a high copy number, but is relatively abundant in specific tissues. The promoter and control elements of corresponding genomic clones can then be identified, isolated and utilized using techniques well known to those of skill in the art.

A transcription factor nucleic acid can be combined with a selected promoter by available methods to yield an expression cassette, for example, as described in Sambrook et al. (MOLECULAR CLONING: A LABORATORY MANUAL. Second Edition (Cold Spring Harbor, N.Y.: Cold Spring Harbor Press (1989); MOLECULAR CLONING: A LABORATORY MANUAL. Third Edition (Cold Spring Harbor, N.Y.: Cold Spring Harbor Press (2000)). Briefly, a plasmid containing a promoter such as the 35S CaMV promoter can be constructed as described in Jefferson (*Plant Molecular Biology Reporter* 5:387-405 (1987)) or obtained from Clontech Lab in Palo Alto, Calif. (e.g., pBI121 or pBI221). Typically, these plasmids are constructed to have multiple cloning sites having specificity for different restriction enzymes downstream from the promoter. The transcription factor nucleic acids can be subcloned downstream from the promoter using restriction enzymes and positioned to ensure that the transcription factor DNA is inserted in proper orientation with respect to the promoter so that the DNA can be expressed. Once the transcription factor nucleic acid is operably linked to a promoter, the expression cassette so formed can be subcloned into a plasmid or other vector (e.g., an expression vector).

In some embodiments, a cDNA encoding a protein with at least 60% sequence identity to any of SEQ ID NO:3, 5, 7, 9, 11, 13, 15, 17, 19, 21, 23, 24, 25, 27, 29, 31, 33, 35, or 36 is isolated from a selected plant species, and operably linked to a heterologous promoter. The cDNA can be a transcription factor with at least 60% sequence identity to any of SEQ ID NO:3, 5, 7, 9, 11, 13, 15, 17, 19, 21, 23, 24, 25, 27, 29, 31, 33, or 35, or an enzyme with at least 60% sequence identity to SEQ ID NO:36. The a cDNA encoding a protein can, for example, be an *Arabidopsis*, corn, sugar beets, soybean, sugar cane, potato, grasses (e.g., *miscanthus*, switchgrass, and the like), as well as trees such as poplar, aspen, willow, and the like. In other embodiments, cDNA from other species that encode a transcription factor proteins are isolated from selected plant tissues, or a nucleic acid encoding a mutant or modified transcription factor protein is prepared by available methods or as described herein. For example, the nucleic acid encoding a mutant or modified transcription factor protein can be any nucleic acid with a coding region that hybridizes to SEQ ID NO:2, 4, 6, 8, 10, 12, 14, 16, 18, 20, 22, 26, 28, 30, 32, or 34 that can promote expression of a glucomannan synthase enzyme. Using restriction endonucleases, the entire coding sequence for the transcription factor can be subcloned downstream of the promoter in a 5' to 3' sense orientation.

Targeting Sequences:

Additionally, expression cassettes can be constructed and employed to target the transcription factors or polypeptides of interest to intracellular compartments within plant cells, or to target the transcription factors or polypeptides of interest for extracellular secretion.

In general, transcription factors bind to plant chromosomal DNA within the nucleus. Therefore, the transcription factor is preferably targeted to the nucleus and not directed to other plant organelles or the extracellular environment. However, there may be instances where is it desirable to secrete or sequester the transcription factor within organelles or storage vesicles (e.g., to facilitate isolation and/or purification of the transcription factor protein). Similarly, polypeptides of interest can be encoded within expression cassettes containing a CSLA9 promoter described herein, and it may be desirable to target those polypeptides to various intracellular compartments or to the extracellular environment. Therefore, the invention contemplates targeting the transcription factor(s) as well as polypeptides of interest to various intracellular and extracellular locations.

A nuclear localization signal or sequence is an amino acid sequences that 'tags' a protein for import into the cell nucleus by nuclear transport. Transcription factors may naturally have such a nuclear localization signal or sequence. Alternatively, a nuclear localization signal or sequence can be operably linked to the transcription factor sequence. Transit peptides act by facilitating the transport of proteins through intracellular membranes, e.g., vacuole, vesicle, plastid and mitochondrial membranes, whereas signal peptides direct proteins through the extracellular membrane. Polypeptides of interest can be operably linked to nuclear localization signals/sequences, to transit peptides or to signal peptides.

Targeting to selected intracellular regions can generally be achieved by joining a DNA sequence encoding a nuclear localization sequence, or a transit peptide or a signal peptide sequence to the coding sequence of the transcription factor or the polypeptide of interest. The resultant nuclear localization sequence (or transit, or signal, peptide) will transport the transcription factor or protein to a particular intracellular (or extracellular) destination. Such sequences (nuclear localization sequences, transit peptides or signal peptides) may be post-translationally removed by cellular enzymes. By facilitating transport of the protein into compartments inside or outside the cell, these sequences can increase the accumulation of a particular gene product in a particular location.

3' Sequences:

The expression cassette can also optionally include 3' nontranslated plant regulatory DNA sequences that act as a signal to terminate transcription and allow for the polyadenylation of the resultant mRNA. The 3' nontranslated regulatory DNA sequence preferably includes from about 300 to 1,000 nucleotide base pairs and contains plant transcriptional and translational termination sequences. For example, 3' elements that can be used include those derived from the nopaline synthase gene of *Agrobacterium tumefaciens* (Bevan et al., *Nucleic Acid Research*. 11:369-385 (1983)), or the terminator sequences for the T7 transcript from the octopine synthase gene of *Agrobacterium tumefaciens*, and/ or the 3' end of the protease inhibitor I or II genes from potato or tomato. Other 3' elements known to those of skill in the art can also be employed. These 3' nontranslated regulatory sequences can be obtained as described in An (*Methods in Enzymology.* 153:292 (1987)). Many such 3' nontranslated regulatory sequences are already present in plasmids available from commercial sources such as Clontech, Palo Alto, Calif. The 3' nontranslated regulatory sequences can be operably linked to the 3' terminus of the transcription factor or other polypeptide nucleic acids by standard methods.

Selectable and Screenable Marker Sequences:

In order to improve identification of transformants, a selectable or screenable marker gene can be employed with the expressible transcription factor or other polypeptide nucleic acids. "Marker genes" are genes that impart a distinct phenotype to cells expressing the marker gene and thus allow such transformed cells to be distinguished from cells that do not have the marker. Such genes may encode either a selectable or screenable marker, depending on whether the marker confers a trait which one can 'select' for the marker by chemical means, i.e., through the use of a selective agent (e.g., a herbicide, antibiotic, or the like), or whether marker is simply a trait that one can identify through observation or testing, i.e., by 'screening' (e.g., the R-locus trait). Many examples of suitable marker genes are known to the art and can be employed in the practice of the invention.

Included within the terms selectable or screenable marker genes are also genes which encode a "secretable marker" whose secretion can be detected as a means of identifying or selecting for transformed cells. Examples include markers which encode a secretable antigen that can be identified by antibody interaction, or secretable enzymes that can be detected by their catalytic activity. Secretable proteins fall into a number of classes, including small, diffusible proteins detectable, e.g., by ELISA; and proteins that are inserted or trapped in the cell wall (e.g., proteins that include a leader sequence such as that found in the expression unit of extensin or tobacco PR-S).

With regard to selectable secretable markers, the use of a gene that encodes a polypeptide that becomes sequestered in the cell wall, where the polypeptide includes a unique epitope may be advantageous. Such a secreted antigen marker can employ an epitope sequence that would provide a low background in plant tissue, a promoter-leader sequence that imparts efficient expression and targeting across the plasma membrane, and can produce protein that is bound in the cell wall and yet is accessible to antibodies. A normally secreted wall protein modified to include a unique epitope would satisfy such requirements.

Examples of marker proteins suitable for modification in this manner include extensin or hydroxyproline rich glycoprotein (HPRG). For example, the maize HPRG (Stiefel et al., *The Plant Cell.* 2:785-793 (1990)) is well characterized in terms of molecular biology, expression, and protein structure and therefore can readily be employed. However, any one of a variety of extensins and/or glycine-rich wall proteins (Keller et al., *EMBO J.* 8:1309-1314 (1989)) could be modified by the addition of an antigenic site to create a screenable marker.

Numerous other possible selectable and/or screenable marker genes will be apparent to those of skill in the art in addition to the one set forth herein. Therefore, it will be understood that the following discussion is exemplary rather than exhaustive. In light of the techniques disclosed herein and the general recombinant techniques that are known in the art, the present invention readily allows the introduction of any gene, including marker genes, into a recipient cell to generate a transformed plant cell, e.g., a monocot cell or dicot cell.

Possible selectable markers for use in connection with expression cassettes include, but are not limited to, a neo gene (Potrykus et al., *Mol. Gen. Genet.* 199:183-188 (1985)) which codes for kanamycin resistance and can be selected for using kanamycin, G418, and the like; a bar gene which codes for bialaphos resistance; a gene which encodes an altered EPSP synthase protein (Hinchee et al., *Bio/Technology.* 6:915-922 (1988)) thus conferring glyphosate resistance; a nitrilase gene such as bxn from *Klebsiella ozaenae* which confers resistance to bromoxynil (Stalker et al., *Science.* 242:419-423 (1988)); a mutant acetolactate synthase gene (ALS) which confers resistance to imidazolinone, sulfonylurea or other ALS-inhibiting chemicals (European Patent Application 154,204 (1985)); a methotrexate-resistant DHFR gene (Thillet et al., *J. Biol. Chem.* 263:12500-12508 (1988)); a dalapon dehalogenase gene that confers resistance to the herbicide dalapon; or a mutated anthranilate synthase gene that confers resistance to 5-methyl tryptophan. Where a mutant EPSP synthase gene is employed, additional benefit may be realized through the incorporation of a suitable chloroplast transit peptide, CTP (European Patent Application 0 218 571 (1987)).

Another selectable marker gene capable of being used in for selection of transformants is the gene that encodes the enzyme phosphinothricin acetyltransferase, such as the bar gene from *Streptomyces hygroscopicus* or the pat gene from *Streptomyces viridochromogenes* (U.S. Pat. No. 5,550,318). The enzyme phosphinothricin acetyl transferase (PAT) inactivates the active ingredient in the herbicide bialaphos, phosphinothricin (PPT). PPT inhibits glutamine synthetase, (Murakami et al., *Mol. Gen. Genet.* 205:42-50 (1986); Twell et al., *Plant Physiol.* 91:1270-1274 (1989)) causing rapid accumulation of ammonia and cell death. The success in using this selective system in conjunction with monocots was surprising because of the major difficulties that have been reported in transformation of cereals (Potrykus, *Trends Biotech.* 7:269-273 (1989)).

Screenable markers that may be employed include, but are not limited to, a β-glucuronidase or uidA gene (GUS) that encodes an enzyme for which various chromogenic substrates are known; an R-locus gene, which encodes a product that regulates the production of anthocyanin pigments (red color) in plant tissues (Dellaporta et al., In: *Chromosome Structure and Function: Impact of New Concepts,* 18$^{th}$ Stadler Genetics Symposium, J. P. Gustafson and R. Appels, eds. (New York: Plenum Press) pp. 263-282 (1988)); a β-lactamase gene (Sutcliffe, *Proc. Natl. Acad. Sci. USA.* 75:3737-3741 (1978)), which encodes an enzyme for which various chromogenic substrates are known (e.g., PADAC, a chromogenic cephalosporin); a xylE gene (Zukowsky et al., *Proc. Natl. Acad. Sci. USA.* 80:1101 (1983)) which encodes a catechol dioxygenase that can convert chromogenic catechols; an α-amylase gene (Ikuta et al., *Bio/technology* 8:241-242 (1990)); a tyrosinase gene (Katz et al., *J. Gen. Microbiol.* 129:2703-2714 (1983)) which encodes an enzyme capable of oxidizing tyrosine to DOPA and dopaquinone which in turn condenses to form the easily detectable compound melanin; a β-galactosidase gene, which encodes an enzyme for which there are chromogenic substrates; a luciferase (lux) gene (Ow et al., *Science.* 234:856-859.1986), which allows for bioluminescence detection; or an aequorin gene (Prasher et al., *Biochem. Biophys. Res. Comm.* 126:1259-1268 (1985)), which may be employed in calcium-sensitive bioluminescence detection, or a green or yellow fluorescent protein gene (Niedz et al., *Plant Cell Reports.* 14:403 (1995)).

For example, genes from the maize R gene complex can be used as screenable markers. The R gene complex in maize encodes a protein that acts to regulate the production of anthocyanin pigments in most seed and plant tissue. Maize strains can have one, or as many as four, R alleles that combine to regulate pigmentation in a developmental and tissue specific manner. A gene from the R gene complex does not harm the transformed cells. Thus, an R gene introduced into such cells will cause the expression of a red pigment and, if stably incorporated, can be visually scored as a red sector. If a maize line carries dominant alleles for genes encoding the enzymatic intermediates in the anthocyanin biosynthetic pathway (C2, A1, A2, Bz1 and Bz2), but carries a recessive allele at the R locus, transformation of any cell from that line with R will result in red pigment formation. Exemplary lines include Wisconsin 22 that contains the rg-Stadler allele and TR112, a K55 derivative that is r-g, b, Pl. Alternatively any genotype of maize can be utilized if the C1 and R alleles are introduced together.

The R gene regulatory regions can be employed in chimeric constructs in order to provide mechanisms for controlling the expression of chimeric genes. More diversity of phenotypic expression is known at the R locus than at any other locus (Coe et al., in *Corn and Corn Improvement*, eds. Sprague, G. F. & Dudley, J. W. (Am. Soc. Agron., Madison, Wis.), pp. 81-258 (1988)). It is contemplated that regulatory regions obtained from regions 5' to the structural R gene can be useful in directing the expression of genes, e.g., insect resistance, drought resistance, herbicide tolerance or other protein coding regions. For the purposes of the present invention, it is believed that any of the various R gene family members may be successfully employed (e.g., P, S, Lc, etc.). However, one that can be used is Sn (particularly Sn:bol3). Sn is a dominant member of the R gene complex and is functionally similar to the R and B loci in that Sn controls the tissue specific deposition of anthocyanin pigments in certain seedling and plant cells, therefore, its phenotype is similar to R.

A further screenable marker contemplated for use in the present invention is firefly luciferase, encoded by the lux gene. The presence of the lux gene in transformed cells may be detected using, for example, X-ray film, scintillation counting, fluorescent spectrophotometry, low-light video cameras, photon counting cameras or multiwell luminometry. It is also envisioned that this system may be developed for population screening for bioluminescence, such as on tissue culture plates, or even for whole plant screening.

Other Optional Sequences:

An expression cassette of the invention can also further comprise plasmid DNA. Plasmid vectors include additional DNA sequences that provide for easy selection, amplification, and transformation of the expression cassette in prokaryotic and eukaryotic cells, e.g., pUC-derived vectors such as pUC8, pUC9, pUC18, pUC19, pUC23, pUC119, and pUC120, pSK-derived vectors, pGEM-derived vectors, pSP-derived vectors, or pBS-derived vectors. The additional DNA sequences include origins of replication to provide for autonomous replication of the vector, additional selectable marker genes (e.g., antibiotic or herbicide resistance), unique multiple cloning sites providing for multiple sites to insert DNA sequences or genes encoded in the expression cassette and sequences that enhance transformation of prokaryotic and eukaryotic cells.

Another vector that is useful for expression in both plant and prokaryotic cells is the binary Ti plasmid (as disclosed in Schilperoort et al., U.S. Pat. No. 4,940,838) as exemplified by vector pGA582. This binary Ti plasmid vector has been previously characterized by An (*Methods in Enzymology.* 153:292 (1987)) and is available from Dr. An. This binary Ti vector can be replicated in prokaryotic bacteria such as *E. coli* and *Agrobacterium*. The *Agrobacterium* plasmid vectors can be used to transfer the expression cassette to dicot plant cells, and under certain conditions to monocot cells, such as rice cells. The binary Ti vectors preferably include the nopaline T DNA right and left borders to provide for efficient plant cell transformation, a selectable marker gene, unique multiple cloning sites in the T border regions, the colE1 replication of origin and a wide host range replicon. The binary Ti vectors carrying an expression cassette of the invention can be used to transform both prokaryotic and eukaryotic cells, but is preferably used to transform dicot plant cells.

In Vitro Screening of Expression Cassettes:

Once the expression cassette is constructed and subcloned into a suitable plasmid, it can be screened for the ability to express the transcription factor or the polypeptide of interest. For example, an expression cassette encoding a transcription factor can be screened to ascertain whether it can promote expression of a glucomannan synthase by methods described herein or other available methods for detecting mannan. An expression cassette encoding other polypeptides of interest can be screened to ascertain whether it can promote expression of the polypeptide, for example, by immunological detection of the polypeptide of interest, by detection of the activity of the polypeptide, by hybridization or PCR detection of transcripts encoding the polypeptide, or by other procedures available to those of skill in the art.

DNA Delivery of the DNA Molecules into Host Cells:

Transcription factor or other polypeptide encoding nucleic acids can be introduced into host cells by a variety of methods. For example, a preselected cDNA encoding the selected transcription factor or other polypeptide can be introduced into a recipient cell to create a transformed cell by available procedures. The frequency of occurrence of cells taking up exogenous (foreign) DNA may be low. Moreover, it is most likely that not all recipient cells receiving DNA segments or sequences will result in a transformed cell wherein the DNA is stably integrated into the plant genome and/or expressed. Some may show only initial and transient gene expression. However, certain cells from virtually any dicot or monocot species may be stably transformed, and these cells can be regenerated into transgenic plants, through the application of the techniques disclosed herein.

Another aspect of the invention is an isolated plant or plant cell that has one of the transcription factors or CSLA9 promoters introduced into the cell, e.g., as a nucleic acid encoding the transcription factor or promoter, or as a protein product. The plant can be a monocotyledon or a dicotyledon. Another aspect of the invention includes plant cells (e.g., embryonic cells or other cell lines) that can regenerate fertile transgenic plants and/or seeds. The cells can be derived from either monocotyledons or dicotyledons. Suitable examples of plant species include wheat, rice, *Arabidopsis*, tobacco, maize, soybean, corn, grasses (e.g., *miscanthus*, switchgrass, and the like), as well as trees such as poplar, aspen, willow, and the like. In some embodiments, the plant or cell is a monocotyledon plant or cell. For example, the plant or cell can be a maize plant or cell. The cell(s) may be in a suspension cell culture or may be in an intact plant part, such as an immature embryo, or in a specialized plant tissue, such as callus, such as Type I or Type II callus.

Transformation of the cells of the plant tissue source can be conducted by any one of a number of methods known to those of skill in the art. Examples are: Transformation by direct DNA transfer into plant cells by electroporation (U.S. Pat. No. 5,384,253 and U.S. Pat. No. 5,472,869, Dekeyser et al., *The Plant Cell*. 2:591-602 (1990)); direct DNA transfer to plant cells by PEG precipitation (Hayashimoto et al., *Plant Physiol*. 93:857-863 (1990)); direct DNA transfer to plant cells by microprojectile bombardment (McCabe et al., *Bio/Technology*. 6:923-926 (1988); Gordon-Kamm et al., *The Plant Cell*. 2:603-618 (1990); U.S. Pat. No. 5,489,520; U.S. Pat. No. 5,538,877; and U.S. Pat. No. 5,538,880) and DNA transfer to plant cells via infection with *Agrobacterium*. Methods such as microprojectile bombardment or electroporation can be carried out with "naked" DNA where the expression cassette may be simply carried on any *E. coli*-derived plasmid cloning vector. In the case of viral vectors, it is desirable that the system retain replication functions, but lack functions for disease induction.

One method for dicot transformation, for example, involves infection of plant cells with *Agrobacterium tumefaciens* using the leaf-disk protocol (Horsch et al., *Science* 227:1229-1231 (1985). Monocots such as *Zea mays* can be transformed via microprojectile bombardment of embryogenic callus tissue or immature embryos, or by electroporation following partial enzymatic degradation of the cell wall with a pectinase-containing enzyme (U.S. Pat. No. 5,384,253; and U.S. Pat. No. 5,472,869). For example, embryogenic cell lines derived from immature *Zea mays* embryos can be transformed by accelerated particle treatment as described by Gordon-Kamm et al. (*The Plant Cell*. 2:603-618 (1990)) or U.S. Pat. No. 5,489,520; U.S. Pat. No. 5,538,877 and U.S. Pat. No. 5,538,880, cited above. Excised immature embryos can also be used as the target for transformation prior to tissue culture induction, selection and regeneration as described in U.S. application Ser. No. 08/112,245 and PCT publication WO 95/06128. Furthermore, methods for transformation of monocotyledonous plants utilizing *Agrobacterium tumefaciens* have been described by Hiei et al. (European Patent 0 604 662, 1994) and Saito et al. (European Patent 0 672 752, 1995).

Methods such as microprojectile bombardment or electroporation are carried out with "naked" DNA where the expression cassette may be simply carried on any *E. coli*-derived plasmid cloning vector. In the case of viral vectors, it is desirable that the system retain replication functions, but eliminate functions for disease induction.

The choice of plant tissue source for transformation will depend on the nature of the host plant and the transformation protocol. Useful tissue sources include callus, suspension culture cells, protoplasts, leaf segments, stem segments, tassels, pollen, embryos, hypocotyls, tuber segments, meristematic regions, and the like. The tissue source is selected and transformed so that it retains the ability to regenerate whole, fertile plants following transformation, i.e., contains totipotent cells. Type I or Type II embryonic maize callus and immature embryos are preferred *Zea mays* tissue sources. Selection of tissue sources for transformation of monocots is described in detail in U.S. application Ser. No. 08/112,245 and PCT publication WO 95/06128.

The transformation is carried out under conditions directed to the plant tissue of choice. The plant cells or tissue are exposed to the DNA or RNA carrying the transcription factor nucleic acids for an effective period of time. This may range from a less than one second pulse of electricity for electroporation to a 2-3 day co-cultivation in the presence of plasmid-bearing *Agrobacterium* cells. Buffers and media used will also vary with the plant tissue source and transformation protocol. Many transformation protocols employ a feeder layer of suspended culture cells (tobacco or Black Mexican Sweet corn, for example) on the surface of solid media plates, separated by a sterile filter paper disk from the plant cells or tissues being transformed.

Electroporation:

Where one wishes to introduce DNA by means of electroporation, it is contemplated that the method of Krzyzek et al. (U.S. Pat. No. 5,384,253) may be advantageous. In this method, certain cell wall-degrading enzymes, such as pectin-degrading enzymes, are employed to render the target recipient cells more susceptible to transformation by electroporation than untreated cells. Alternatively, recipient cells can be made more susceptible to transformation, by mechanical wounding.

To effect transformation by electroporation, one may employ either friable tissues such as a suspension cell cultures, or embryogenic callus, or alternatively, one may transform immature embryos or other organized tissues directly. The cell walls of the preselected cells or organs can be partially degraded by exposing them to pectin-degrading enzymes (pectinases or pectolyases) or mechanically wounding them in a controlled manner. Such cells would then be receptive to DNA uptake by electroporation, which may be carried out at this stage, and transformed cells then identified by a suitable selection or screening protocol dependent on the nature of the newly incorporated DNA.

Microprojectile Bombardment:

A further advantageous method for delivering transforming DNA segments to plant cells is microprojectile bombardment. In this method, microparticles may be coated with DNA and delivered into cells by a propelling force. Exemplary particles include those comprised of tungsten, gold, platinum, and the like.

It is contemplated that in some instances DNA precipitation onto metal particles would not be necessary for DNA delivery to a recipient cell using microprojectile bombardment. For example, non-embryogenic Black Mexican Sweet maize cells can be bombarded with intact cells of the bacteria *E. coli* or *Agrobacterium tumefaciens* containing plasmids with either the β-glucuronidase or bar gene engineered for expression in maize. Bacteria can be inactivated by ethanol dehydration prior to bombardment. A low level of transient expression of the 0-glucuronidase gene may be observed 24-48 hours following DNA delivery. In addition, stable transformants containing the bar gene can be recovered following bombardment with either *E. coli* or *Agrobacterium tumefaciens* cells. It is contemplated that particles may contain DNA rather than be coated with DNA. The particles may increase the level of DNA delivery but may not be, in and of themselves, necessary to introduce DNA into plant cells.

An advantage of microprojectile bombardment, in addition to it being an effective means of reproducibly stably transforming monocots, is that the isolation of protoplasts (Christou et al., *PNAS*. 84:3962-3966 (1987)), the formation of partially degraded cells, or the susceptibility to *Agrobacterium* infection is not required. An illustrative embodiment of a method for delivering DNA into maize cells by acceleration is a Biolistics Particle Delivery System, which can be used to propel particles coated with DNA or cells through a screen, such as a stainless steel or Nytex screen, onto a filter surface covered with maize cells cultured in suspension (Gordon-Kamm et al., *The Plant Cell*. 2:603-618 (1990)).

The screen disperses the particles so that they are not delivered to the recipient cells in large aggregates. It is believed that a screen intervening between the projectile apparatus and the cells to be bombarded reduces the size of projectile aggregate and may contribute to a higher frequency of transformation, by reducing damage inflicted on the recipient cells by an aggregated projectile.

For bombardment, cells in suspension are preferably concentrated on filters or solid culture medium. Alternatively, immature embryos or other target cells may be arranged on solid culture medium. The cells to be bombarded are positioned at an appropriate distance below the macroprojectile stopping plate. If desired, one or more screens are also positioned between the acceleration device and the cells to be bombarded. Through the use of such techniques one may obtain up to 1000 or more foci of cells transiently expressing a marker gene. The number of cells in a focus which express the exogenous gene product 48 hours post-bombardment often range from about 1 to 10 and average about 1 to 3.

In bombardment transformation, one may optimize the prebombardment culturing conditions and the bombardment parameters to yield the maximum numbers of stable transformants. Both the physical and biological parameters for bombardment can influence transformation frequency. Physical factors are those that involve manipulating the DNA/microprojectile precipitate or those that affect the path and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmid DNA.

One may wish to adjust various bombardment parameters in small scale studies to fully optimize the conditions and/or to adjust physical parameters such as gap distance, flight distance, tissue distance, and helium pressure. One may also minimize the trauma reduction factors (TRFs) by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. Execution of such routine adjustments will be known to those of skill in the art.

An Example of Production and Characterization of Stable Transgenic Maize:

After effecting delivery of a transcription factor nucleic acid (or other nucleic acid encoding a desirable polypeptide) to recipient cells by any of the methods discussed above, the transformed cells can be identified for further culturing and plant regeneration. As mentioned above, in order to improve the ability to identify transformants, one may employ a selectable or screenable marker gene as, or in addition to, the expressible transcription factor nucleic acids. In this case, one would then generally assay the potentially transformed cell population by exposing the cells to a selective agent or agents, or one would screen the cells for the desired marker gene trait.

Selection:

An exemplary embodiment of methods for identifying transformed cells involves exposing the bombarded cultures to a selective agent, such as a metabolic inhibitor, an antibiotic, herbicide or the like. Cells that have been transformed and have stably integrated a marker gene conferring resistance to the selective agent used, will grow and divide in culture. Sensitive cells will not be amenable to further culturing.

To use the bar-bialaphos or the EPSPS-glyphosate selective system, bombarded tissue is cultured for about 0-28 days on nonselective medium and subsequently transferred to medium containing from about 1-3 mg/l bialaphos or about 1-3 mM glyphosate, as appropriate. While ranges of about 1-3 mg/l bialaphos or about 1-3 mM glyphosate can be employed, it is proposed that ranges of at least about 0.1-50 mg/l bialaphos or at least about 0.1-50 mM glyphosate will find utility in the practice of the invention. Tissue can be placed on any porous, inert, solid or semi-solid support for bombardment, including but not limited to filters and solid culture medium. Bialaphos and glyphosate are provided as examples of agents suitable for selection of transformants, but the technique of this invention is not limited to them.

An example of a screenable marker trait is the red pigment produced under the control of the R-locus in maize. This pigment may be detected by culturing cells on a solid support containing nutrient media capable of supporting growth at this stage and selecting cells from colonies (visible aggregates of cells) that are pigmented. These cells may be cultured further, either in suspension or on solid media. The R-locus is useful for selection of transformants from bombarded immature embryos. In a similar fashion, the introduction of the C1 and B genes will result in pigmented cells and/or tissues.

The enzyme luciferase is also useful as a screenable marker in the context of the present invention. In the presence of the substrate luciferin, cells expressing luciferase emit light which can be detected on photographic or X-ray film, in a luminometer (or liquid scintillation counter), by devices that enhance night vision, or by a highly light sensitive video camera, such as a photon counting camera. All of these assays are nondestructive and transformed cells may be cultured further following identification. The photon counting camera is especially valuable as it allows one to identify specific cells or groups of cells which are expressing luciferase and manipulate those in real time.

It is further contemplated that combinations of screenable and selectable markers may be useful for identification of transformed cells. For example, selection with a growth inhibiting compound, such as bialaphos or glyphosate at concentrations below those that cause 100% inhibition followed by screening of growing tissue for expression of a screenable marker gene such as luciferase would allow one to recover transformants from cell or tissue types that are not amenable to selection alone. In an illustrative embodiment embryogenic Type II callus of Zea mays L. can be selected with sub-lethal levels of bialaphos. Slowly growing tissue was subsequently screened for expression of the luciferase gene and transformants can be identified.

Regeneration and Seed Production:

Cells that survive the exposure to the selective agent, or cells that have been scored positive in a screening assay, are cultured in media that supports regeneration of plants. One example of a growth regulator that can be used for such purposes is dicamba or 2,4-D. However, other growth regulators may be employed, including NAA, NAA+2,4-D or perhaps even picloram. Media improvement in these and like ways can facilitate the growth of cells at specific developmental stages. Tissue can be maintained on a basic media with growth regulators until sufficient tissue is available to begin plant regeneration efforts, or following repeated rounds of manual selection, until the morphology of the tissue is suitable for regeneration, at least two weeks, then transferred to media conducive to maturation of embryoids. Cultures are typically transferred every two weeks on this medium. Shoot development signals the time to transfer to medium lacking growth regulators.

The transformed cells, identified by selection or screening and cultured in an appropriate medium that supports regeneration, can then be allowed to mature into plants. Developing plantlets are transferred to soil-less plant growth mix, and hardened, e.g., in an environmentally controlled chamber at about 85% relative humidity, about 600 ppm $CO_2$, and at about 25-250 microeinsteins/sec·m$^2$ of light. Plants can be matured either in a growth chamber or greenhouse. Plants are regenerated from about 6 weeks to 10 months after a transformant is identified, depending on the initial tissue. During regeneration, cells are grown on solid media in tissue culture vessels. Illustrative embodiments of such vessels are petri dishes and Plant Con™. Regenerating plants can be grown at about 19° C. to 28° C. After the regenerating plants have reached the stage of shoot and root development, they may be transferred to a greenhouse for further growth and testing.

Mature plants are then obtained from cell lines that are known to express the trait. In some embodiments, the regenerated plants are self-pollinated. In addition, pollen obtained from the regenerated plants can be crossed to seed grown plants of agronomically important inbred lines. In some cases, pollen from plants of these inbred lines is used to pollinate regenerated plants. The trait is genetically characterized by evaluating the segregation of the trait in first and later generation progeny. The heritability and expression in plants of traits selected in tissue culture are of particular importance if the traits are to be commercially useful.

Regenerated plants can be repeatedly crossed to inbred plants in order to introgress the transcription factor nucleic acids into the genome of the inbred plants. This process is referred to as backcross conversion. When a sufficient number of crosses to the recurrent inbred parent have been completed in order to produce a product of the backcross conversion process that is substantially isogenic with the recurrent inbred parent except for the presence of the introduced transcription factor or other promoter-polypeptide encoding nucleic acids, the plant is self-pollinated at least once in order to produce a homozygous backcross converted inbred containing the transcription factor or other promoter-polypeptide nucleic acids. Progeny of these plants are true breeding.

Alternatively, seed from transformed monocot plants regenerated from transformed tissue cultures is grown in the field and self-pollinated to generate true breeding plants.

Seed from the fertile transgenic plants can then be evaluated for the presence and/or expression of the transcription factor or other polypeptide nucleic acids (or the encoded transcription factor or other polypeptide). Transgenic plant and/or seed tissue can be analyzed for transcription factor expression using standard methods such as SDS polyacrylamide gel electrophoresis, liquid chromatography (e.g., HPLC) or other means of detecting a product of transcription factor activity (e.g., increased glucomannan or heightened expression of a glucomannan synthase) or a product of the polypeptide of interest.

Once a transgenic seed expressing the transcription factor or other polypeptide sequence is identified, the seed can be used to develop true breeding plants. The true breeding plants are used to develop a line of plants that express the transcription factor, contain one of the glucomannan synthase promoters (e.g., a CSLA9 promoter) described herein and/or contain a nucleic acid encoding such a promoter linked to a polypeptide of interest, while still maintaining other desirable functional agronomic traits. Adding the trait of increased transcription factor or other polypeptide expression to the plant can be accomplished by back-crossing with this trait with plants that do not exhibit this trait and by studying the pattern of inheritance in segregating generations. Those plants expressing the target trait in a dominant fashion are preferably selected. Back-crossing is carried out by crossing the original fertile transgenic plants with a plant from an inbred line exhibiting desirable functional agronomic characteristics while not necessarily expressing the trait of expression of a transcription factor and/or other desired polypeptide in the plant. The resulting progeny are then crossed back to the parent that expresses the trait. The progeny from this cross will also segregate so that some of the progeny carry the trait and some do not. This back-crossing is repeated until an inbred line with the desirable functional agronomic traits, and with expression of the desired trait within the plant. Such expression of the increased expression of the transcription factor or other polypeptide in plant can be expressed in a dominant fashion.

Subsequent to back-crossing, the new transgenic plants can be evaluated for expression of the transcription factor or other polypeptide. For example, when the transcription factor is expressed the weight percent of glucomannan within the plant or within selected tissues of the plant is increased. Detection of increased glucomannan can be done, for example, by staining plant tissues for glucomannan or by observing whether the tensile strength of plant fibers is increased or otherwise modulated relative to a plant that does not contain the exogenously added transcription factor. The new transgenic plants can also be evaluated for a battery of functional agronomic characteristics such as lodging, kernel hardness, yield, resistance to disease and insect pests, drought resistance, and/or herbicide resistance.

Plants that may be improved by these methods (incorporation of nucleic acids encoding transcription factors) include but are not limited to fiber-containing plants, trees, flax, grains (maize, wheat, barley, oats, rice, sorghum, millet and rye), grasses (switchgrass, prairie grass, wheat grass, sudangrass, sorghum, straw-producing plants), softwood, hardwood and other woody plants (e.g., those used for paper production such as poplar species, pine species, and *eucalyptus*), oil and/or starch plants (canola, potatoes, lupins, sunflower and cottonseed), and forage plants (alfalfa, clover and fescue). In some embodiments the plant is a gymnosperm. Examples of plants useful for pulp and paper production include most pine species such as loblolly pine, Jack pine, Southern pine, *Radiata* pine, spruce, Douglas fir and others. Hardwoods that can be modified as described herein include aspen, poplar, *eucalyptus*, and others. Plants useful for making biofuels and ethanol include corn, grasses (e.g., *miscanthus*, switchgrass, and the like), as well as trees such as poplar, aspen, willow, and the like. Plants useful for generating dairy forage include legumes such as alfalfa, as well as forage grasses such as bromegrass, and bluestem.

Determination of Stably Transformed Plant Tissues:

To confirm the presence of the transcription factor or other promoter-polypeptide-encoding nucleic acids in the regenerating plants, or seeds or progeny derived from the regenerated plant, a variety of assays may be performed. Such assays include, for example, molecular biological assays available to those of skill in the art, such as Southern and Northern blotting and PCR; biochemical assays, such as detecting the presence of a protein product, e.g., by immunological means (ELISAs and Western blots) or by enzymatic function; plant part assays, such as leaf, seed or root assays; and also, by analyzing the phenotype of the whole regenerated plant.

Whereas DNA analysis techniques may be conducted using DNA isolated from any part of a plant, RNA may only be expressed in particular cells or tissue types and so RNA for analysis can be obtained from those tissues. PCR techniques may also be used for detection and quantification of RNA produced from introduced transcription factor nucleic acids. PCR also be used to reverse transcribe RNA into DNA, using enzymes such as reverse transcriptase, and then this DNA can be amplified through the use of conventional PCR techniques. Further information about the nature of the RNA product may be obtained by Northern blotting. This technique will demonstrate the presence of an RNA species and give information about the integrity of that RNA. The presence or absence of an RNA species can also be determined using dot or slot blot Northern hybridizations. These techniques are modifications of Northern blotting and also demonstrate the presence or absence of an RNA species.

While Southern blotting and PCR may be used to detect the transcription factor nucleic acid in question, they do not provide information as to whether the preselected DNA segment is being expressed. Expression may be evaluated by specifically identifying the protein products of the introduced transcription factor nucleic acids or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange, liquid chromatography or gel exclusion chromatography. The unique structures of individual proteins offer opportunities for use of specific antibodies to detect their presence in formats such as an ELISA assay. Combinations of approaches may be employed with even greater specificity such as Western blotting in which antibodies are used to locate individual gene products that have been separated by electrophoretic techniques. Additional techniques may be employed to absolutely confirm the identity of the transcription factor or other polypeptide such as evaluation by amino acid sequencing following purification. The Examples of this application also provide assay procedures for detecting and quantifying transcription factor or other polypeptide or enzyme activities. Other procedures may be additionally used.

The expression of a gene product can also be determined by evaluating the phenotypic results of its expression. These assays also may take many forms including but not limited to analyzing changes in the chemical composition, morphology, or physiological properties of the plant.

Definitions

As used herein, the terms "crop" and "crop plant" are used herein its broadest sense. The term includes, but is not limited to, any species of plant or alga edible by humans or used as a feed for animals or fish or marine animals, or consumed by humans, or used by humans, or viewed by humans (flowers) or any plant or alga used in industry or commerce or education, such as vegetable crop plants, fruit crop plants, fodder crop plants, fiber crop plants, and turf grass plants.

As used herein, the term "exogenous promoter" refers to a promoter in operable combination with a coding region wherein the promoter is not the promoter naturally associated with the coding region in the genome of an organism. The promoter which is naturally associated or linked to a coding region in the genome is referred to as the "endogenous promoter" for that coding region.

As used herein, the term "expression" when used in reference to a nucleic acid sequence, such as a coding region or protein, refers to the process of converting genetic information encoded in a coding region into RNA (e.g., mRNA, rRNA, tRNA, or snRNA) through "transcription" of a gene or expression cassette (i.e., via the enzymatic action of an RNA polymerase), and into protein where applicable (as when a coding region encodes a protein), through "translation" of mRNA. Gene expression can be regulated at many stages in the process. "Up-regulation" or "activation" or "increased expression" refers to regulation that increases the production of gene expression products (i.e., RNA or protein), while "down-regulation" or "repression" or "decreased expression" refers to regulation that decreases production. Molecules (e.g., transcription factors) that are involved in up-regulation or down-regulation can also be called "activators" and "repressors," respectively.

As used herein, the term "heterologous" when used in reference to a gene, promoter, or nucleic acid refers to a gene, promoter, or nucleic acid that has been manipulated in some way. For example, a heterologous nucleic acid or a heterologous promoter includes a nucleic acid or promoter from one species that is introduced into another species. A heterologous nucleic acid or promoter also includes a nucleic acid or promoter that is native to an organism but that has been altered in some way (e.g., placed in a different chromosomal location, mutated, added in multiple copies, linked to a non-native promoter or enhancer sequence, etc.). Heterologous genes may comprise plant gene sequences that comprise cDNA forms of a plant gene; the cDNA sequences may be expressed in either a sense (to produce mRNA) or anti-sense orientation (to produce an anti-sense RNA transcript that is complementary to the mRNA transcript). Heterologous coding regions can be distinguished from endogenous plant coding regions, for example, when the heterologous coding regions are joined to nucleotide sequences comprising regulatory elements such as promoters that are not found naturally associated with the coding region, or when the heterologous coding regions are associated with portions of a chromosome not found in nature (e.g., genes expressed in loci where the protein encoded by the coding region is not normally expressed). Similarly, heterologous promoters can be promoters that at linked to a coding region to which they are not linked in nature.

As used herein, "isolated" means a nucleic acid or polypeptide has been removed from its natural or native cell. Thus, the nucleic acid or polypeptide can be physically isolated from the cell or the nucleic acid or polypeptide can be present or maintained in another cell where it is not naturally present or synthesized.

As used herein, the terms "leaf" and "leaves" refer to a usually flat, green structure of a plant where photosynthesis and transpiration take place and attached to a stem or branch.

Mannan is a linear polymer of mannose residues, linked by β(1-4) linkages. Mannan synthase can make these β(1-4) linkages. For example, mannan can have the following structure.

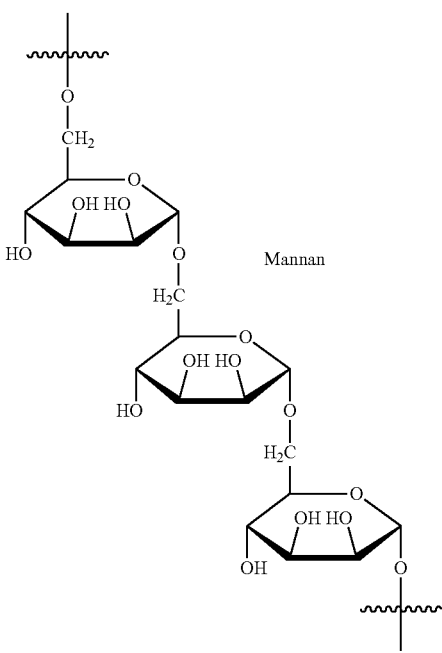

As used herein, a "native" nucleic acid or polypeptide means a DNA, RNA or amino acid sequence or segment that has not been manipulated in vitro, i.e., has not been isolated, purified, and/or amplified.

As used herein, the term "naturally linked" or "naturally located" when used in reference to the relative positions of nucleic acid sequences means that the nucleic acid sequences exist in nature in those positions.

As used herein, the terms "operably linked" or "in operable combination" or "in operable order" refers to the linkage of nucleic acids in such a manner that a nucleic acid molecule capable of directing the transcription of a given coding region and/or the synthesis of a desired protein molecule is produced. As used herein, the term also refers to the linkage of amino acid sequences in such a manner so that a functional protein is produced.

As used herein, the term "plant" is used in its broadest sense. It includes, but is not limited to, any species of grass (e.g. turf grass), sedge, rush, ornamental or decorative, crop or cereal, fodder or forage, fruit or vegetable, fruit plant or vegetable plant, woody, flower or tree. It is not meant to limit a plant to any particular structure. Such structures include, but are not limited to, stomata, a seed, a tiller, a sprig, a stolon, a plug, a rhizome, a shoot, a stem, a leaf, a flower petal, a fruit, etc.

As used herein, the terms "protein," "polypeptide," "peptide," "encoded product," "amino acid sequence," are used interchangeably to refer to compounds comprising amino acids joined via peptide bonds and. A "protein" encoded by a gene is not limited to the amino acid sequence encoded by the gene, but includes post-translational modifications of the protein. Where the term "amino acid sequence" is recited herein to refer to an amino acid sequence of a protein molecule, the term "amino acid sequence" and like terms, such as "polypeptide" or "protein" are not meant to limit the amino acid sequence to the complete, native amino acid sequence associated with the recited protein molecule. Furthermore, an "amino acid sequence" can be deduced from the nucleic acid sequence encoding the protein. The deduced amino acid sequence from a coding nucleic acid sequence includes sequences which are derived from the deduced amino acid sequence and modified by post-translational processing, where modifications include but not limited to glycosylation, hydroxylations, phosphorylations, and amino acid deletions, substitutions, and additions. Thus, an amino acid sequence comprising a deduced amino acid sequence can include post-translational modifications of the encoded and deduced amino acid sequence.

As used herein, "seed" refers to a ripened ovule, consisting of the embryo and a casing.

As used herein, "stem" refers to a main ascending axis of a plant.

As used herein, the term "transfection" refers to the introduction of foreign DNA into cells. Transfection may be accomplished by a variety of means known to the art including calcium phosphate-DNA co-precipitation, DEAE-dextran-mediated transfection, polybrene-mediated transfection, glass beads, electroporation, microinjection, liposome fusion, lipofection, protoplast fusion, viral infection, biolistics (i.e., particle bombardment), *Agrobacterium* infection, and the like. Methods of transfection are described herein.

As used herein, the term "transgene" refers to a foreign gene (e.g., an expression cassette) that is placed into an organism by the process of transfection.

As used herein, the term "vector" refers to nucleic acid molecules that transfer DNA segment(s). Transfer can be into a cell, cell-to-cell, etc.

As used herein, the term "wild-type" when made in reference to a nucleic acid or gene refers to a functional nucleic acid or gene common throughout an outbred population. As used herein, the term "wild-type" when made in reference to a gene product refers to a functional gene product common throughout an outbred population. A functional wild-type gene is that which is most frequently observed in a population and is thus arbitrarily designated the "normal" or "wild-type" form of the gene.

The following non-limiting Examples illustrate how aspects of the invention have been developed and can be made and used.

Example 1: Materials and Methods

This Example provides materials and methods used in development of the invention.

Plant Materials and Growth Conditions

*Arabidopsis thaliana*, ecotype Columbia (Col-0), was used in both the wild type and transgenic experiments. Plants were grown on soil in a growth chamber (16 h light/8 h dark) at 23° C. All experiments were performed at least three times and each experiment was performed using triplicate samples.

RNA Extraction and Evaluation of Transcript Abundance Using RT-PCR

Total RNA was extracted using Plant RNeasy extraction kit (Qiagen). For quantitative RT-PCR analysis, total RNA was treated with DNase I and used for first-strand cDNA synthesis using SuperScript II Reverse Transcriptase (Invitrogen). Real-time PCR was carried out using 1 μL of the reaction products as a template. Amplified DNA fragments were separated on 1% agarose gel and stained with ethidium bromide. Three biological replicates were used in the experiments. In other experiments, real-time PCR was performed using SYBR Premix Ex Taq™ (Takara) and ABI Prism 7900HT Sequence Detection System (ABI). The relative mRNA levels were determined by normalizing the PCR threshold cycle number of each gene to that of the ACT8 reference gene. Three biological replicates were used in the experiments.

Construction of Yeast One-Hybrid Mating Library

The REGIA (REgulatory Gene Initiative in *Arabidopsis*) Transcription Factor (TF) Open Reading Frame library was obtained from John Innes Genome Laboratory, Norwich, UK (Paz-Ares and the REGIA consortium, 2002). The library is composed of about 1,050 *E. coli* clones, each containing an individual *Arabidopsis* transcription factor inserted into a Gateway entry vector (either pENTR3c or pDONR201). Each transcription factor open reading frame from the REGIA library was fused to the yeast GAL4 activation domain (AD) in the yeast vector pDEST22 by performing the attL×attR (LR) in vitro recombination reaction (reaction kits were obtained from Invitrogen) as recommended by the supplier. The resulting pEXP22-TF vectors were transformed into *E. coli*, the TF-AD fusions were verified by nucleotide sequencing, and the vectors were introduced into *Saccharomyces cerevisiae* Y187 (MATα). The final "PRL TF-AD" library comprises 874 yeast clones, each carrying a different TF-AD fusion (see supplemental Table Si for listing of TFs included in the library).

Yeast One-Hybrid Screening

A Gateway compatible yeast one-hybrid system as described by Deplancke et al. (2004) was employed. In brief, the promoter of CSLA9 gene was cloned into Y1H reporter destination vector (pMW#2, Invitrogen) by gateway cloning and integrated into the genome of yeast strain YM4271. Bait strains were verified by genomic PCR using promoter-specific primers and subsequent sequencing of the PCR amplicons. After the self-activation test, promoter bait strains growing on the SD-His-Ura media containing 3-aminotriazole (3AT) at 40 mM or higher concentration were used. The promoter bait strains were then transformed with the AD-TF library (obtained from M. F. Thomashow, Michigan State University) and screened on the SD-His-Ura-Trp selection media containing 40 mM 3AT. Positive colonies were picked and tested for β-galactosidase expression as described (Deplancke et al. 2004). Yeast colony PCR was performed to identify interacting TF as described (Walhout and Vidal, 2001).

Protein Expression and Purification

MYB46 (At5g12870; SEQ ID NO:26), MYB83 (At3g08500), ANAC041 (At2g33480) and AtbZIP1 (At5g49450) were fused in frame with GST and expressed in *Escherichia coli* strain Rosetta gami (Novagen). The expression of the recombinant proteins were induced by culturing the *E. coli* cells for 16 h at 16° C. in LB medium supplemented with 0.1 mM IPTG (isopropyl β-D-thiogalactopyranoside). The recombinant proteins for electrophoretic mobility shift assay (EMSA) were purified using MagneGST™ Protein Purification System (Promega) according to the protocol provided in the kit.

Electrophoretic Mobility Shift Assay (EMSA)

DNA fragments for EMSA were obtained by PCR-amplification and labeled with [γ-$^{32}$P]ATP using T4 polynucleotide kinase (NEB). The end-labeled probes were purified with Microspin S-200 HR column (GE Healthcare). The labeled DNA fragments were incubated for 25 min with 50 ng of GST-MYB46, GST-MYB83, GST-bZIP1 and GSTANAC041 in a binding buffer [10 mM Tris (pH 7.5), 50 mM KCl, 1 mM DTT, 2.5% glycerol, 5 mM MgCl$_2$, 100 μg/ml BSA, and 50 ng/μL poly(dI-dC)]. Five percent polyacrylamide gel electrophoresis (PAGE) was used to separate the recombinant protein-bound DNA fragments from the unbound ones. The gel was dried and placed in a film cassette and exposed to X-ray film (Kodak) for overnight. Radioactive fragments were visualized by autoradiography. FIG. 3C shows a diagram of the CSLA9 promoter region, illustrating the promoter fragments used in the EMSA assays.

Chromatin Immunoprecipitation (ChIP)

The full-length cDNA of MYB46 was fused in frame with GFP and ligated downstream of the GAL4 upstream activation sequence in pTA7002 binary vector (Aoyama and Chua, Plant J 11(3):605-612 (1997)). See FIG. 4A. The vector construct was used in the *Agrobacterium*-mediated transformation of *Arabidopsis thaliana* (Col-0) plants.

Figure 4A:
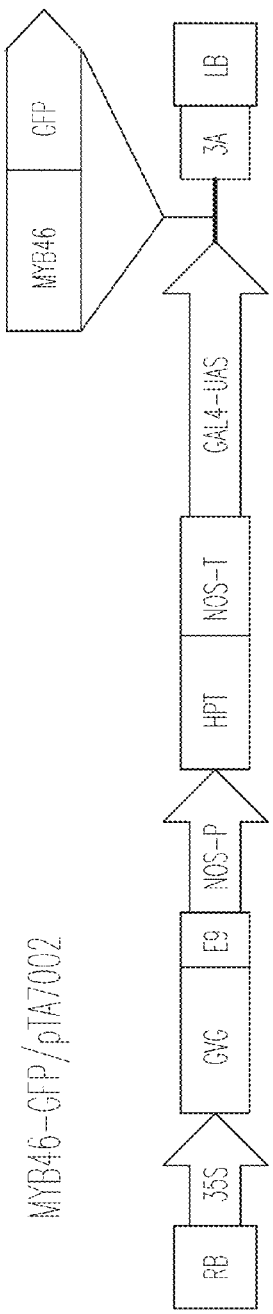
FIG. 4A-4C illustrate chromatin immunoprecipitation (ChIP) of MYB46 bound to the CslA9 promoter sequences in vivo (in *Arabidopsis thaliana* plants).
Figure 4B:
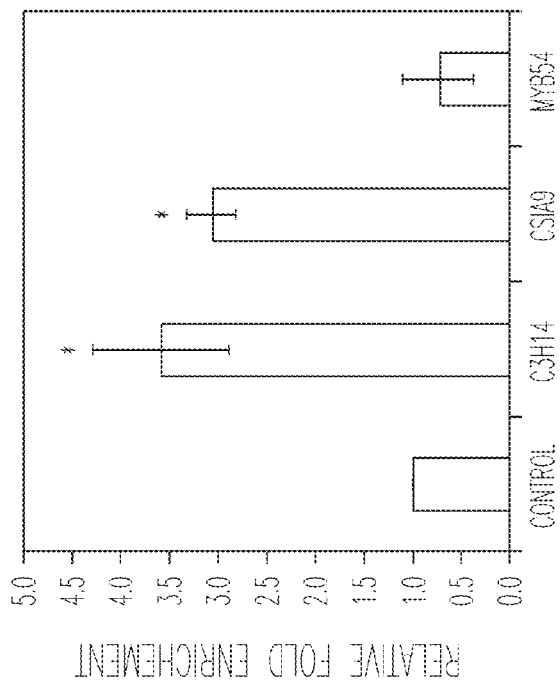
Figure 4C:
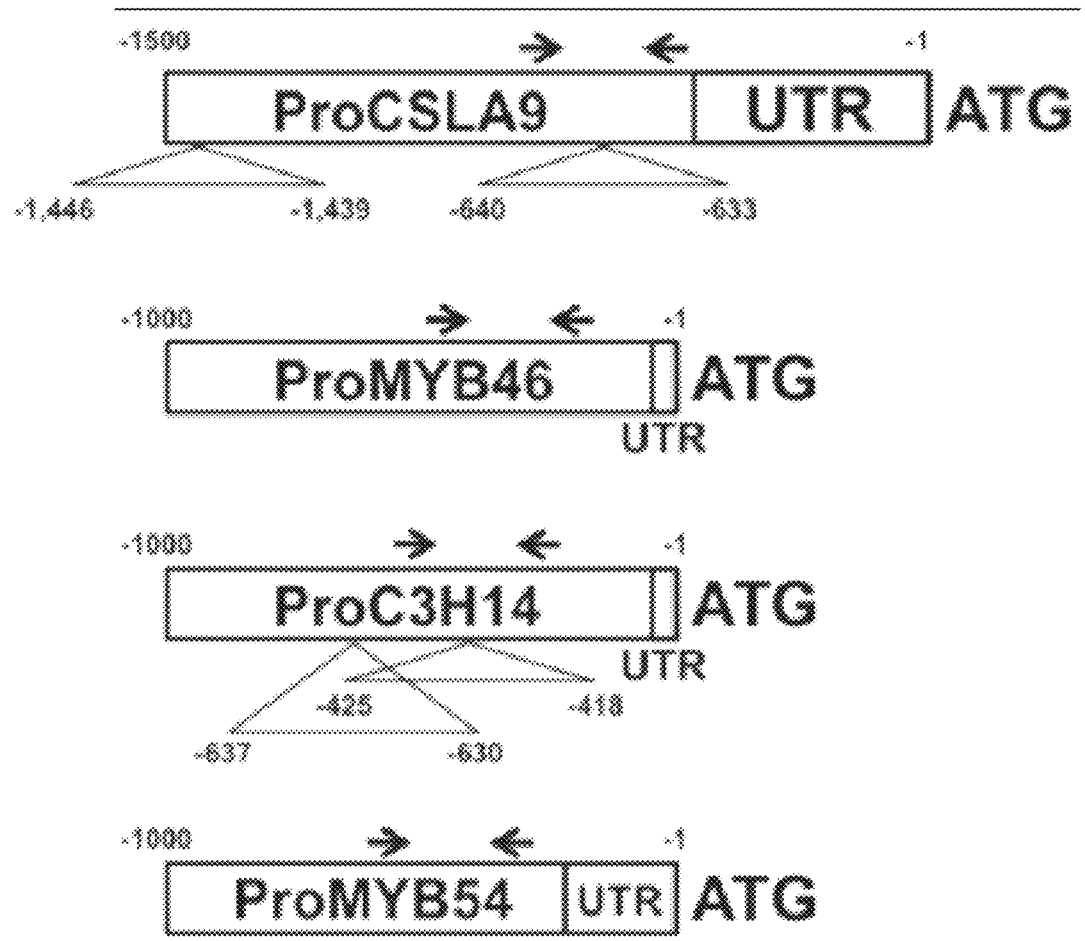

The MYB46-GFP/pTA7002 transgenic plants were grown on soil for three weeks before the dexamethasone (DEX) treatment. DEX (10 μM) was applied by spraying with 0.02% silwet surfactant (Lehle Seeds). Eight hours after the DEX treatment, aerial part of the plants were harvested and cross-linked with 1% formaldehyde for 10 min under vacuum. The cross-linking was quenched in 0.125 M glycine for 5 min. The cross-linked samples were washed three times with deionized water and then ground in liquid nitrogen into a fine powder for extraction of chromatin. ChIP assays were performed as described previously (Kim et al. 2013a). The amount of CSLA9 promoter sequence present in each sample was determined by quantitative real-time PCR using SYBR Premix Ex Taq™ (Takara) and ABI Prism 7900HT Sequence Detection System (ABI). Three biological replications were used in the experiments. A schematic diagram of CSLA9, MYB46, C3H14 and MYB54 promoters is shown in FIG. 4C, with the M46RE sites and primer positions identified.

Microsome Preparation and Mannan Synthase Activity Assay

Leaves were harvested from 5 week-old plants, weighed, and immediately ground in extraction buffer (EB) on ice with a mortar and pestle. EB was prepared as described by Liepman et al. (2005), and approximately 1 ml of EB was used per 100 mg of leaves. The crude homogenate was centrifuged at 3000 g for 10 min at 4° C., and the supernatant was centrifuged at 17000 g for 20 min at 4° C. The resulting supernatant was then centrifuged at 100000 g at 4° C. for 90 min to collect microsome membranes. The membrane pellet was resuspended in EB (0.5 μl/mg leaves). Protein concentration was quantified using the BCA protein assay kit (Pierce). The ManS activity assay was performed as described by Liepman et al. (2005), with modifications. The assay was performed in a total volume of 40 μl containing 20 μl of freshly prepared microsomes, 21.2 μM cold GDP-Man and 3.8 04 GDP-[$^{14}$C]-Man (9.7 GBq/mmol; PerkinElmer) at room temperature for 1 h. Reactions were terminated, and products were pelleted and washed as described by Liepman et al. (2005). Washed pellets were resuspended in 300 μl of water, and used for liquid scintillation counting as described by Wang et al. (2012).

Transactivation Analysis 1500 bp upstream of the 5'UTR of the CSLA9 gene was amplified with the following primers:

```
forward
                                         (SEQ ID NO: 39)
5'-CACCATCACCAAGAGAAGCAACGAAATGTTTGG-3', reverse,
                                         (SEQ ID NO: 40)
5'-CTCTTCTTACTCCGACGAGAACAAAAGAAAACAG-3',
``` and fused to the GUS reporter gene into the binary vector pMDC163.

The full-length cDNA of AtbZIP1 was amplified using the following AtbZIP1 primers:

```
forward
                                      (SEQ ID NO: 41)
5'-CACCATGGCAAACG CAGAGAAGAC-3',
and reverse
                                      (SEQ ID NO: 42)
5'-TCATGTCTTAAAGGACGC-3'.
```

The full-length cDNA of ANAC041 was amplified using the following ANAC041 primers:

```
forward
                                      (SEQ ID NO: 43)
5'-CACC ATGGAGAAGA GGAGCTCTAT TAAAAAC-3', reverse
                                      (SEQ ID NO: 44)
5'-CTATAGAAACAAACAAAAC-3'.
```

Amplicons were then inserted in the pEarley Gate 100 binary vector, under the control of the 35S promoter. Constructs were then mobilized in *Agrobacterium tumefaciens* (strain GV3101) and used to transiently transform *N. tabaccum* leaves sections as described (Reca et al. 2008). The *Agrobacterium* cells containing the promoter of CslA9 fused with the GUS gene was suspended in a volume to obtain a final OD$_{600}$ of 0.01 with infiltration buffer. The *Agrobacterium* transformed with MYB46, AtbZIP1 and ANAC041 were suspended in volume to obtain a final OD$_{600}$ of 0.5 (Reca et al. 2008). Subsequently, the cell suspensions were infiltrated into the lower epidermis of 8- to 12-week-old *N. tabaccum* SR1 (Cv Petit Havana) leaves with a needleless 5 ml syringe. Histochemical GUS staining was performed as described (Jefferson et al. 1987).

Screen for Homozygous T-DNA Lines

Genomic DNA was prepared by use of the RNeasy plant mini kit (Qiagen). Homozygosis lines were verified by PCR using the following primers:

```
atbzip1 (SALK_069489)
                                      (SEQ ID NO: 45)
LP 5'-TCGTCATTCGATGAATCTTCC-3', (SEQ ID NO: 46)
RP 5'-AGACACATACCATTCAAGCCC-3';

atbzip1 (SALK_056773)
                                      (SEQ ID NO: 47)
LP 5'-TGATTCCATTATATAGCACTAGCG-3', (SEQ ID NO: 48)
RP 5'-GATCTCCAGTCTTGAACGACG-3';

anac041 (SALK_066378)
                                      (SEQ ID NO: 49)
LP: 5'-TGTGATTCAAGGGTGGAAGTC-3', (SEQ ID NO: 50)
RP 5'-TTGTTCCGTTTGGTGGTTTAC-3';

anac041 (SALK_010291)
                                      (SEQ ID NO: 51)
LP 5'-AAATGAATTTGTGTTGTTTGGG-3';
and (SEQ ID NO: 52)
RP 5'-CGGTTTACCCTTACCAGCTTC-3'.
```

Non-Cellulosic Neutral Monosaccharide Analysis

Harvested plant materials were lyophilized, ground into a fine powder, and washed three times with 70% ethanol, three times with 1:1 methanol-chloroform, and two times with acetone to obtain alcohol insoluble residue (AIR). The AIR was subsequently de-starched with 1.8 lg amylase (A6380; Sigma-Aldrich) and 0.02 U pullanase (P2986; Sigma-Aldrich) per 10-40 mg AIR. The non-cellulosic neutral monosaccharide composition of the wall matrix polysaccharides was obtained by treating de-starched AIR with trifluoroacetic acid and subsequent derivatization of the solubilized monosaccharides into their corresponding alditol acetates followed by quantification by GC-MS (Albersheim et al. 1967).

Immunofluorescence of Polysaccharides

Samples were taken 1 cm above the stem base of 8-week-old plants and prepared as described by Freshour et al. (1996) using LR White Resin (14381; Electron Microscopy Sciences) as imbedding resin. Transverse sections of 3 mm were then prepared, fixed onto Vectabond-treated (SP-1800; Vectorlabs) microscope slides, blocked with Dulbecco's phosphate-buffered saline (DPBS) 5% skim milk, labeled overnight at 4° C. with the anti-mannan antibodies (a mixture of LM21 and LM22 antibodies were used, Plant-Probes) diluted 1:100 in the blocking buffer. The secondary antibody, FITC::anti-rat IgG (F-6258; Sigma), was diluted 1:100 in the blocking buffer. Sections were then stained in Calcofluor white (0.1 mg/1 ml in PBS buffer) for 5 min. Microscopy was performed using a laser confocal scanning microscope (FV1000D IM-IX81; Olympus). For each antibody, the same exposure time was used for a set of sections, in order to avoid saturation of any one section.

Example 2: Transcription Factor MYB46 is a Direct Upstream Regulator of CSLA9

This Example describes experiments demonstrating that the MYB46 gene encodes a transcription factor that up-regulates the CSLA9 gene.

Real-time PCR experiments were performed to assess whether the CSLA9 gene is up-regulated by MYB46 in wild-type plants as well as in two independent lines that constitutively overexpress MYB46 (OX#8 and OX#9). Total RNA (500 ng) extracted from 5-week-old wild type, OX#8 and OX#9 stems. These total RNA samples were used as templates for RT-PCR (28-31 cycles of amplification).

Figure 1B:
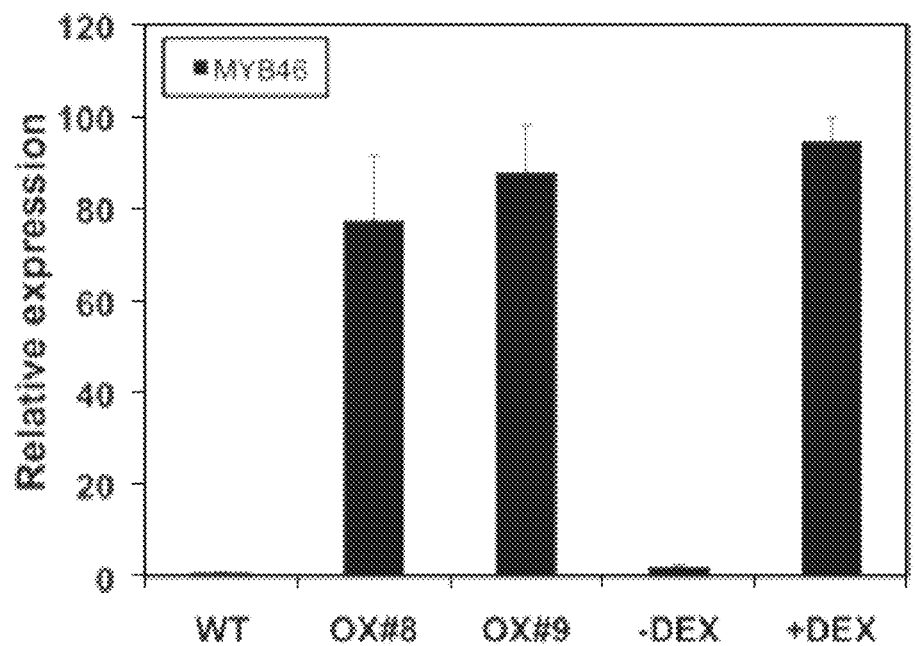
Figure 1C:
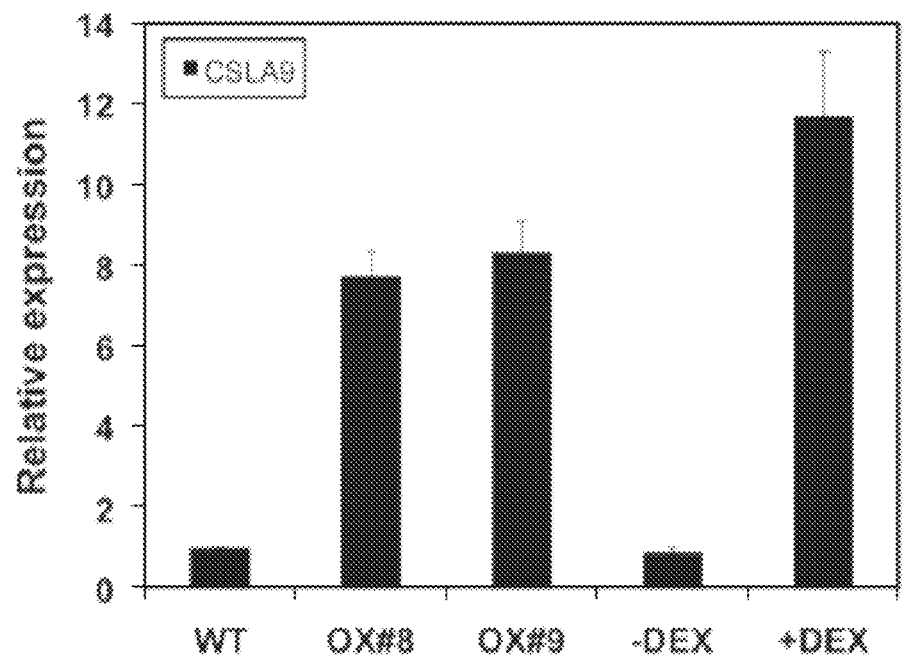

As shown in FIG. 1A-1C, expression levels of CSLA9 gene were lower in wild type plants than in the plants that overexpress MYB46 (OX#8 and OX#9).

Figures 2A, 2B:
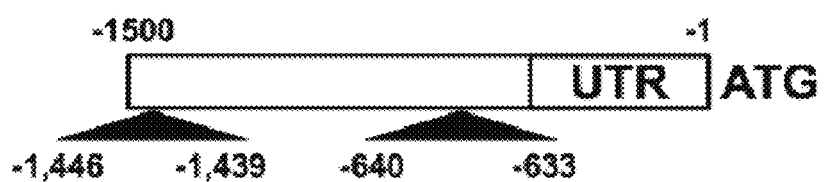
FIG. 2A-2B illustrate that the CslA9 promoter contains two MYB46-Responsive cis-Regulatory Elements (M46REs).

The 5' upstream region of the CSLA9 gene was sequenced to investigate whether the CSLA9 promoter region contains an MYB46-Responsive cis-Regulatory Element (M46RE). As shown in FIG. 2A-2B, the CSLA9 promoter region contained two copies of M46RE at nucleotide positions −1446 to −1439 and at −640 to −633, with sequence [A/G][G/T]T[A/T]GGT[G/A] (SEQ ID NO:1). Taken together, these observations led the inventors to hypothesize that MYB46 (At5g12870) is a direct regulator of the mannan synthase CLSA9.

To evaluate whether MYB46 could directly bind to the CSLA9 promoter sequence, electrophoretic mobility shift assays (EMSAs) were performed with the GST-MYB46 fusion protein as described in Example 1. FIG. 3A shows that the GST-MYB46 fusion protein interacts with, and shifts the mobility of the M46RE motif-containing DNA fragment between −705 to −556 base pairs upstream of the CSLA9 start codon (see FIG. 3C for a schematic diagram of the CSLA9 promoter).

To confirm that MYB46 binds to the CLSA9 promoter region, chromatin immunoprecipitation (ChIP) assays were performed using transgenic Arabidopsis plants expressing GFP-tagged MYB46 under the control of dexamethasone-inducible promoter. FIG. 4A is a schematic diagram of the GFP-tagged MYB46 expression cassette. Dexamethasone (DEX) treatment of the transgenic plants to stimulate expression of the MYB46-GFP fusion protein resulted in ectopic secondary wall thickening in the leaf epidermal and mesophyll cells (data not shown). These results indicate that the MYB46-GFP fusion protein acts as a master switch for secondary wall biosynthesis as does MYB46. After 8 hr of DEX treatment, leaf tissues from 3-week-old plants were fixed with formaldehyde before chromatin was isolated and fragmented. MYB46-GFP-bound DNA fragments were then immunoprecipitated using GFP antibody. These DNA fragments were then employed as templates in the quantitative real-time PCR estimation of the quantity of CSLA9 promoter sequences. The M46RE-containing CSLA9 promoter sequence was highly enriched, by greater that 3-fold compared to control DNA (FIG. 4B). Thus, the EMSA results showing the binding of MYB46 to CSLA9 promoter in vitro were confirmed by chromatin immunoprecipitation (ChIP), demonstrating that the GFP-tagged MYB46 factor binds to the CSLA9 promoter.

The structures of the promoter regions assayed in the ChIP experiments are shown in FIG. 4C. In the ChIP experiments, the promoter regions of AtC3H14 and MYB54 were used as positive and negative controls, respectively. The AtC3H14 promoter is known to be a direct target of MYB46, however, while MYB54 is upregulated by MYB46, the MYB54 promoter is not directly targeted by MYB46 (Kim et al. 2012). As expected, no enrichment of MYB54 promoter DNA was detected in the ChIP experiments, but the AtC3H14 promoter DNA was highly enriched (FIG. 4B). Enrichment of the CSLA9 promoter DNA in the MYB46 immunoprecipate was similar to that observed for the C3H14 promoter DNA. These results demonstrate that MYB46 directly binds to the promoter of CSLA9 gene to regulate its expression.

Example 3: Ectopic Overexpression of MYB46 Increases the Content of Mannan

This Example demonstrates that overexpression of MYB46 increases the content of mannan in Arabidopsis plants To study the effect of MYB46 on mannan biosynthesis, neutral monosaccharide composition analysis was performed using transgenic Arabidopsis plant strains (OX#8 and OX#9) that overexpress MYB46. In order to test whether mannan level increases in the MYB46 overexpression plants had occurred at the enzymatic activity level, ManS activity assays using GDP-[$^{14}$C]-Man and endogenous acceptors were performed using microsomes prepared from the whole stem of each wild type (Col-0) and transgenic (OX#8 and OX#9) plant.

Figure 5A:
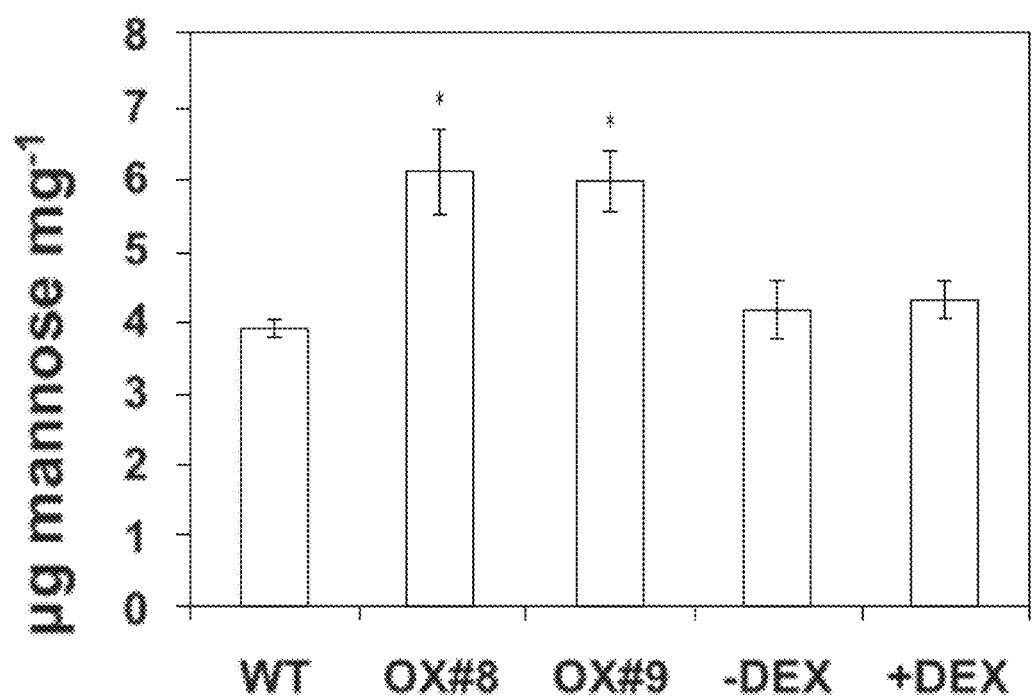
FIG. 5A-5C illustrates the changes in cell-wall mannan composition and in mannan synthase activity detected in plants that overexpress MYB46.

As shown in FIG. 5A, two independent lines that constitutively overexpress MYB46 (OX#8 and OX#9) showed a substantial increase (approximately 50%) in mannose content in stem tissues of plants. The in vitro ManS activity increased from 20 to 50% compared to the wild type. Thus, the changes in ManS activity are consistent with alterations in the levels of mannosyl residues of the cell wall.

Figure 5B:
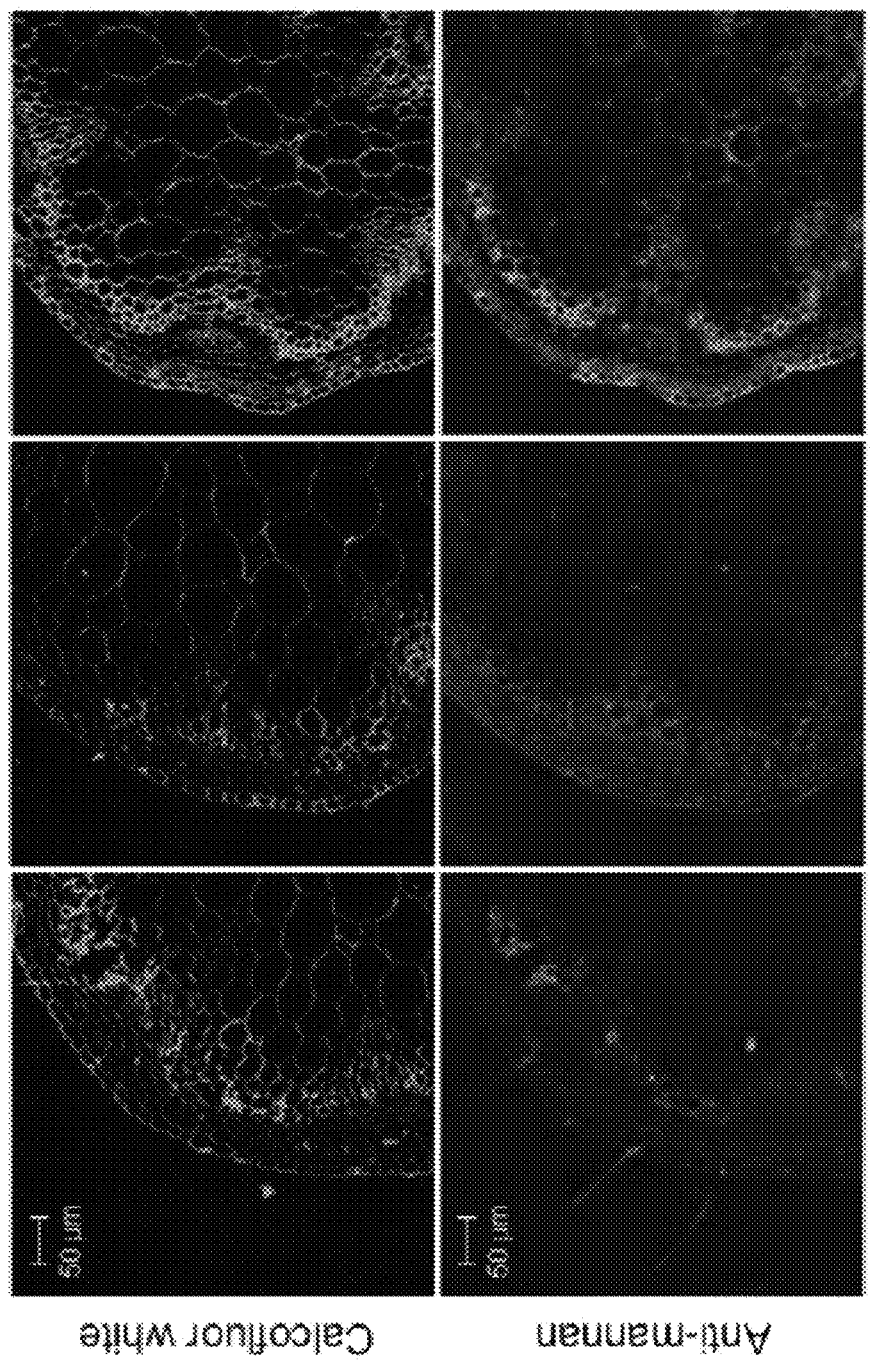
Figure 5C:
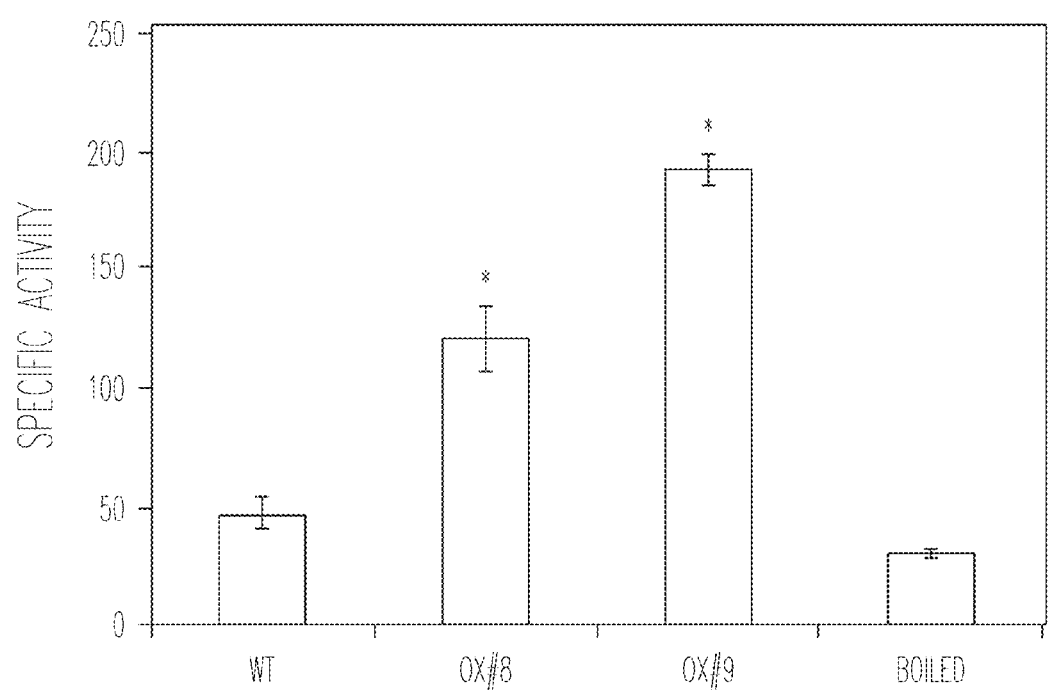

To further confirm the involvement of MYB46 in the regulation of mannan biosynthesis, immunohistochemical analysis was performed on resin imbedded stem cross sections using mannan-specific monoclonal antibodies (a mixture of LM21 and LM22 antibodies were used). In the two independent transgenic plant lines, the level of mannan polysaccharide epitopes in the stems were clearly increased (FIG. 5B), indicating that MYB46 regulates the synthesis of mannan polysaccharides in plants. FIG. 5C graphically illustrates that overexpression of MYB46 increases mannan synthase activity in microsomes prepared from the leaves MYB46 overexpression plant line 8 (OX#8) and MYB46 overexpression plant line 9 (OX#9), compared to wild type.

Example 4: Identification of Additional Transcription Factors that Regulate the Expression of CSLA9

This Example describes transcription factors other than MYB46 that can regulate the CSLA9 gene in plants.

In order to identify the additional transcription factors that bind to the promoter of CLSA9, a yeast one-hybrid (Y1H) screen was carried out using the promoter sequences of CSLA9 as bait and as prey we used the REGIA transcription factors (REgulatory Gene Initiative in Arabidopsis; Paz-Ares and the REGIA Consortium, 2002) were used that had been fused to the GAL4 activation domain (provided by Y. Kim and M. F. Thomashow, DOE-Plant Research Laboratory, Michigan State University). Two candidates transcription factors, ANAC041 (At2g33480) and AtbZIP1 (At5g49450), were identified under high stringency conditions (SD-His-Ura-Trp media containing 40 mM of 3-aminotriazole) (Table 1). PCR analysis verified that these transcription factors interacted with the promoter of the CLSA9 gene. MYB46 was not identified in this Y1H screen because MYB46 is not included in the REGIA transcription factor library that was used.

TABLE 1

Regulators of CslA9 identified by yeast one-hybrid screening

| AGI[a] | Gene description | Promoter[b] |
|---|---|---|
| At2g33480 | ANAC041 | CSLA9 |
| At5g49450 | AtbZIP1 | CSLA9 |

[a]Arabidopsis Gene Index.
[b]Promoter region used in this analysis was −1862 to −463 bp CslA9 upstream of the CslA9 ATG.

Example 5: Transcription Factors ANAC041 and AtbZIP1 Bind to the Promoter of CSLA9

This Example illustrates that the ANAC041 and bZIP1 genes encode transcription factors that bind to the promoter region of CSLA9. As described in the foregoing Example, the ANAC041 and AtbZIP1 gene products were identified by an Y1H assay as candidate regulators with the promoter region of CSLA9.

An electrophoretic mobility shift assay (EMSA) was performed to investigate whether the ANAC041 and AtbZIP1 gene products physically interacted with promoter region of CSLA9 in a manner similar to MYB46. The electrophoretic mobility shift assay (EMSA) was performed using recombinant glutathione S-transferase (GST) fusions with MYB46, ANAC041, or AtbZIP1 shown in FIG. 3A-3B. The binding of these fusion proteins to a CSLA9 promoter fragment was evaluated by electrophoretic separation of the CSLA9 promoter fragment after incubation with the MYB46 protein, the ANAC041 protein, or the AtbZIP1 protein.

Figure 3B:
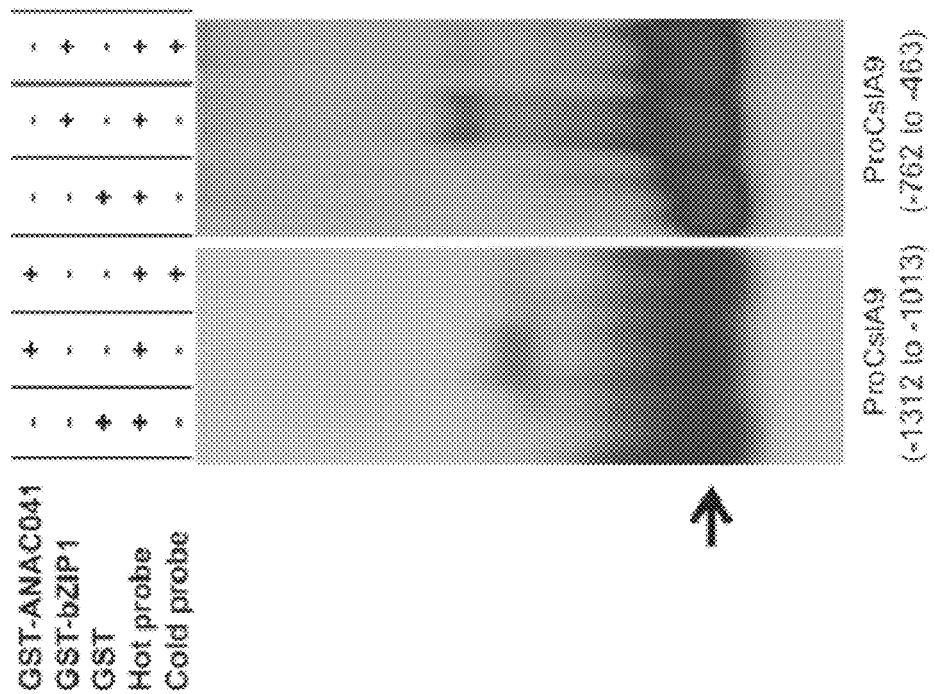
FIG. 3A-3C shows that ANAC041, AtbZIP1 (bZIP1), MYB83, and MYB46 proteins bind to CslA9 promoter fragments as detected by an electrophoretic mobility shift assay (EMSA).
Figure 3A:
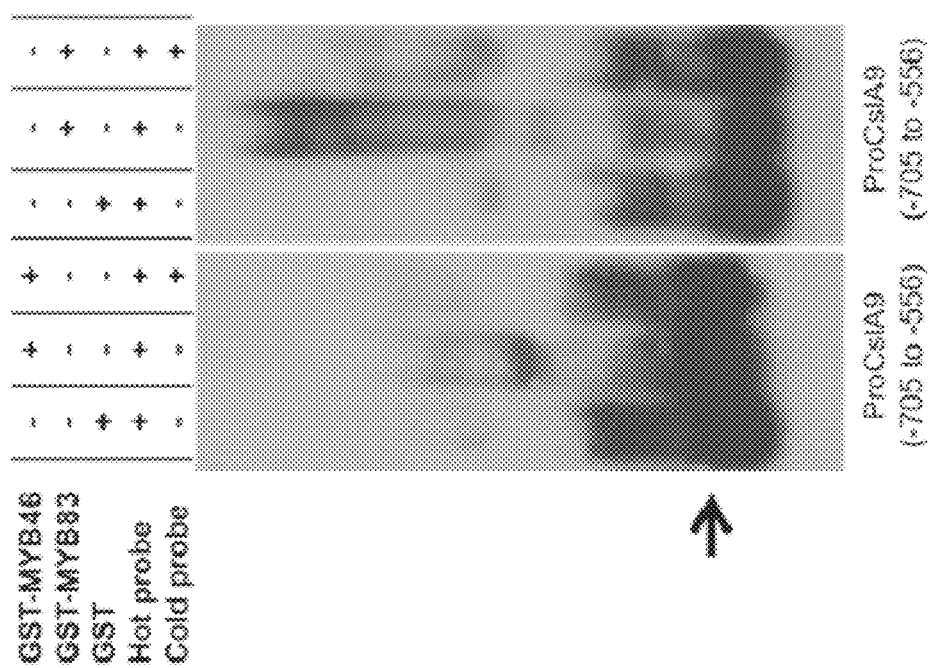
Figure 3C:
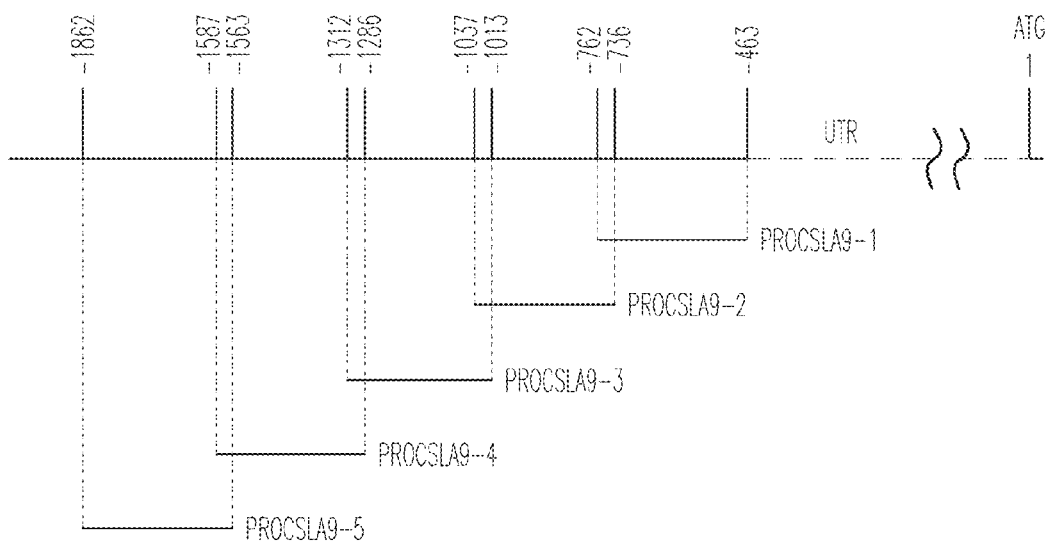

The results from the EMSA assays provided evidence that ANAC041 binds to a region of the promoter that is −1312 to −1013 bp upstream of the start codon and that AtbZIP1 binds to a region that is −762 to −463 bp upstream of the start codon (FIG. 3B). The addition of unlabeled CSLA9 promoter fragments effectively abolished the mobility shift of the radiolabeled fragments, confirming that the binding of the three transcription factors to the CSLA9 promoter was sequence-specific. These data indicate that all three transcription factors (MYB46, ANAC041, and AtbZIP1) directly bind to and interact with the promoter of CSLA9 in vitro.

Example 6: MYB46, AtbZIP1 & ANAC041 Activate Transcription of CSLA9 In Vivo

This Example shows that each of the MYB46, ANAC041 and bZIP1 proteins are transcription factors that can activate the transcription of the CSLA9 gene in vivo.

Figure 6A:
FIG. 6A-6B demonstrate that the ANAC041 and bZIP1 transcription factors, as well as the MYB46 transcription factor, activate expression of CSLA9.
Figure 6A:
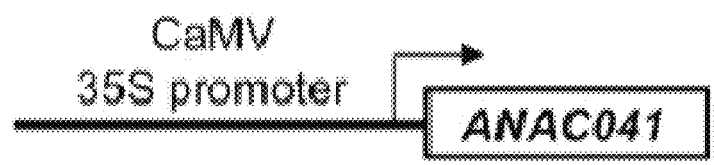
Figure 6A:
Figure 6A:
Figure 6B:
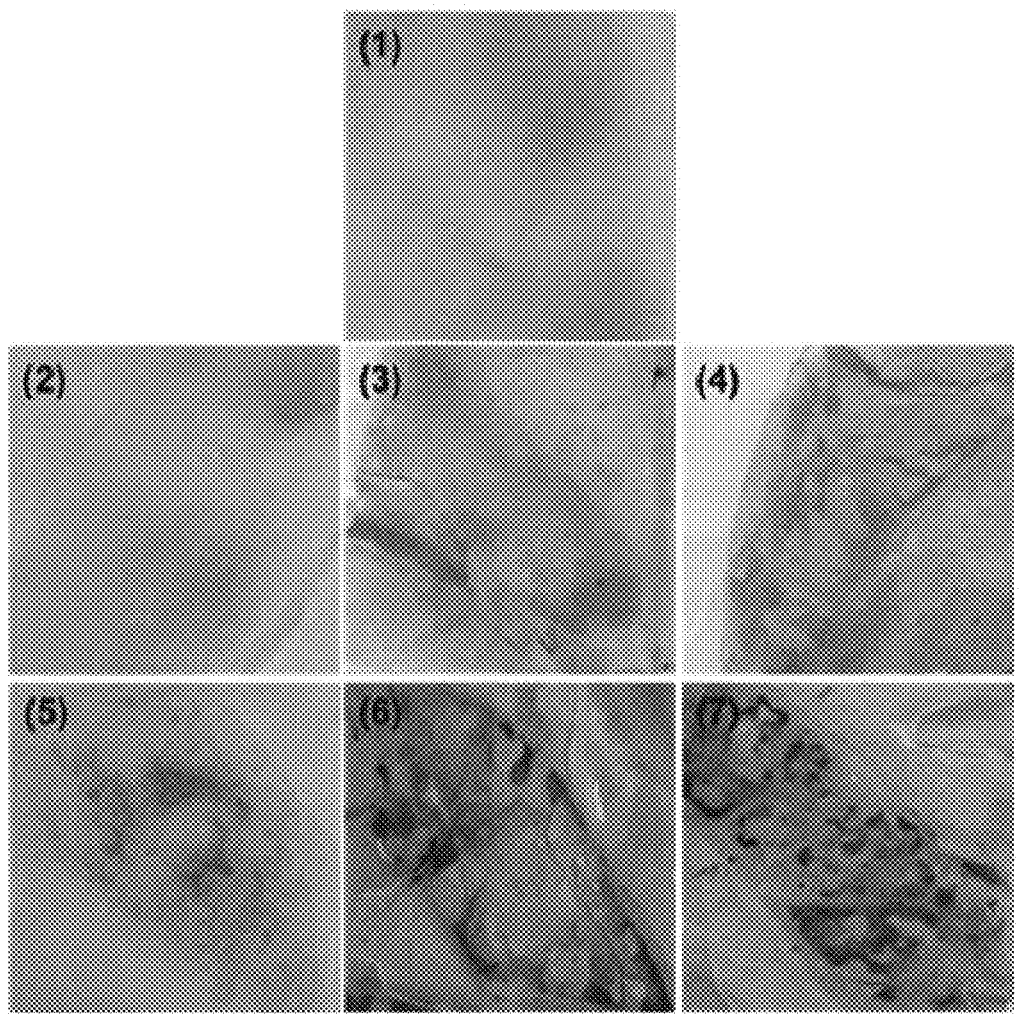

To investigate whether MYB46, bZIP1 and ANAC041 proteins could activate the transcription of CSlA9 in vivo, a transcriptional activation assay was used that had previously been described by the inventors (Ko et al. 2009; Kim et al. 2013a). Tobacco leaves were co-infiltrated with *Agrobacterium tumefaciens* carrying a GUS reporter gene driven by the promoter of CSlA9 (P_AtCSlA9) and *A. tumefaciens* carrying an effector construct encoding MYB45, AtbZIP1 or ANAC041 driven by the 35S promoter (FIG. 6A). The analysis of GUS activity was performed 36 hours after infiltration. As shown in FIG. 6B (panels 5, 6, and 7) all three transcription factors (MYB46, ANAC041 and AtbZIP1) activated the expression of CSlA9 in vivo. In contrast, the controls with no effector or reporter construct showed no GUS expression (FIG. 6B, panels 1, 2, 3, and 4).

Example 7: AtbZIP1 and ANAC041 Knock Out Analysis

To investigate the role of AtbZIP1 and ANAC041 in mannan biosynthesis T-DNA insertional mutant lines, atbzip1 (SALK_069489, SALK_056773) and anac041 (SALK_010291, SALK_066378) were obtained. The atbzip1 and anac041 lines were analyzed for changes in cell wall non-cellulosic neutral monosaccharide composition in the stem, where the wild-type genes are mostly expressed. None of them showed significant differences in the neutral monosaccharide composition nor did they show any altered growth phenotype, compared with wild type (Col-0). These results suggest that MYB46 may act redundantly in the transcriptional regulation of mannan synthesis, providing transcriptional activity when AtbZIP1 and ANAC041 gene functions are missing.

REFERENCES

Albersheim, P, Nevins, D J, English, P D, Karr, A (1967) A method for the analysis of sugars in plant cell wall polysaccharides by gas-liquid chromatography. Carbohydrate Res 5:340-345.

Aoyama T, Chua N H (1997) A glucocorticoid-mediated transcriptional induction system in transgenic plants. Plant J 11(3):605-612. doi: 10.1046/j.1365-313X.1997.11/030,605.x Baena-González E, Rolland F, Thevelein J. M, Sheen J (2007) A central integrator of transcription networks in plant stress and energy signaling. Nature 448(7156):938-942. doi: 10.1038/nature06069

Brown D M, Zeef L A H, Ellis J, Turner S R (2005) Identification of novel genes in *Arabidopsis* involved in secondary cell wall formation using expression profiling and reverse genetics. Plant Cell 17:2281-2295. doi: 10.1105/tpc.105.031542

Buckeridge M S, Santos H P, Tine' MAS (2000a) Mobilisation of storage cell wall polysaccharides in seeds. Plant Physiol Biochem 38: 141-156.

Buckeridge M S, Dietrich S M C, Lima D U (2000b) Galactomannans as the reserve carbohydrate of legume seeds. In AK Gupta, N Kaur, eds, Developments in Crop Science, Vol 26. Elsevier Science B.V., Amsterdam, pp 283-316.

Demura T, Ye Z H (2010) Regulation of plant biomass production. Curr Opin Plant Biol 13:299-304. doi: 10.1016/j.pbi.2010.03.002

Deplancke B, Dupuy D, Vidal M, Walhout A J (2004) A gateway-compatible yeast one-hybrid system. Genome Res 14(10B):2093-101. doi: 10.1101/gr.2445504

Dhugga K S, Barreiro R, Whitten B, Stecca K, Hazebroek J, Randhawa G S, Dolan M, Kinney A J, Tomes D, Nichols S, Anderson P (2004) Guar seed b-mannan synthase is a member of the cellulose synthase super gene family. Science, 303, 363-366. doi: 10.1126/science.1090908

Dietrich K, Weltmeier F, Ehlert A, Weiste C, Stahl M, Harter K, Dröge-Laser W (2011) Heterodimers of the *Arabidopsis* transcription factors bZIP1 and bZIP53 reprogram amino acid metabolism during low energy stress. The Plant cell, 23, 381-395. doi: 10.1105/tpc.110.075390

Freshour G, Clay R P, Fuller M S, Albersheim P, Darvill A G, Hahn M G (1996) Developmental and tissue-specific structural alterations of the cell-wall polysaccharides of *Arabidopsis thaliana* roots. Plant Physiol 110:1413-1429. doi: 10.1104/pp. 110.4.1413

Goubet, F, Barton C J, Mortimer J C, Yu X, Zhang Z, Miles G P, Richens J, Liepman, A H, Seffen K, Dupree P (2009) Cell wall glucomannan in *Arabidopsis* is synthesized by CSLA glycosyltransferases, and influences the progression of embryogenesis. Plant J 60:527-538. doi: 10.1111/j.1365-313X.2009.03977.x Gutierrez L, Mauriat M, Guénin S, Pelloux J, Lefebvre J F, Louvet R, Rusterucci C, Moritz T, Guerineau F, Bellini C, Van Wuytswinkel O (2008) The lack of a systematic validation of reference genes: a serious pitfall undervalued in reverse transcription-polymerase chain reaction (RT-PCR) analysis in plants. Plant Biotechnol J 6(6):609-18. doi:10.1111/j.1467-7652.2008.00346.x Gutiérrez R A, Stokes T L, Thum K, Xu X, Obertello M, Katari M S, Tanurdzic M, Dean A, Nero D C, McClung C R, Coruzzi G M (2008) Systems approach identifies an organic nitrogen-responsive gene network that is regulated by the master clock control gene CCA1. Proc Natl Acad Sci USA 105:4939-4944. doi: 10.1073/pnas.0800211105

Handford M G, Baldwin T C, Goubet F, Prime T A, Miles J, Yu X, Dupree P (2003) Localisation and characterisation of cell wall mannan polysaccharides in *Arabidopsis thaliana*. Planta 218:27-36. doi: 10.1007/s00425-003-1073-9

Harholt J, Jensen J K, Sorensen S O, Orfila C, Pauly M, Scheller H (2006) ARABINAN DEFICIENT 1 is a putative arabinosyltransferase involved in biosynthesis of pectic arabinan in *Arabidopsis*. Plant Physiol 140:49-58. doi: 10. 1104/pp. 105.072744

Kang S G, Price J, Lin P C, Hong J C, Jong J C (2010) The *Arabidopsis* bZIP1 transcription factor is involved in sugar signaling, protein networking, and DNA binding. Mol Plant 3(2):361-373. doi: 10.1093/mp/ssp115

Kim W C, Ko, J H, Han K H (2012) Identification of a cis-acting regulatory motif recognized by MYB46, a master transcriptional regulator of secondary wall biosynthesis. Plant Mol Biol 78:489-501. doi: 10.1007/s11103-012-9880-7

Kim W C, Ko J H, Kim J Y, Kim J M, Bae H J, Han K H (2013a) MYB46 directly regulates the gene expression of secondary wall-associated cellulose synthases in *Arabidopsis*. Plant J 73:26-36. doi: 10.1111/j.1365-313x.2012.05124.x Kim W C, Ko J H, Kim J Y, Kim J M, Han K H (2013b) Transcription factor MYB46 is an obligate component of the transcriptional regulatory complex for functional expression of secondary wall-associated cellulose synthases in *Arabidopsis thaliana*. J Plant Physiol (in press). doi: 10.1016/j.jplph.2013.04.012

Ko J H, Kim W C, Han K H (2009) Ectopic expression of MYB46 identifies transcriptional regulatory genes involved in secondary wall biosynthesis in *Arabidopsis*. Plant J 60(4):649-665. doi:10.1111/j.1365-313X.2009.03989.x Ko J H, Kim W C, Kim J Y, Ahn S J, Han K H (2012) MYB46-mediated transcriptional regulation of secondary wall biosynthesis. Mol Plant 5(5):961-963. doi: 10.1093/mp/sss076

Liepman A H, Cavalier D M, Lerouxel O, Keegstra K (2007) Cell wall structure, biosynthesis, and assembly. In Plant Cell Separation and Adhesion Oxford Blackwell Publishing 8-39. doi: 10.1002/9780470988824.ch 2

Liepman A H, Nairn J, Willats W G T, Sørenson I, Roberts A W, Keegstra K (2007b) Functional genomic analysis supports conservation of function among cellulose synthase-like a gene family members and suggests diverse roles of mannans in plants. Plant Physiol 143:1881-1893. doi: 10.1104/pp. 106.093989

Liepman A H, Wilkerson C G, Keegstra K (2005) Expression of cellulose synthase-like (Csl) genes in insect cells reveals that CslA family members encode mannan synthases. Proc. Natl. Acad. Sci. USA 102:2221-2226. doi: 10.1073/pnas.0409179102

Meier H, Reid J S G (1982) Reserve polysaccharides other than starch in higher plants. In FA Loewus, W Tanner, eds, Encyclopedia of Plant Physiology, Vol 13A. Springer, Berlin, pp 418-471. doi: 10.1007/978-3-642-68275-9_11

Northcote, D H (1972) Chemistry of the plant cell wall Ann Rev Plant Physiol 23:113-132. doi: 10.1146/annurev.pp. 23.060172.000553

Obertello M, Krouk G, Katari M S, Runko S J (2010) Modeling the global effect of the basic-leucine zipper transcription factor 1 (bZIP1) on nitrogen and light regulation in *Arabidopsis*. BMC Syst Biol 4:111. doi: 10.1186/1752-0509-4-111

Jefferson R A, Burgess S M, Hirsh D (1987) beta-Glucuronidase from *Escherichia coli* as a gene-fusion marker. Proc Natl Acad Sci USA 83(22):8447-8451.

Pauly, M. & Keegstra, K (2008) Cell-wall carbohydrates and their modification as a resource for biofuels, The Plant Journal 54(4): 559-568.

Reca I B, Brutus A, D'Avino R, Villard C, Bellincampi D, Giardina T (2008) Molecular cloning, expression and characterization of a novel apoplastic invertase inhibitor from tomato (*Solanum lycopersicum*) and its use to purify a vacuolar invertase. Biochimie 90(11-12):1611-1623. doi: 10.1016/j.biochi.2008.04.019.

Scheller H V, Ulvskov P (2010) Hemicellulose Ann Rev Plant Biol 61:263-289. doi: 10.1146/annurev-arplant-042809-112315

Sun X L, Li Y, Cai H, Bai X, Ji W, Ji Z J, Zhu Y M (2011) *Arabidopsis* bZIP1 transcription factor binding to ABRE cis-element regulates abscisic acid signal transduction. Acta Agronomica Sinica 37(4):612-619. doi: 10.1016/S1875-2780(11)60016-3

Suzuki S, Li L, Sun Y H, Chiang V L (2006) The cellulose synthase gene superfamily and biochemical functions of xylem-specific cellulose synthase-like genes in *Populus trichocarpa*. Plant Physiol. 142:1233-1245. doi: 10.1104/pp. 106.086678

Walhout A J, Vidal M (2001) High-throughput yeast two-hybrid assays for large-scale protein interaction mapping. Methods 24(3):297-306. doi: 10.1006/meth.2001.1190

Wang Y, Alonso A P, Wilkerson C G, Keegstra K (2012) Deep EST profiling of developing fenugreek endosperm to investigate galactomannan biosynthesis and its regulation. Plant Mol Biol 79:243-258. doi: 10.1007/s11103-012-9909-y Wang H Z, Dixon R A (2012) On-off switches for secondary cell wall biosynthesis. Mol Plant 5:297-303. doi: 10.1093/mp/ssr098

Yin Y, Huang J, Xu Y (2009) The cellulose synthase superfamily in fully sequenced plants and algae. BMC Plant Biol 9:99-113. doi: 10.1186/1471-2229-9-99

Zhong R, Richardson E A, Ye Z H (2007) The MYB46 transcription factor is a direct target of SND1 and regulates secondary wall biosynthesis in *Arabidopsis*. Plant Cell 19(9):2776-2792. doi: 10.1105/tpc.107.053678

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The following statements of the invention are intended to describe and summarize various embodiments of the invention according to the foregoing description in the specification.

Statements:

1. An isolated nucleic acid comprising a nucleic acid segment encoding an ANAC041, bZIP1, or MYB46 transcription factor operably linked to a heterologous promoter.

2. The isolated nucleic acid of statement 1, wherein the nucleic acid segment encoding the transcription factor is a cDNA.

3. The isolated nucleic acid of statement 1 or 2, wherein the transcription factor comprises an amino acid sequence with at least 40% sequence identity to a sequence selected from the group consisting of SEQ ID NOs:3, 5, 7, 9, 11, 13, 15, 17, 19, 21, 23, 24, 25, 27, 29, 31, 33, 35, and any combination thereof.

4. The isolated nucleic acid of any of statements 1-3, wherein the nucleic acid segment encoding the transcription factor that selectively hybridizes to any of SEQ ID NO:2, 4, 6, 8, 10, 12, 14, 16, 18, 20, 22, 26, 28, 30, 32 or 34 under stringent hybridization conditions.

5. The isolated nucleic acid of any of statements 1-4, wherein the nucleic acid segment encoding the transcription factor selectively hybridizes to any of SEQ ID NO:2, 4, 6, 8, 10, 12, 14, 16, 18, 20, 22, 26, 28, 30, 32 or 34 under stringent hybridization conditions comprising a wash in 0.1×SSC, 0.1% SDS at 65° C.

6. The isolated nucleic acid of any of statements 1-5, wherein the segment encoding the transcription factor comprises a nucleic acid sequence with at least 50% sequence identity to a sequence selected from the group consisting of SEQ ID NOs: SEQ ID NO:2, 4, 6, 8, 10, 12, 14, 16, 18, 20, 22, 26, 28, 30, 32, 34, and any combination thereof.

7. The isolated nucleic acid of any of statements 1-6, wherein the heterologous promoter is a CaMV 35S promoter, CaMV 19S promoter, a nos promoter, Adh1, sucrose synthase promoter, α-tubulin promoter, ubiquitin promoter, actin promoter, cab promoter, PEPCase promoter, GAL4/UAS promoter, R gene complex promoter, poplar xylem-specific secondary cell wall specific cellulose synthase 8 promoter, cauliflower mosaic virus promoter, the Z10 promoter from a gene encoding a 10 kD zein protein, a Z27 promoter from a gene encoding a 27 kD zein protein, pea rbcS promoter, actin promoter, phaseolin promoter or a combination thereof.

8. An expression cassette comprising the isolated nucleic acid of any of statements 1-7.

9. The expression cassette of statement 8, comprising a heterologous promoter selected from the group consisting of an inducible promoter, a tissue specific promoter, a constitutive promoter, an environmentally regulated promoter, a developmentally regulated promoter, and a combination thereof.

10. The expression cassette of statement 8 or 9, comprising a heterologous promoter that is light-inducible, chemically-inducible, environmentally inducible, or developmentally inducible.

11. The expression cassette of any of statements 8-10, comprising a heterologous promoter that is inducible by alcohol (e.g., ethanol), acetaldehyde, isothiopropylgalactoside, metal, steroids, dexamethasone, hydrogen peroxide, plant hormones (e.g., methyl jasmonate), drought, cold, heat, longer exposure to light, shorter exposure to light, and other compounds.

12. A transgene comprising the isolated nucleic acid of any of statements 1-7, or the expression cassette of any of statements 8-11.

13. A plant cell comprising the isolated nucleic acid of any of statements 1-7, the expression cassette of any of statements 8-11, or the transgene of statement 12.

14. A plant comprising the isolated nucleic acid of any of statements 1-7, the expression cassette of any of statements 8-11, or the transgene of statement 12.

15. A plant seed comprising the isolated nucleic acid of any of statements 1-7, the expression cassette of any of statements 8-11, or the transgene of statement 12.

16. A method of generating a transgenic plant comprising recombinantly transforming the plant with the isolated nucleic acid of any of statements 1-7, the expression cassette of any of statements 8-11, or the transgene of statement 12, to thereby generate a transgenic plant.

17. A method of increasing expression of CSLA9 enzyme(s) in a plant comprising recombinantly transforming the plant with the isolated nucleic acid of any of statements 1-7, the expression cassette of any of statements 8-11, or the transgene of statement 12, to thereby increase expression of CSLA9 enzyme(s) in the plant.

18. The method of statement 16, further comprising inducing expression of the CSLA9 enzyme(s) by exposing the plant to a chemical (e.g., an inducing agent) or environmental stimulus that induces expression of the CSLA9 enzyme(s) in tissues of the plant.

19. A method of increasing expression of CSLA9 enzyme in a plant comprising transiently or constitutively expressing an ANAC041, bZIP1, or MYB46 transcription factor from the isolated nucleic acid of any of statements 1-7, the expression cassette of any of statements 8-11, or the transgene of statement 12, to thereby increase expression of the CSLA9 enzyme(s) in tissues of the plant; wherein the plant comprises such a nucleic acid, expression cassette or transgene.

20. A method of generating mannose and/or mannan-containing saccharides comprising: digesting plant biomass comprising the isolated nucleic acid of any of statements 1-7, the expression cassette of statement 8, or the transgene of statement 9 under conditions sufficient to release mannose sugars and/or mannan-containing oligosaccharides from the plant biomass.

21. A method of generating mannose sugars and/or mannan-containing oligosaccharides comprising: (a) growing a plant from a seed comprising the isolated nucleic acid of any of statements 1-7, the expression cassette of statement 8, or the transgene of statement 9 to generate a grown plant; (b) generating a plant biomass from the grown plant; (c) digesting the plant biomass under conditions sufficient to release mannose sugars and/or mannan-containing oligosaccharides from the plant biomass, to thereby generate mannose sugars and/or mannan-containing oligosaccharides.

22. An expression cassette comprising a CSLA9 promoter.

23. The expression cassette of statement 22, comprising a nucleic acid segment encoding a heterologous product (e.g., a protein or an RNA) and a promoter with at least 60% sequence identity, or at least 70% sequence identity, or at least 80% sequence identity, or at least 85% sequence identity, or at least 90% sequence identity, or at least 95% sequence identity, or at least 90% sequence identity to SEQ ID NO:38.

24. The expression cassette of statement 22, comprising a segment of at least 200 nucleotides, or at least 300 nucleotides, or at least 400 nucleotides, or at least 500 nucleotides, or at least 600 nucleotides, or at least 700 nucleotides, or at least 800 nucleotides, or at least 900 nucleotides, or at least 1000 nucleotides of SEQ ID NO:38.

25. The expression cassette of statement 22, comprising a cDNA nucleic acid segment encoding a CSLA9 enzyme operably linked to the CSLA9 promoter.

26. A method of synthesizing a gene product comprising recombinantly transforming a plant with the expression cassette of statement 22.

27. A method of synthesizing a gene product comprising inducing expression from the expression cassette of any of statements 22-25.

28. The method of statement 27, performed in vitro or in vivo.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and the methods and processes are not necessarily restricted to the orders of steps indicated herein or in the claims.

As used herein and in the appended claims, the singular forms "a," "an," and "the" include plural reference unless the context clearly dictates otherwise. Thus, for example, a reference to "a nucleic acid" or "a polypeptide" includes a plurality of such nucleic acids or polypeptides (for example, a solution of nucleic acids or polypeptides or a series of nucleic acid or polypeptide preparations), and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims and statements of the invention.

What is claimed:

1. A transgenic plant, plant cell or plant seed comprising a nucleic acid segment encoding an ANAC041, bZIP1, or MYB46 transcription factor operably linked to a heterologous xylem-specific secondary cell wall specific cellulose synthase 8 promoter, where expression of the transcription factor activates transcription of CSLA9 in vivo.

2. The plant, plant cell or plant seed of claim 1, wherein the nucleic acid segment encoding the transcription factor is a cDNA.

3. An expression cassette or transgene comprising a nucleic acid segment encoding an ANAC041, bZIP1, or MYB46 transcription factor operably linked to a xylem-specific secondary cell wall specific cellulose synthase 8 promoter.

4. A method of increasing expression of CSLA9 enzyme(s) in a plant comprising recombinantly transforming the plant with a nucleic acid segment encoding an ANAC041, bZIP1, or MYB46 transcription factor operably linked to a xylem-specific secondary cell wall specific cellulose synthase 8 promoter, to thereby increase expression of CSLA9 enzyme(s) in the plant.

5. The method of claim 4, further comprising transiently expressing the ANAC041, bZIP1, or MYB46 transcription factor in the plant.

6. A method of generating mannose and/or mannan-containing saccharides comprising:
  digesting plant biomass comprising a nucleic acid segment encoding an ANAC041, bZIP1, or MYB46 transcription factor operably linked to a xylem-specific secondary cell wall specific cellulose synthase 8 promoter, under conditions sufficient to release mannose sugars and/or mannan-containing oligosaccharides from the plant biomass.

7. A method of generating mannose sugars and/or mannan-containing oligosaccharides comprising:
  (a) growing a plant from the seed comprising a nucleic acid segment encoding an ANAC041, bZIP1, or MYB46 transcription factor operably linked to a xylem-specific secondary cell wall specific cellulose synthase 8 promoter to generate a grown plant;
  (b) generating a plant biomass from the grown plant;
  (c) digesting the plant biomass under conditions sufficient to release mannose sugars and/or mannan-containing oligosaccharides from the plant biomass;
  to thereby generate mannose sugars and/or mannan-containing oligosaccharides.

* * * * *

SEQUENCE LISTING

```
<160> NUMBER OF SEQ ID NOS: 52

<210> SEQ ID NO 1
<211> LENGTH: 8
<212> TYPE: DNA
<213> ORGANISM: Artificial Sequence
<220> FEATURE:
<223> OTHER INFORMATION: A synthetic oligonucleotide
<221> NAME/KEY: misc_feature
<222> LOCATION: 1
<223> OTHER INFORMATION: n = a or g
<221> NAME/KEY: misc_feature
<222> LOCATION: 2
<223> OTHER INFORMATION: n = g or t
<221> NAME/KEY: misc_feature
<222> LOCATION: 4
<223> OTHER INFORMATION: n = a or t
<221> NAME/KEY: misc_feature
<222> LOCATION: 8
<223> OTHER INFORMATION: n = g or a

<400> SEQUENCE: 1 nntnggtn                                                                    8

<210> SEQ ID NO 2
<211> LENGTH: 807
<212> TYPE: DNA
<213> ORGANISM: Arabidopsis thaliana

<400> SEQUENCE: 2
atggagaaga ggagctctat taaaaacaga ggagtactta gattaccacc agggttccga      60
tttcacccga ccgatgaaga gctagtggtt caatatttac gtcgaaaagt aaccggttta     120
cccttaccag cttctgtaat accggaaacc gatgtttgta aatccgatcc atgggattta     180
ccaggtgatt gtgaatcaga gatgtatttt tttagcacga gggaagctaa atacccgaac     240
ggaaaccggt cgaaccggtc taccggttcg ggttattgga aagcgactgg tctcgataag     300
cagatcggta agaagaagct tgtcgtgggg atgaagaaaa ctcttgtttt ctacaaaggt     360
aaaccaccaa acgaacaag aactaactgg gttcttcatg aatatcgtct tgttgattca     420
caacaagatt cattatatgg acagaacatg aattgggttt tgtgtagagt gttcttgaag     480
aagagaagca atagtaatag taagaggaaa gaagatgaga aagaagaggt ggagaatgag     540
aaagagacag agacagagag agaacgtgag gaggagaaca agaagagtac ttgtcccata     600
```

```
ttttatgact ttatgagaaa agacacgaag aaaaagagaa ggagaagaag atgctgtgat        660
ttgaatttga ctcctgctac ttgttgttgt tgctcttctt cgacttcttc gtcgtctgtt        720
tgctcaagtg ctttaactca cacatcttct aatgataatc gtcaagaaat cagttatcgg        780
gaaaataagt tttgtttgtt tctatag                                           807
```

```
<210> SEQ ID NO 3
<211> LENGTH: 268
<212> TYPE: PRT
<213> ORGANISM: Arabidopsis thaliana

<400> SEQUENCE: 3

Met Glu Lys Arg Ser Ser Ile Lys Asn Arg Gly Val Leu Arg Leu Pro
 1               5                  10                  15

Pro Gly Phe Arg Phe His Pro Thr Asp Glu Glu Leu Val Val Gln Tyr
            20                  25                  30

Leu Arg Arg Lys Val Thr Gly Leu Pro Leu Pro Ala Ser Val Ile Pro
        35                  40                  45

Glu Thr Asp Val Cys Lys Ser Asp Pro Trp Asp Leu Pro Gly Asp Cys
    50                  55                  60

Glu Ser Glu Met Tyr Phe Phe Ser Thr Arg Glu Ala Lys Tyr Pro Asn
65                  70                  75                  80

Gly Asn Arg Ser Asn Arg Ser Thr Gly Ser Gly Tyr Trp Lys Ala Thr
                85                  90                  95

Gly Leu Asp Lys Gln Ile Gly Lys Lys Lys Leu Val Val Gly Met Lys
           100                 105                 110

Lys Thr Leu Val Phe Tyr Lys Gly Lys Pro Pro Asn Gly Thr Arg Thr
        115                 120                 125

Asn Trp Val Leu His Glu Tyr Arg Leu Val Asp Ser Gln Gln Asp Ser
    130                 135                 140

Leu Tyr Gly Gln Asn Met Asn Trp Val Leu Cys Arg Val Phe Leu Lys
145                 150                 155                 160

Lys Arg Ser Asn Ser Asn Ser Lys Arg Lys Glu Asp Glu Lys Glu Glu
                165                 170                 175

Val Glu Asn Glu Lys Glu Thr Glu Thr Glu Arg Glu Arg Glu Glu Glu
           180                  185                 190

Asn Lys Lys Ser Thr Cys Pro Ile Phe Tyr Asp Phe Met Arg Lys Asp
        195                 200                 205

Thr Lys Lys Arg Arg Arg Arg Cys Cys Asp Leu Asn Leu Thr
    210                 215                 220

Pro Ala Thr Cys Cys Cys Cys Ser Ser Ser Thr Ser Ser Ser Ser Val
225                 230                 235                 240

Cys Ser Ser Ala Leu Thr His Thr Ser Ser Asn Asp Asn Arg Gln Glu
                245                 250                 255

Ile Ser Tyr Arg Glu Asn Lys Phe Cys Leu Phe Leu
           260                 265
```

```
<210> SEQ ID NO 4
<211> LENGTH: 1045
<212> TYPE: DNA
<213> ORGANISM: Arabidopsis thaliana

<400> SEQUENCE: 4
taaaataagc caaactttac ctctccattt tcaataatct ctcatcttct ttcgtctctc        60
tttctacggt tcaaacatta aaagatagat ggagaagag gagctctatt aaaaacagag        120
```

```
gagtacttag attaccacca gggttccgat tcacccgac cgatgaagag ctagtggttc    180
aatatttacg tcgaaaagta accggtttac ccttaccagc ttctgtaata ccggaaaccg    240
atgtttgtaa atccgatcca tgggatttac caggtgattg tgaatcagag atgtatttt     300
ttagcacgag ggaagctaaa tacccgaacg gaaccggtc gaaccggtct accggttcgg     360
gttattggaa agcgactggt ctcgataagc agatcggtaa gaagaagctt gtcgtgggga    420
tgaagaaaac tcttgttttc tacaaaggta accaccaaa cggaacaaga actaactggg     480
ttcttcatga atatcgtctt gttgattcac aacaagattc attatataac atgaattggg    540
ttttgtgtag agtgttcttg aagaagagaa gcaatagtaa tagtaagagg aagaagatg     600
agaaagaaga ggtggagaat gagaaagaga cagagacaga gagaacgt gaggaggaga      660
acaagaagag tacttgtccc atattttatg actttatgag aaaagacacg aagaaaaga    720
gaaggagaag aagatgctgt gatttgaatt tgactcctgc tacttgttgt tgttgctctt    780
cttcgacttc ttcgtcgtct gtttgctcaa gtgctttaac tcacacatct tctaatgata   840
atcgtcaaga aatcagttat cgggaaaata agttttgttt gtttctatag attaacaaac   900
ttgggaacaa cttctattaa ctttaataaa ttagattatg attgtttcca aagttaatta  960
tgcaatccag gagtctttct tggttttggt aattaatagc catattttat agcttatcta   1020
attgtatcaa atattgaaaa ctggt                                          1045

<210> SEQ ID NO 5
<211> LENGTH: 266
<212> TYPE: PRT
<213> ORGANISM: Arabidopsis thaliana

<400> SEQUENCE: 5

Met Glu Lys Arg Ser Ser Ile Lys Asn Arg Gly Val Leu Arg Leu Pro
  1               5                  10                  15

Pro Gly Phe Arg Phe His Pro Thr Asp Glu Glu Leu Val Val Gln Tyr
                 20                  25                  30

Leu Arg Arg Lys Val Thr Gly Leu Pro Leu Pro Ala Ser Val Ile Pro
             35                  40                  45

Glu Thr Asp Val Cys Lys Ser Asp Pro Trp Asp Leu Pro Gly Asp Cys
         50                  55                  60

Glu Ser Glu Met Tyr Phe Phe Ser Thr Arg Glu Ala Lys Tyr Pro Asn
 65                  70                  75                  80

Gly Asn Arg Ser Asn Arg Ser Thr Gly Ser Gly Tyr Trp Lys Ala Thr
                 85                  90                  95

Gly Leu Asp Lys Gln Ile Gly Lys Lys Leu Val Val Gly Met Lys
            100                 105                 110

Lys Thr Leu Val Phe Tyr Lys Gly Lys Pro Pro Asn Gly Thr Arg Thr
            115                 120                 125

Asn Trp Val Leu His Glu Tyr Arg Leu Val Asp Ser Gln Gln Asp Ser
        130                 135                 140

Leu Tyr Asn Met Asn Trp Val Leu Cys Arg Val Phe Leu Lys Lys Arg
145                 150                 155                 160

Ser Asn Ser Asn Ser Lys Arg Lys Glu Asp Glu Lys Glu Glu Val Glu
                165                 170                 175

Asn Glu Lys Glu Thr Glu Thr Glu Arg Glu Arg Glu Glu Asn Lys
            180                 185                 190

Lys Ser Thr Cys Pro Ile Phe Tyr Asp Phe Met Arg Lys Asp Thr Lys
        195                 200                 205
```

Lys Lys Arg Arg Arg Arg Arg Cys Cys Asp Leu Asn Leu Thr Pro Ala
    210                 215                 220

Thr Cys Cys Cys Cys Ser Ser Ser Thr Ser Ser Ser Ser Val Cys Ser
225                 230                 235                 240

Ser Ala Leu Thr His Thr Ser Ser Asn Asp Asn Arg Gln Glu Ile Ser
                245                 250                 255

Tyr Arg Glu Asn Lys Phe Cys Leu Phe Leu
            260                 265

<210> SEQ ID NO 6
<211> LENGTH: 1312
<212> TYPE: DNA
<213> ORGANISM: Populus trichocarpa

<400> SEQUENCE: 6

```
cacctctttg attccctctc tcacccttttt ctccctctct tacatctctt tccatactct      60
aataatttat ctattgctct ccttttcttc ttcttcttga ggctctttgt ctaatattct     120
ctttgtgtaa aactttaatg ggttattaca actataagaa gtgtgcatga gttttttagac    180
tttgagctag aattgcgcag ctccaatagc tggtggagac attttttgagc cacaaggcac    240
atacatacac atacagtctt ttttttgttcc ttttgaagtt cttgtgaggt ctttcataa    300
gggtatggag aagcttagtt ttgttaagaa tggtgtgctt agattgcctc ctggatttag    360
gttccaccca acagatgagg agcttgttgt ccagtacttg aagagaaagg tgtttgcttg    420
cccccttgcct gcttccataa tccctgaagt cgatgtttgc aagtctgatc cttgggattt    480
gccaggtgat ttggagcaag aacggtactt tttcagcacc agagaagcca aatatcccaa    540
tgggaatcga tccaacagag ccacaggctc tggctactgg aaggcaactg aatagacaa     600
gcaaattgtg acttctaagg ccaccaagt tgtggggatg aagaaactc tggttttta     660
cagaggaaag cccccccatg cactaggac tgattggatc atgcatgaat accgccttgc     720
aagcactgaa accacagcct gcaatacct gaaaataaa aattcaactc agggccctgt    780
tgtggtgcca atggaaaatt gggttctatg ccgcatattt ttgaagaaga gaggcacaaa    840
aaatgaggag gaaacattc aagttggcaa tgataataga ctgcccaaac tcagggccac    900
tgagcctgtt ttctatgatt tcatgacaaa ggagaagaca actgatttga atctagctcc    960
ttcctcttca tcctcaggat ccagtggaat cacagaggag gtgtcctgta atgaatcaga   1020
tgatcacgaa gagagtagta gttgcaatag ttttccttac gttagaagaa accatagct   1080
agaatggccc tcttaattag tctttagttc ttgtatccgt atttaggggg tctggcttct   1140
caaccagaat agtcatctta agcaatctaa tgcttgtgtc tttcggtttc gtctctctca   1200
tctgtgagtt cacaagaaaa gaaagaaaa acaaacccgg cattaactgt taccagtaat   1260
gtagagagga agtatggatg tcaagttgtc atgtaatcaa aaatttcaaa gt           1312
```

<210> SEQ ID NO 7
<211> LENGTH: 257
<212> TYPE: PRT
<213> ORGANISM: Populus trichocarpa

<400> SEQUENCE: 7

Met Glu Lys Leu Ser Phe Val Lys Asn Gly Val Leu Arg Leu Pro Pro
1               5                   10                  15

Gly Phe Arg Phe His Pro Thr Asp Glu Glu Leu Val Val Gln Tyr Leu
            20                  25                  30

Lys Arg Lys Val Phe Ala Cys Pro Leu Pro Ala Ser Ile Ile Pro Glu

```
                35                  40                  45
Val Asp Val Cys Lys Ser Asp Pro Trp Asp Leu Pro Gly Asp Leu Glu
 50                  55                  60

Gln Glu Arg Tyr Phe Phe Ser Thr Arg Glu Ala Lys Tyr Pro Asn Gly
 65                  70                  75                  80

Asn Arg Ser Asn Arg Ala Thr Gly Ser Gly Tyr Trp Lys Ala Thr Gly
                 85                  90                  95

Ile Asp Lys Gln Ile Val Thr Ser Lys Gly His Gln Val Val Gly Met
                100                 105                 110

Lys Lys Thr Leu Val Phe Tyr Arg Gly Lys Pro Pro His Gly Thr Arg
                115                 120                 125

Thr Asp Trp Ile Met His Glu Tyr Arg Leu Ala Ser Thr Glu Thr Thr
130                 135                 140

Ala Cys Asn Thr Leu Lys Asn Lys Asn Ser Thr Gln Gly Pro Val Val
145                 150                 155                 160

Val Pro Met Glu Asn Trp Val Leu Cys Arg Ile Phe Leu Lys Lys Arg
                165                 170                 175

Gly Thr Lys Asn Glu Glu Asn Ile Gln Val Gly Asn Asp Asn Arg
                180                 185                 190

Leu Pro Lys Leu Arg Ala Thr Glu Pro Val Phe Tyr Asp Phe Met Thr
                195                 200                 205

Lys Glu Lys Thr Thr Asp Leu Asn Leu Ala Pro Ser Ser Ser Ser
210                 215                 220

Gly Ser Ser Gly Ile Thr Glu Glu Val Ser Cys Asn Glu Ser Asp Asp
225                 230                 235                 240

His Glu Glu Ser Ser Ser Cys Asn Ser Phe Pro Tyr Val Arg Arg Lys
                245                 250                 255

Pro

<210> SEQ ID NO 8
<211> LENGTH: 750
<212> TYPE: DNA
<213> ORGANISM: Brassica napus

<400> SEQUENCE: 8
atggataagg ttaaacttgt aaagaatggt gttatgagat taccacctgg attcagattt      60
catcccactg atgaggaact tgtggttcag tatctcaaga gaaaagtctt gtcttctcca     120
ttaccagctt ccatcattcc tgactttgat gtttgcagag ctgatccttg ggacttgcct     180
ggcaatttgg agaaggagag gtacttcttc agcacaaggg aagccaagta cccaaatggg     240
aaccggtcta accgagcaac cggttcgggt tattggaaag ctaccggtat tgataaacgg     300
ttgtgacct tcgaggaaa tcaaatcgtt ggtttgaaga aaacactcgt tttctacaaa      360
ggcaaaccac ctcatggctc aagaaccgat tggatcatgc atgaatatcg tctctcttcc     420
tctcctccga gttcaatggg tcctactcag aactgggttc tttgtcgtat cttccttaaa     480
aagagagctg gcagcaagag cgacggcgac gagggagata ccggaatat aagatatgat      540
aatgaccata ttgaaataat tacaacaaac caaactgaag ataaaactaa accaatcttc     600
ttcgatttca tgagaaaaga aaggaccaca gacttgaacc ttttgccaag ctcttcttct     660
tccgaccacg cttcaagtgg actcacgacg gagatattct cttctgatga agagaccagt     720
agttgcaata gtttcagacg aaatctttaa                                     750

<210> SEQ ID NO 9
```

<211> LENGTH: 249
<212> TYPE: PRT
<213> ORGANISM: Brassica napus

<400> SEQUENCE: 9

Met Asp Lys Val Lys Leu Val Lys Asn Gly Val Met Arg Leu Pro Pro
1               5                   10                  15

Gly Phe Arg Phe His Pro Thr Asp Glu Glu Leu Val Val Gln Tyr Leu
            20                  25                  30

Lys Arg Lys Val Leu Ser Ser Pro Leu Pro Ala Ser Ile Ile Pro Asp
        35                  40                  45

Phe Asp Val Cys Arg Ala Asp Pro Trp Asp Leu Pro Gly Asn Leu Glu
50                  55                  60

Lys Glu Arg Tyr Phe Phe Ser Thr Arg Glu Ala Lys Tyr Pro Asn Gly
65                  70                  75                  80

Asn Arg Ser Asn Arg Ala Thr Gly Ser Gly Tyr Trp Lys Ala Thr Gly
                85                  90                  95

Ile Asp Lys Arg Val Val Thr Ser Arg Gly Asn Gln Ile Val Gly Leu
            100                 105                 110

Lys Lys Thr Leu Val Phe Tyr Lys Gly Lys Pro Pro His Gly Ser Arg
        115                 120                 125

Thr Asp Trp Ile Met His Glu Tyr Arg Leu Ser Ser Ser Pro Pro Ser
130                 135                 140

Ser Met Gly Pro Thr Gln Asn Trp Val Leu Cys Arg Ile Phe Leu Lys
145                 150                 155                 160

Lys Arg Ala Gly Ser Lys Ser Asp Gly Asp Glu Gly Asp Asn Arg Asn
                165                 170                 175

Ile Arg Tyr Asp Asn Asp His Ile Glu Ile Ile Thr Thr Asn Gln Thr
            180                 185                 190

Glu Asp Lys Thr Lys Pro Ile Phe Phe Asp Phe Met Arg Lys Glu Arg
        195                 200                 205

Thr Thr Asp Leu Asn Leu Leu Pro Ser Ser Ser Ser Asp His Ala
210                 215                 220

Ser Ser Gly Leu Thr Thr Glu Ile Phe Ser Ser Asp Glu Glu Thr Ser
225                 230                 235                 240

Ser Cys Asn Ser Phe Arg Arg Asn Leu
                245

<210> SEQ ID NO 10
<211> LENGTH: 1067
<212> TYPE: DNA
<213> ORGANISM: Glycine max

<400> SEQUENCE: 10 cttttccct ctccataccc ttttgctttc tttatccaat aataagaact tcccacgagt      60
ggctttaact ggtctggtct ggtctggtct ggtcggacac acaaaaatat tagtatggag    120
aaggtgagtt ttgtgaagaa tggagagctt agattgcctc cggggtttcg tttccacccg    180
actgatgagg agctggtttt gcagtacttg aagcgcaagg tcttctcctg ccctctgcca    240
gcctctatca ttcctgaggt tgatgttttgc aagtctgatc cttgggattt gccaggtgat    300
ttggagcaag agagatactt ctttagcacc aaagaggcca aatatcccaa cggaaatcgc    360
tctaacagag ccacaaattc gggttattgg aaggcaactg gcttggacaa acaaattgtt    420
acttcaaaag ggaaccaagt tgtggggatg aagaagacac ttgttttcta cagaggcaag    480
cctcctcatg gatccagaac tgattggatc atgcatgagt atcgcctcaa catccttaac    540

```
gcctctcaga gccatgttcc catggaaaat tgggttctat gtcgcatatt tttgaagaag    600
agaagcggtg ctaaaaatgg ggaggagagc aacaaggtga ggaactctaa ggtggttttc    660
tatgacttcc tagcgcagaa caagactgat tcctcatcct cggccgccag tggaattaca    720
catgaacatg aatcagatga acatgaccat gaagagagca gtagctccaa caccttccct    780
tatactatta gaacgaaacc ttaacaacca agtcaacaac caccttcctt aaaaagttga    840
ttatcaccta gttttttttt ttttaattct ctttcccttt ccctgtaatc atcaacaacc    900
acttgttgaa aggaagcatc cctcccaatg agaccggcat tagttaaagg gtagcctgca    960
gagtatggta ctgatagtag cagtgtgtaa tggactcccc attttccttc aatttaacct   1020 tttttttctaa tgcccatgct tcttctttta aaaaaaaaaa aaaaaaa               1067
```

<210> SEQ ID NO 11
<211> LENGTH: 229
<212> TYPE: PRT
<213> ORGANISM: Glycine max

<400> SEQUENCE: 11

```
Met Glu Lys Val Ser Phe Val Lys Asn Gly Glu Leu Arg Leu Pro Pro
  1               5                  10                  15

Gly Phe Arg Phe His Pro Thr Asp Glu Glu Leu Val Leu Gln Tyr Leu
                 20                  25                  30

Lys Arg Lys Val Phe Ser Cys Pro Leu Pro Ala Ser Ile Ile Pro Glu
             35                  40                  45

Val Asp Val Cys Lys Ser Asp Pro Trp Asp Leu Pro Gly Asp Leu Glu
 50                  55                  60

Gln Glu Arg Tyr Phe Phe Ser Thr Lys Glu Ala Lys Tyr Pro Asn Gly
 65                  70                  75                  80

Asn Arg Ser Asn Arg Ala Thr Asn Ser Gly Tyr Trp Lys Ala Thr Gly
                 85                  90                  95

Leu Asp Lys Gln Ile Val Thr Ser Lys Gly Asn Gln Val Val Gly Met
            100                 105                 110

Lys Lys Thr Leu Val Phe Tyr Arg Gly Lys Pro Pro His Gly Ser Arg
            115                 120                 125

Thr Asp Trp Ile Met His Glu Tyr Arg Leu Asn Ile Leu Asn Ala Ser
130                 135                 140

Gln Ser His Val Pro Met Glu Asn Trp Val Leu Cys Arg Ile Phe Leu
145                 150                 155                 160

Lys Lys Arg Ser Gly Ala Lys Asn Gly Glu Glu Ser Asn Lys Val Arg
                165                 170                 175

Asn Ser Lys Val Val Phe Tyr Asp Phe Leu Ala Gln Asn Lys Thr Asp
            180                 185                 190

Ser Ser Ser Ser Ala Ala Ser Gly Ile Thr His Glu His Glu Ser Asp
            195                 200                 205

Glu His Asp His Glu Glu Ser Ser Ser Asn Thr Phe Pro Tyr Thr
            210                 215                 220

Ile Arg Thr Lys Pro
225
```

<210> SEQ ID NO 12
<211> LENGTH: 870
<212> TYPE: DNA
<213> ORGANISM: Glycine max

<400> SEQUENCE: 12

```
acacaaaaat attattagca tggacaaggt gaattttgtg aagaatggag agcttagatt      60
gcctccgggg ttccgtttcc acccgactga tgaggagctg ttctgcaat acttgaagcg     120
caaggtcttc tcctgccctt tgccagcctc tatcattcct gagcttcatg tttgcaagtc    180
tgatccttgg gatttgccag gtgatttgga gcaagagaga tacttcttta gcaccaaagt    240
ggccaaatat cccaacggaa atcgctccaa cagagccaca aattcgggtt attggaaggc    300
aactggcttg gacaaacaaa ttgttacttc aaaaggcaac aaccaagttg tcggaatgaa    360
gaagacactt gttttctaca gaggcaagcc tcctaatgga tccagaactg attggatcat    420
gcacgagtat cgcctcatcc ttaacgcctc tcagtctcag agccatgttg ttcccatgga    480
aaattgggtt ctgtgtcgca tattttgaa gaggagaatt ggtgctaaaa atggggagga    540
gagcaactct aaggtggttt tctatgactt cttagcgcag aacaagaccg attcctcctc    600
atcggtcgcc agtggaatta cacatgaatc agatgaacat gaagagagca gtagctccaa    660
cccttccct tatactatta aagaaaacc ttaacaacct tccttaaaaa tttaagttca     720
ttatctagtt gttgttttta attgtctttc cctttccctg taattatcat caatcacttg    780
ttgaaaggaa gcatcctctt cccaaatgag accggcatta agggtagtct ggagagtatg    840
gtactaatac tagtagtagt gtgtaataca                                      870
```

<210> SEQ ID NO 13
<211> LENGTH: 224
<212> TYPE: PRT
<213> ORGANISM: Glycine max

<400> SEQUENCE: 13

```
Met Asp Lys Val Asn Phe Val Lys Asn Gly Glu Leu Arg Leu Pro Pro
 1               5                  10                  15

Gly Phe Arg Phe His Pro Thr Asp Glu Glu Leu Val Leu Gln Tyr Leu
            20                  25                  30

Lys Arg Lys Val Phe Ser Cys Pro Leu Pro Ala Ser Ile Ile Pro Glu
        35                  40                  45

Leu His Val Cys Lys Ser Asp Pro Trp Asp Leu Pro Gly Asp Leu Glu
    50                  55                  60

Gln Glu Arg Tyr Phe Phe Ser Thr Lys Val Ala Lys Tyr Pro Asn Gly
65                  70                  75                  80

Asn Arg Ser Asn Arg Ala Thr Asn Ser Gly Tyr Trp Lys Ala Thr Gly
                85                  90                  95

Leu Asp Lys Gln Ile Val Thr Ser Lys Gly Asn Asn Gln Val Val Gly
           100                 105                 110

Met Lys Lys Thr Leu Val Phe Tyr Arg Gly Lys Pro Pro Asn Gly Ser
       115                 120                 125

Arg Thr Asp Trp Ile Met His Glu Tyr Arg Leu Ile Leu Asn Ala Ser
   130                 135                 140

Gln Ser Gln Ser His Val Val Pro Met Glu Asn Trp Val Leu Cys Arg
145                 150                 155                 160

Ile Phe Leu Lys Arg Arg Ile Gly Ala Lys Asn Gly Glu Glu Ser Asn
                165                 170                 175

Ser Lys Val Val Phe Tyr Asp Phe Leu Ala Gln Asn Lys Thr Asp Ser
            180                 185                 190

Ser Ser Ser Val Ala Ser Gly Ile Thr His Glu Ser Asp Glu His Glu
        195                 200                 205

Glu Ser Ser Ser Ser Asn Thr Phe Pro Tyr Thr Ile Arg Arg Lys Pro
```

<210> SEQ ID NO 14
<211> LENGTH: 743
<212> TYPE: DNA
<213> ORGANISM: Helianthus annuus

<400> SEQUENCE: 14

```
acatcacatg gagaagctgc aaaacgcaaa tgctgtgctg cggagattgc ctcccggttt      60
caggcttcac ccaacagatg aagaacttgt tgtacaatac ttaaagcgca gggtccactc     120
ttctcctctg cctgcttcca tcatccctga ggtggatgtc tgcaagtctg atccatggga     180
cctgcccgga gactctgatc agcaggagga gaggttcttc tttagcacca gagagatcaa     240
gtaccccaat ggaaaccgat ccaacagggc cacccaatcc ggttactgga agcaaccgg      300
cctgagtagg caaattatgg gggccaacca agttggattg gttggcatca agaaaactct     360
agttttctat aagggaaagc cccccaccgg ctcccgaact gattggatca tgcatgagta     420
tcgtcttgct accacgcaac caactcaggg tctggaaaag tgggtactgt gcaaaatctt     480
tttgaagaaa agagggaact acaaggacga gaaaaaaaat gtgccggttt tctatgattt     540
tctggctaca cccaaggtga agacgtcgtc gtcgtcgtca tcaggctcaa gtgggatcac     600
agaagagagc agcacaaatt gttaattagg agaaatgaag aataatgttt cttagttttc     660
tagtactagt atcgatgttg gagttgaaat ttagatagag tttgtaatct catcttgtta     720
agtgttaact tgacttttg ccc                                              743
```

<210> SEQ ID NO 15
<211> LENGTH: 205
<212> TYPE: PRT
<213> ORGANISM: Helianthus annuus

<400> SEQUENCE: 15

```
Met Glu Lys Leu Gln Asn Ala Asn Ala Val Leu Arg Arg Leu Pro Pro
  1               5                  10                  15

Gly Phe Arg Leu His Pro Thr Asp Glu Glu Leu Val Val Gln Tyr Leu
             20                  25                  30

Lys Arg Val His Ser Ser Pro Leu Pro Ala Ser Ile Ile Pro Glu
         35                  40                  45

Val Asp Val Cys Lys Ser Asp Pro Trp Asp Leu Pro Gly Asp Ser Asp
 50                  55                  60

Gln Gln Glu Glu Arg Phe Phe Ser Thr Arg Glu Ile Lys Tyr Pro
65                  70                  75                  80

Asn Gly Asn Arg Ser Asn Arg Ala Thr Gln Ser Gly Tyr Trp Lys Ala
                 85                  90                  95

Thr Gly Leu Ser Arg Gln Ile Met Gly Ala Asn Gln Val Gly Leu Val
            100                 105                 110

Gly Ile Lys Lys Thr Leu Val Phe Tyr Lys Gly Lys Pro Pro Thr Gly
        115                 120                 125

Ser Arg Thr Asp Trp Ile Met His Glu Tyr Arg Leu Ala Thr Thr Gln
130                 135                 140

Pro Thr Gln Gly Leu Glu Lys Trp Val Leu Cys Lys Ile Phe Leu Lys
145                 150                 155                 160

Lys Arg Gly Asn Tyr Lys Asp Glu Lys Lys Asn Val Pro Val Phe Tyr
                165                 170                 175

Asp Phe Leu Ala Thr Pro Lys Val Lys Thr Ser Ser Ser Ser Ser
            180                 185                 190
```

```
Gly Ser Ser Gly Ile Thr Glu Glu Ser Ser Thr Asn Cys
        195                 200                 205

<210> SEQ ID NO 16
<211> LENGTH: 474
<212> TYPE: DNA
<213> ORGANISM: Arabidopsis thaliana

<400> SEQUENCE: 16
atggcaaacg cagagaagac aagttcaggt tccgacatag atgagaagaa aagaaaacgc        60
aagttatcaa accgcgaatc tgcaaggagg tcgcgtttga agaaacagaa gttaatggaa       120
gacacgattc atgagatctc cagtcttgaa cgacgaatca agagaacag tgagagatgt        180 cgagctgtaa aacagaggct tgactcggtc gaaacggaga cgcgggtct tagatcggag        240 aagatttggc tctcgagtta cgttagcgat ttagagaata tgattgctac gacgagttta       300
acgctgacgc agagtggtgg tggcgattgt gtcgacgatc agaacgcaaa cgcgggaata       360
gcggttggag attgtagacg tacaccgtgg aaattgagtt gtggttctct acaaccaatg       420
gcgtccttta agacatgaga tttgtgtatt agtgtgtgtt ttactttggt catt             474

<210> SEQ ID NO 17
<211> LENGTH: 145
<212> TYPE: PRT
<213> ORGANISM: Arabidopsis thaliana

<400> SEQUENCE: 17

Met Ala Asn Ala Glu Lys Thr Ser Ser Gly Ser Asp Ile Asp Glu Lys
  1               5                  10                  15

Lys Arg Lys Arg Lys Leu Ser Asn Arg Glu Ser Ala Arg Arg Ser Arg
             20                  25                  30

Leu Lys Lys Gln Lys Leu Met Glu Asp Thr Ile His Glu Ile Ser Ser
         35                  40                  45

Leu Glu Arg Arg Ile Lys Glu Asn Ser Glu Arg Cys Arg Ala Val Lys
     50                  55                  60

Gln Arg Leu Asp Ser Val Glu Thr Glu Asn Ala Gly Leu Arg Ser Glu
 65                  70                  75                  80

Lys Ile Trp Leu Ser Ser Tyr Val Ser Asp Leu Glu Asn Met Ile Ala
                 85                  90                  95

Thr Thr Ser Leu Thr Leu Thr Gln Ser Gly Gly Gly Asp Cys Val Asp
            100                 105                 110

Asp Gln Asn Ala Asn Ala Gly Ile Ala Val Gly Asp Cys Arg Arg Thr
        115                 120                 125

Pro Trp Lys Leu Ser Cys Gly Ser Leu Gln Pro Met Ala Ser Phe Lys
    130                 135                 140

Thr
145

<210> SEQ ID NO 18
<211> LENGTH: 907
<212> TYPE: DNA
<213> ORGANISM: Arabidopsis thaliana

<400> SEQUENCE: 18
ttctcccact ttccttattt tcgatcttat ccttatcttc ttccttgttc tatttctctt        60
ctaactaatc tcttctcttc tcttaaaatc aaacgtaatc ataaataaag atcttcttgt       120
ttaatttctc ttgatcctcg caaaatcaca gattcttgaa attcttttttt cttgtcttga      180
```

```
aattcttgag ttcttgagtt atgaaaagac aatggacaga gttatgaaat gataaatctc      240
aaccaattcc ttgtttatca ttctatatca gttgtgattc ttcattggtt ttacgttatc      300
tcttgaacaa aaaaacatgg caaacgcaga aagacaagt tcaggttccg acatagatga       360
gaagaaaaga aaacgcaagt tatcaaaccg cgaatctgca aggaggtcgc gtttgaagaa      420
acagaagtta atggaagaca cgattcatga gatctccagt cttgaacgac gaatcaaaga     480
gaacagtgag agatgtcgag ctgtaaaaca gaggcttgac tcggtcgaaa cggagaacgc     540
gggtcttaga tcggagaaga tttggctctc gagttacgtt agcgatttag agaatatgat     600
tgctacgacg agtttaacgc tgacgcagag tggtggtggc gattgtgtcg acgatcagaa     660
cgcaaacgcg ggaatagcgg ttggagattg tagacgtaca ccgtggaaat tgagttgtgg     720
ttctctacaa ccaatggcgt cctttaagac atgagatttg tgtattagtg tgtgttttac    780
tttggtcatt ttatagtttt tgtaatcttt ttatatcgaa ttgtttcttc tcattacttt     840
ctgaattctg atacaattgc atatcttatt gttttcaaca ttttcattta acgttatatg     900
attttcg                                                                907

<210> SEQ ID NO 19
<211> LENGTH: 143
<212> TYPE: PRT
<213> ORGANISM: Arabidopsis thaliana

<400> SEQUENCE: 19

Met Ala Asn Ala Glu Lys Thr Ser Ser Gly Ser Asp Ile Asp Glu Lys
 1               5                  10                  15

Lys Arg Lys Arg Lys Leu Ser Asn Arg Glu Ser Ala Arg Arg Ser Arg
             20                  25                  30

Leu Lys Lys Gln Lys Leu Met Glu Asp Thr Ile His Glu Ile Ser Ser
         35                  40                  45

Leu Glu Arg Arg Ile Lys Glu Asn Ser Glu Arg Cys Arg Ala Val Lys
     50                  55                  60

Gln Arg Leu Asp Ser Val Glu Thr Glu Asn Ala Gly Leu Arg Ser Glu
 65                  70                  75                  80

Lys Ile Trp Leu Ser Ser Tyr Val Ser Asp Leu Glu Asn Met Ile Ala
                 85                  90                  95

Thr Thr Ser Leu Thr Leu Thr Gln Ser Gly Gly Gly Asp Cys Val Asp
            100                 105                 110

Asp Gln Asn Ala Asn Ala Gly Ile Gly Asp Cys Arg Arg Thr Pro Trp
        115                 120                 125

Lys Leu Ser Cys Gly Ser Leu Gln Pro Met Ala Ser Phe Lys Thr
    130                 135                 140

<210> SEQ ID NO 20
<211> LENGTH: 838
<212> TYPE: DNA
<213> ORGANISM: Populus trichocarpa

<400> SEQUENCE: 20
cctccgcacc tttcctattt cctcttccat taattaactc tttcaggatt ttccttccct       60
ttcctttttc ttattcacag gattttagtc atgttttcaa aatcatagac ctttcttgca      120
tgatatgaac catctcagac tgttctgtcg aatgaaaatt tcccattcag tatcagttgt      180
ccttctgtat tggttctatg tcttttcttg aacttgtcta attttcagtc tcacacaaca      240
acatttacgt tttcattatt taaggctagc tagcaaccgt agttatatat tataatcagt      300
```

-continued

```
ccagtgatca atcaaagaaa atgccaccat cctttgcaaa ggcaggttcg tcaggctctg    360
aaattgaccc accaaatgct atggttgatg agaagagaag aaaaagaatg atctcaaata    420
gagaatctgc aaggcggtcg agaatgaaga ggcaaaagta tatggaagat ttggttactg    480
aaaaatctat cttggagaga agatatatg aagacaataa aaaatatgct gcactttggc     540
aaaggcattt tgctctcgaa tcagacaaca aagttttgac ggatgaaaag ttgaagctgg    600
cagaatattt gaagaacttg caacaagttc ttgcaagtta taatgtcatt gaatctgatc    660
aggatctaga agtttcagac cgattttga acccatggca agttcatggt tcagtgaagt     720
ccatcacagc ttctgggatg ttcaaagttt agttgttcta gttttatttc catgatttat    780
tgtcttggga ttgagctttt gatttctctg gttatgctgt tcacatttgt ttcggttt      838
```

<210> SEQ ID NO 21
<211> LENGTH: 143
<212> TYPE: PRT
<213> ORGANISM: Populus trichocarpa

<400> SEQUENCE: 21

```
Met Pro Pro Ser Phe Ala Lys Ala Gly Ser Ser Gly Ser Glu Ile Asp
 1               5                  10                  15

Pro Pro Asn Ala Met Val Asp Glu Lys Arg Arg Lys Arg Met Ile Ser
            20                  25                  30

Asn Arg Glu Ser Ala Arg Arg Ser Arg Met Lys Arg Gln Lys Tyr Met
        35                  40                  45

Glu Asp Leu Val Thr Glu Lys Ser Ile Leu Glu Arg Lys Ile Tyr Glu
    50                  55                  60

Asp Asn Lys Lys Tyr Ala Ala Leu Trp Gln Arg His Phe Ala Leu Glu
65                  70                  75                  80

Ser Asp Asn Lys Val Leu Thr Asp Glu Lys Leu Lys Leu Ala Glu Tyr
                85                  90                  95

Leu Lys Asn Leu Gln Gln Val Leu Ala Ser Tyr Asn Val Ile Glu Ser
            100                 105                 110

Asp Gln Asp Leu Glu Val Ser Asp Arg Phe Leu Asn Pro Trp Gln Val
        115                 120                 125

His Gly Ser Val Lys Ser Ile Thr Ala Ser Gly Met Phe Lys Val
    130                 135                 140
```

<210> SEQ ID NO 22
<211> LENGTH: 1235
<212> TYPE: DNA
<213> ORGANISM: Glycine max

<400> SEQUENCE: 22

```
ctctaaccaa gtagaagtgc aataattaaa tgtccaacat cttcttgttg ttgatgtttg     60
agattcatgt atccgattct cagtgaaatc ttcttttccg ggtgtatgat caattccact    120
gctaggcgca ggacccattt agttcaatcc ttctcagttg ccttcctcta ttggttgtac    180
tacgtttcat gatttctaac ccttccttag cttaataatc atctatctaa aatatcataa    240
tatcttctac tagctagttt tatttttatt atcacaataa aatctatctg caatatattg    300
ttatttttat tttctgagaa atttgtgtct agttataagt gtctgggtcc tggtcctgcc    360
tattgtgtca attaaattga gaagggttgt attgcataga atcatatatc gtatcatata    420
aacatgcgtt gttcaagtgg aacatcttca gggtcattat ctctgcttca gaactctggt    480
tctgaggaag atttgcaggc gatgatggaa gatcagagaa agaggaagag aatgatatca    540
```

```
aaccgcgaat ctgcacgccg atctcgcatg aggaagcaga agcacttgga cgatcttgtt      600
tcccaagtgg ctcagctcag aaagagaac caacaaatac tcacaagcgt caacatcacc       660
acgcaacagt acttaagcgt tgaggctgag aactcggtgc ttagggctca ggtgggtgag      720
ttgagtcaca ggttggagtc tctgaacgag atcgttgacg tgttgaatgc caccaccact     780
gtggcgggtt ttggagcagc agcatcgagc accttcgttg agccaatgaa taataataat    840
aatagcttct tcaacttcaa cccgttgaat atggggtatc tgaaccagcc tattatggct    900
tctgcagaca tattgcagta ttgattgaga tgcttcatct ctgagatttg atgaggattt     960
cttcttcttc ttcttctggg tttgagtctg tcgagaaatt gtaatcacta ccatatgatg    1020
gtgataagga ataatattaa taatgaatgt gtatcataaa aacgggtggg attgttaatg   1080
ttaggtgctg gttccgtaaa tggggcatgg ggcatgggcc attactgtaa tttgtcaccc   1140
tcctttccta tataataata ataataataa taataatact gccctctcta tgttattatt   1200
ctccccaaaa aaaaaaaaaa aaaaaaaaaa aaaa                                 1235
```

<210> SEQ ID NO 23
<211> LENGTH: 166
<212> TYPE: PRT
<213> ORGANISM: Glycine max

<400> SEQUENCE: 23

```
Met Ala Cys Ser Ser Gly Thr Ser Ser Gly Ser Leu Ser Leu Leu Gln
 1               5                  10                  15

Asn Ser Gly Ser Glu Glu Asp Leu Gln Ala Met Met Glu Asp Gln Arg
            20                  25                  30

Lys Arg Lys Arg Met Ile Ser Asn Arg Glu Ser Ala Arg Arg Ser Arg
        35                  40                  45

Met Arg Lys Gln Lys His Leu Asp Asp Leu Val Ser Gln Val Ala Gln
    50                  55                  60

Leu Arg Lys Glu Asn Gln Gln Ile Leu Thr Ser Val Asn Ile Thr Thr
65                  70                  75                  80

Gln Gln Tyr Leu Ser Val Glu Ala Glu Asn Ser Val Leu Arg Ala Gln
                85                  90                  95

Val Gly Glu Leu Ser His Arg Leu Glu Ser Leu Asn Glu Ile Val Asp
           100                 105                 110

Val Leu Asn Ala Thr Thr Thr Val Ala Gly Phe Gly Ala Ala Ala Ser
       115                 120                 125

Ser Thr Phe Val Glu Pro Met Asn Asn Asn Asn Ser Phe Phe Asn
   130                 135                 140

Phe Asn Pro Leu Asn Met Gly Tyr Leu Asn Gln Pro Ile Met Ala Ser
145                 150                 155                 160

Ala Asp Ile Leu Gln Tyr
                165
```

<210> SEQ ID NO 24
<211> LENGTH: 147
<212> TYPE: PRT
<213> ORGANISM: Sorghum bicolor

<400> SEQUENCE: 24

```
Met Ser Ser Ser Arg Arg Ser Ser Ser Pro Asp Ser Asn Asn Asn Thr
 1               5                  10                  15

Asp Val Ser Gly Gly Gly Gly Gly Gly Phe Ala Ala Asp Glu Arg Lys
            20                  25                  30
```

Arg Lys Arg Met Leu Ser Asn Arg Glu Ser Ala Arg Ser Arg Ala
            35                  40                  45

Lys Lys Gln Gln Arg Leu Glu Glu Leu Val Ala Glu Val Ala Arg Leu
 50                  55                  60

Gln Ala Glu Asn Ala Ala Ala Gln Ser Arg Ile Ala Ala Phe Glu Arg
 65                  70                  75                  80

Glu Phe Ala Lys Val Asp Gly Asp Asn Ala Val Leu Arg Ala Arg His
                 85                  90                  95

Gly Glu Leu Ser Ser Arg Leu Glu Ser Leu Gly Gly Val Leu Glu Val
            100                 105                 110

Leu Gln Met Ala Gly Ala Ala Val Asp Ile Pro Glu Met Val Thr Glu
            115                 120                 125

Asp Pro Met Leu Arg Pro Trp Gln Pro Ser Phe Pro Pro Met Gln Pro
130                 135                 140

Ile Gly Phe
145

<210> SEQ ID NO 25
<211> LENGTH: 152
<212> TYPE: PRT
<213> ORGANISM: Capsella rubella

<400> SEQUENCE: 25

Met Ala Asn Ala Glu Lys Thr Thr Thr Ser Ser Gly Ser Asp Ile Asp
 1               5                   10                  15

Glu Lys Lys Arg Lys Arg Lys Leu Ser Asn Arg Glu Ser Ala Arg Arg
            20                  25                  30

Ser Arg Leu Lys Lys Gln Lys Gln Met Glu Asp Thr Ile His Glu Ile
            35                  40                  45

Ser Ser Leu Glu Arg Arg Ile Lys Glu Asn Gly Glu Arg Cys Lys Val
 50                  55                  60

Val Lys Glu Arg Leu Asp Ser Leu Glu Thr Glu Asn Ala Leu Leu Arg
 65                  70                  75                  80

Ser Glu Lys Thr Trp Leu Ser Ser Tyr Val Cys Asp Leu Glu Asn Met
                 85                  90                  95

Ile Ala Thr Thr Thr Leu Thr Leu Thr His Ser Gly Gly Gly Gly Gly
            100                 105                 110

Cys Asp Gly Asp Glu Asp Glu Asn Ala Asn Ala Glu Ile Ala Val Gly
            115                 120                 125

Asp Cys Arg Arg Arg Arg Pro Trp Lys Leu Leu Ser Cys Asp Ser Leu
130                 135                 140

Gln Pro Met Ala Ser Phe Lys Thr
145                 150

<210> SEQ ID NO 26
<211> LENGTH: 843
<212> TYPE: DNA
<213> ORGANISM: Arabidopsis thaliana

<400> SEQUENCE: 26
atgaggaagc cagaggtagc cattgcagct agtactcacc aagtaaagaa gatgaagaag      60
ggactttggt ctcctgagga agactcaaag ctgatgcaat acatgttaag caatggacaa     120
ggatgttgga gtgatgttgc gaaaaacgca ggacttcaaa gatgtggcaa aagctgccgt     180
cttcgttgga tcaactatct tcgtcctgac ctcaagcgtg gcgctttctc tcctcaagaa     240

-continued

```
gaggatctca tcattcgctt tcattccatc ctcggcaaca ggtggtctca gattgcagca      300
cgattgcctg gtcggaccga taacgagatc aagaatttct ggaactcaac aataaagaaa      360
aggctaaaga agatgtccga tacctccaac ttaatcaaca actcatcctc atcacccaac      420
acagcaagcg attcctcttc taattccgca tcttctttgg atattaaaga cattataggg      480
agcttcatgt ccttacaaga acaaggcttc gtcaaccctt ccttgaccca catacaaacc      540
aacaatccat ttccaacggg aaacatgatc agccacccgt gcaatgacga ttttaccct       600 tatgtagatg gtatctatgg agtaaacgca ggggtacaag gggaactcta cttcccacct      660
ttggaatgtg aagaaggtga ttggtacaat gcaaatataa acaaccactt agacgagttg      720
aacactaatg gatccggaaa cgcacctgag ggtatgagac cagtggaaga attttgggac      780
cttgaccagt tgatgaacac tgaggttcct tcgttttact tcaacttcaa acaaagcata      840
tga                                                                    843
```

<210> SEQ ID NO 27
<211> LENGTH: 280
<212> TYPE: PRT
<213> ORGANISM: Arabidopsis thaliana

<400> SEQUENCE: 27

```
Met Arg Lys Pro Glu Val Ala Ile Ala Ala Ser Thr His Gln Val Lys
  1               5                  10                  15

Lys Met Lys Lys Gly Leu Trp Ser Pro Glu Asp Ser Lys Leu Met
             20                  25                  30

Gln Tyr Met Leu Ser Asn Gly Gln Gly Cys Trp Ser Asp Val Ala Lys
         35                  40                  45

Asn Ala Gly Leu Gln Arg Cys Gly Lys Ser Cys Arg Leu Arg Trp Ile
     50                  55                  60

Asn Tyr Leu Arg Pro Asp Leu Lys Arg Gly Ala Phe Ser Pro Gln Glu
 65                  70                  75                  80

Glu Asp Leu Ile Ile Arg Phe His Ser Ile Leu Gly Asn Arg Trp Ser
                 85                  90                  95

Gln Ile Ala Ala Arg Leu Pro Gly Arg Thr Asp Asn Glu Ile Lys Asn
            100                 105                 110

Phe Trp Asn Ser Thr Ile Lys Lys Arg Leu Lys Lys Met Ser Asp Thr
        115                 120                 125

Ser Asn Leu Ile Asn Asn Ser Ser Ser Ser Pro Asn Thr Ala Ser Asp
    130                 135                 140

Ser Ser Ser Asn Ser Ala Ser Ser Leu Asp Ile Lys Asp Ile Ile Gly
145                 150                 155                 160

Ser Phe Met Ser Leu Gln Glu Gln Gly Phe Val Asn Pro Ser Leu Thr
                165                 170                 175

His Ile Gln Thr Asn Asn Pro Phe Pro Thr Gly Asn Met Ile Ser His
            180                 185                 190

Pro Cys Asn Asp Asp Phe Thr Pro Tyr Val Asp Gly Ile Tyr Gly Val
        195                 200                 205

Asn Ala Gly Val Gln Gly Glu Leu Tyr Phe Pro Pro Leu Glu Cys Glu
    210                 215                 220

Glu Gly Asp Trp Tyr Asn Ala Asn Ile Asn Asn His Leu Asp Glu Leu
225                 230                 235                 240

Asn Thr Asn Gly Ser Gly Asn Ala Pro Glu Gly Met Arg Pro Val Glu
                245                 250                 255

Glu Phe Trp Asp Leu Asp Gln Leu Met Asn Thr Glu Val Pro Ser Phe
```

Tyr Phe Asn Phe Lys Gln Ser Ile
            275                 280

<210> SEQ ID NO 28
<211> LENGTH: 993
<212> TYPE: DNA
<213> ORGANISM: Glycine max

<400> SEQUENCE: 28

```
atgaacaaca acattaagag caagctaagg aagggattgt ggtcacctga ggaagatgaa    60
aaactcctaa ggtacatgat cactaaggga caagggtgtt ggagtgacat tgctaggaat   120
gctggccttc aaaggtgcgg caagagttgc cggcttcgtt ggattaacta cttgagacct   180
gatctcaaac gtggtgcatt ttcaccccaa gaggaagaac tcatcattca tttgcactct   240
attcttggca cagatggtc tcagattgcg gcacgtctcc ctggtcgcac agacaatgag    300
atcaagaatt tctggaactc cactctgaag aaaaggttga aatgaacaa caatattaac    360
gccacttcat caccaaacaa tagctactca tcatcagagc ctagagatgt caatgtcatg   420
ggtgggatca tgcccatgaa cgagcatgac ctcatgacca tgtgcatgga ctcctcctca   480
tcaacatcat catcatgcat gcaatccatg catacaacca acatggtact aactgaccaa   540
tttgatccct ttcccttgtt gtccaacaac cgttacgaca tgaccggcgc aaccgatttc   600
cttgacaaca tggctgcatg cttaacccaa gttggcatgg tagatcatga tcatggggtt   660
gttcatgatg gttatgggac attggagcct aacaaaacgg gtttagaaag tgacttttcc   720
cttcctccac tagaaagtag aagcattgac gacaatagta gtaccccaat tgatcatgtg   780
aaaagccata caacaacaa ccacttcaag aatagttgct tcaataacac tgatcatcac   840
catcatatcc aatgctccaa caacgtagtt gtagaggatt tgtttgggtt tggaaatcat   900
ggacatggag aaagctttag aatggaagaa tgggactttg agggtttgat tcaagatatt   960
ccctattttt cttcccttga tttccaagtt taa                                993
```

<210> SEQ ID NO 29
<211> LENGTH: 330
<212> TYPE: PRT
<213> ORGANISM: Glycine max

<400> SEQUENCE: 29

Met Asn Asn Asn Ile Lys Ser Lys Leu Arg Lys Gly Leu Trp Ser Pro
1               5                   10                  15

Glu Glu Asp Glu Lys Leu Leu Arg Tyr Met Ile Thr Lys Gly Gln Gly
            20                  25                  30

Cys Trp Ser Asp Ile Ala Arg Asn Ala Gly Leu Gln Arg Cys Gly Lys
        35                  40                  45

Ser Cys Arg Leu Arg Trp Ile Asn Tyr Leu Arg Pro Asp Leu Lys Arg
    50                  55                  60

Gly Ala Phe Ser Pro Gln Glu Glu Glu Leu Ile Ile His Leu His Ser
65                  70                  75                  80

Ile Leu Gly Asn Arg Trp Ser Gln Ile Ala Ala Arg Leu Pro Gly Arg
                85                  90                  95

Thr Asp Asn Glu Ile Lys Asn Phe Trp Asn Ser Thr Leu Lys Lys Arg
            100                 105                 110

Leu Lys Met Asn Asn Asn Ile Asn Ala Thr Ser Ser Pro Asn Asn Ser
        115                 120                 125

```
Tyr Ser Ser Glu Pro Arg Asp Val Asn Val Met Gly Gly Ile Met
    130                 135                 140

Pro Met Asn Glu His Asp Leu Met Thr Met Cys Met Asp Ser Ser
145                 150                 155                 160

Ser Thr Ser Ser Ser Cys Met Gln Ser Met His Thr Thr Asn Met Val
                165                 170                 175

Leu Thr Asp Gln Phe Asp Pro Phe Pro Leu Leu Ser Asn Asn Arg Tyr
            180                 185                 190

Asp Met Thr Gly Ala Thr Asp Phe Leu Asp Asn Met Ala Ala Cys Leu
            195                 200                 205

Thr Gln Val Gly Met Val Asp His Asp His Gly Val Val His Asp Gly
    210                 215                 220

Tyr Gly Thr Leu Glu Pro Asn Lys Thr Gly Leu Glu Ser Asp Phe Ser
225                 230                 235                 240

Leu Pro Pro Leu Glu Ser Arg Ser Ile Asp Asp Asn Ser Ser Thr Pro
                245                 250                 255

Ile Asp His Val Lys Ser His Asn Asn Asn His Phe Lys Asn Ser
            260                 265                 270

Cys Phe Asn Asn Thr Asp His His His Ile Gln Cys Ser Asn Asn
    275                 280                 285

Val Val Val Glu Asp Leu Phe Gly Phe Gly Asn His Gly His Gly Glu
290                 295                 300

Ser Phe Arg Met Glu Glu Trp Asp Phe Glu Gly Leu Ile Gln Asp Ile
305                 310                 315                 320

Pro Tyr Phe Ser Ser Leu Asp Phe Gln Val
            325                 330

<210> SEQ ID NO 30
<211> LENGTH: 321
<212> TYPE: PRT
<213> ORGANISM: Populus trichocarpa

<400> SEQUENCE: 30

Ala Ala Gly Thr Thr Cys Ala Gly Ala Ala Gly Gly Gly Cys Thr
1               5                   10                  15

Thr Gly Thr Gly Gly Thr Cys Ala Cys Ala Gly Ala Gly Gly Ala
                20                  25                  30

Ala Gly Ala Thr Gly Ala Cys Ala Ala Gly Cys Thr Cys Ala Thr Gly
            35                  40                  45

Ala Ala Cys Thr Ala Cys Ala Thr Gly Cys Thr Ala Ala Cys Ala
    50                  55                  60

Ala Thr Gly Gly Ala Cys Ala Ala Gly Thr Thr Gly Cys Thr Gly
65                  70                  75                  80

Gly Ala Gly Thr Gly Ala Thr Gly Gly Cys Ala Ala Gly Gly
                85                  90                  95

Ala Ala Thr Gly Cys Thr Gly Gly Thr Thr Gly Cys Ala Gly Cys
            100                 105                 110

Gly Ala Thr Gly Cys Gly Gly Cys Ala Ala Gly Ala Gly Thr Thr Gly
            115                 120                 125

Cys Cys Gly Gly Cys Thr Thr Cys Gly Thr Thr Gly Gly Ala Thr Thr
    130                 135                 140

Ala Ala Thr Thr Ala Cys Thr Thr Gly Ala Gly Gly Cys Cys Thr Gly
145                 150                 155                 160

Ala Thr Cys Thr Cys Ala Ala Gly Ala Gly Ala Gly Gly Thr Gly Cys
            165                 170                 175
```

```
Ala Thr Thr Thr Thr Cys Ala Cys Cys Cys Ala Ala Gly Ala Ala
            180                 185                 190

Gly Ala Ala Gly Ala Gly Ala Thr Gly Ala Thr Cys Ala Thr Cys Cys
        195                 200                 205

Ala Thr Thr Thr Gly Cys Ala Thr Cys Cys Cys Thr Thr Cys Thr
        210                 215                 220

Cys Gly Gly Cys Ala Ala Thr Ala Gly Thr Gly Gly Thr Cys Thr
225                 230                 235                 240

Cys Ala Ala Thr Thr Gly Cys Gly Gly Cys Thr Cys Gly Cys Thr
                245                 250                 255

Thr Gly Cys Cys Ala Gly Gly Ala Ala Gly Ala Ala Cys Gly Gly Ala
        260                 265                 270

Cys Ala Ala Thr Gly Ala Ala Ala Thr Cys Ala Ala Gly Ala Ala Thr
        275                 280                 285

Thr Thr Thr Thr Gly Gly Ala Ala Thr Cys Ala Ala Cys Ala Ala
        290                 295                 300

Thr Ala Ala Ala Gly Ala Ala Gly Ala Gly Ala Thr Thr Ala Ala Ala
305                 310                 315                 320

Gly

<210> SEQ ID NO 31
<211> LENGTH: 107
<212> TYPE: PRT
<213> ORGANISM: Populus trichocarpa

<400> SEQUENCE: 31

Lys Phe Arg Lys Gly Leu Trp Ser Pro Glu Glu Asp Asp Lys Leu Met
1               5                   10                  15

Asn Tyr Met Leu Asn Asn Gly Gln Gly Cys Trp Ser Asp Val Ala Arg
            20                  25                  30

Asn Ala Gly Leu Gln Arg Cys Gly Lys Ser Cys Arg Leu Arg Trp Ile
        35                  40                  45

Asn Tyr Leu Arg Pro Asp Leu Lys Arg Gly Ala Phe Ser Pro Gln Glu
    50                  55                  60

Glu Glu Met Ile Ile His Leu His Ser Leu Leu Gly Asn Arg Trp Ser
65                  70                  75                  80

Gln Ile Ala Ala Arg Leu Pro Gly Arg Thr Asp Asn Glu Ile Lys Asn
                85                  90                  95

Phe Trp Asn Ser Thr Ile Lys Lys Arg Leu Lys
            100                 105

<210> SEQ ID NO 32
<211> LENGTH: 1266
<212> TYPE: DNA
<213> ORGANISM: Zea mays

<400> SEQUENCE: 32
gtacccagct ataggacggc aatgaggaaa ccggagtgcc cagcggcgaa cagcagcaat      60 gcggggggcgg cggccgcgaa gctgcggaag gggctgtggt cgccggagga ggacgagagg     120
ctggtggcgt acatgctgcg gagtggacag ggttcttgga cgatgtggc ccggaacgcc      180 gggttgcagc ggtgcggcaa gagctgccgc ctccggtgga tcaactacct ccggccggac     240
ctcaagcgcg gcgccttctc gccgcaggag gaggagctca tcgtcagcct ccacgccatc     300
ctgggaaaca ggtggtctca gattgctgcc cggttgccgg gcgcaccga caacgagatc      360
```

```
aagaacttct ggaactccac catcaagaag cggctcaaga acagctcggc agcttcgtca    420
ccagcagcta cggactgcgc gtcgccggag cctaataaca aggtcgccgc cgccggtagc    480
tgcccggatc tttccgtcct agatcatcag gacggtggcc accaccacgc aatgacgacg    540
acgactgcag gtttgtggat ggtggactca tcctcctctt gtacctcgtc gacctcgcca    600
atgcatcagt ttcagaggcc gacgacgacg atggcagcgg ccgtggccag cgggagctat    660
ggaggtctcg tccccttccc tgaccaggtc cgtggtgttg tggccgacac gggagggttc    720
tttcatggcc acgcggcgcc agcgttcaag caccaagttg ccgcattgca cggtggtggt    780
tattactacg gcagcgctcc tcgtcaccat ggaatgacga cgacgacgac gacggtggca    840
ttggaaggaa gcggtggatg cttcatatct ggcgaaggca tgcttggtgt gccccctctg    900
ctgttagagc ccatgtcagc agcgctagag caagaccaag gccagacctt gatggcatca    960
agtggtaaca acaaccctaa aaacaacagc agcagcaaca ctactgatac tacgactacc   1020
acgacactga gcaacaatga gagcaacgtc acagacacca ccaccaagga caacaccacc   1080
aacaccatca gccaagtgaa cagtggcagc aataatgtct actgggaggg ggcccgccag   1140
cagtacatga gcaggaatgt catgcatggg gagtgggacc tggaggagct gatgaaagat   1200
gtgtcatcct tgccttttct tgatttccaa gttgaatgat tgggagggcc gtgttgcatc   1260
tccagc                                                              1266
```

<210> SEQ ID NO 33
<211> LENGTH: 405
<212> TYPE: PRT
<213> ORGANISM: Zea mays

<400> SEQUENCE: 33

```
Met Arg Lys Pro Glu Cys Pro Ala Ala Asn Ser Ser Asn Ala Gly Ala
  1               5                  10                  15

Ala Ala Ala Lys Leu Arg Lys Gly Leu Trp Ser Pro Glu Glu Asp Glu
             20                  25                  30

Arg Leu Val Ala Tyr Met Leu Arg Ser Gly Gln Gly Ser Trp Ser Asp
         35                  40                  45

Val Ala Arg Asn Ala Gly Leu Gln Arg Cys Gly Lys Ser Cys Arg Leu
     50                  55                  60

Arg Trp Ile Asn Tyr Leu Arg Pro Asp Leu Lys Arg Gly Ala Phe Ser
 65                  70                  75                  80

Pro Gln Glu Glu Glu Leu Ile Val Ser Leu His Ala Ile Leu Gly Asn
                 85                  90                  95

Arg Trp Ser Gln Ile Ala Ala Arg Leu Pro Gly Arg Thr Asp Asn Glu
            100                 105                 110

Ile Lys Asn Phe Trp Asn Ser Thr Ile Lys Lys Arg Leu Lys Asn Ser
        115                 120                 125

Ser Ala Ala Ser Ser Pro Ala Ala Thr Asp Cys Ala Ser Pro Glu Pro
    130                 135                 140

Asn Asn Lys Val Ala Ala Ala Gly Ser Cys Pro Asp Leu Ser Val Leu
145                 150                 155                 160

Asp His Gln Asp Gly Gly His His Ala Met Thr Thr Thr Ala
                165                 170                 175

Gly Leu Trp Met Val Asp Ser Ser Ser Cys Thr Ser Ser Thr Ser
            180                 185                 190

Pro Met His Gln Phe Gln Arg Pro Thr Thr Met Ala Ala Ala Val
        195                 200                 205
```

```
Ala Ser Gly Ser Tyr Gly Gly Leu Val Pro Phe Pro Asp Gln Val Arg
    210                 215                 220
Gly Val Val Ala Asp Thr Gly Phe Phe His Gly His Ala Ala Pro
225                 230                 235                 240
Ala Phe Lys His Gln Val Ala Ala Leu His Gly Gly Tyr Tyr Tyr
                245                 250                 255
Gly Ser Ala Pro Arg His His Gly Met Thr Thr Thr Thr Thr Val
            260                 265                 270
Ala Leu Glu Gly Ser Gly Gly Cys Phe Ile Ser Gly Glu Gly Met Leu
        275                 280                 285
Gly Val Pro Pro Leu Leu Leu Glu Pro Met Ser Ala Ala Leu Glu Gln
    290                 295                 300
Asp Gln Gly Gln Thr Leu Met Ala Ser Ser Gly Asn Asn Asn Pro Lys
305                 310                 315                 320
Asn Asn Ser Ser Ser Asn Thr Thr Asp Thr Thr Thr Thr Thr Leu
                325                 330                 335
Ser Asn Asn Glu Ser Asn Val Thr Asp Thr Thr Lys Asp Asn Thr
            340                 345                 350
Thr Asn Thr Ile Ser Gln Val Asn Ser Gly Ser Asn Asn Val Tyr Trp
        355                 360                 365
Glu Gly Ala Arg Gln Gln Tyr Met Ser Arg Asn Val Met His Gly Glu
    370                 375                 380
Trp Asp Leu Glu Glu Leu Met Lys Asp Val Ser Ser Leu Pro Phe Leu
385                 390                 395                 400
Asp Phe Gln Val Glu
                405

<210> SEQ ID NO 34
<211> LENGTH: 1542
<212> TYPE: DNA
<213> ORGANISM: Hordeum vulgare

<400> SEQUENCE: 34
gtacttgcag ccttggagat cgacctggtc tctagatagg atagctagta cagtccataa    60
ctacatcttt gctaggagat cgggctgggc aatgaggaag cccgtggagt gcccggcgac   120
gaagtgcagt ggtggtgtgg cgccaggaaa cagcaatgtg gctgcagcgg cggccaagct   180
gcggaagggg ctgtggtcgc cggaggagga cgagaggctt gtggcgtaca tgctgcggag   240
cggtcagggg tcgtggagcg acgtggcacg caacgccggg ttacagcggt gcggcaagag   300
ctgccgcctc cggtggatca actacctccg tccggacctc aagcgcggcg ccttctcgcc   360
acatgaggag gacctcatcg tcaacctcca cgccatcctc ggcaacagat ggtctcagat   420
cgcagccagg ttaccggggc gcaccgacaa cgagatcaag aacttctgga actccaccat   480
caagaagcgg ctgaagatga actcggccgc ttcgtctccg gcgaccacgg aatgtgcgtc   540
accgcccgag cccaacctcg acggcggcag tgccagctgc ctcgacctca ccagccagga   600
ggacgggagc caccacgcaa tgaaaagcat gtggatggac tcatcctcct cctcctcttc   660
gtcttcgtcg atgcagcagg ggagccgacc gtcaacaatg ctccggcgg caaacagggg   720 ctacgggggc ctcctcctgc ccctcccgga ccaagtctgc ggcgtcgcac cttccaccca   780
cacgtcgttg ccgccgttct tccaagacca ttcatcgttt aagcaggttt ctcccttgcg   840
gaccggtggc tactaccctc acggaatggc aatggaagga gcaggtggct gcttcatggg   900
agaagaagct gtaggcggtg gaggcgaacg tagtgtcgtc ttcaacgtgc ccctctact    960
```

```
agagcccatg gcagtagcat tgcaagacca aaccttaatg gcatcaactg gtaacagcaa      1020
caataaccat cgaaacacta acagtactgc agagggcacc acactgagca gcaaaaatgg      1080
ctgcaacatc aatgacgaca acaccagtaa gaacaacatc aacagtgtgg tctcgtactg      1140
ggagcagcat ggtcagcagc agcacatgag caggaacgta gtcatggggg agtgggactt      1200
ggaggagctc atgaaagacg tgtcatgctt gcctttcctt gatttccaag ttgagtgatg      1260
acacgctgtt gggggccacc tcctacctgc gtgcctaaac tacatgcata tacgaatata      1320
catatataat taagtatata tacacatgca tacgttaaag gtagtctttt tttccttgac      1380
attatttaca tgatgtacgc aagatttctt cagcagccac tacttcactt ttgatactac      1440
atatatcttt gatgaattca ttcttgtata cagatactca tgcctatgca aataattcaa      1500
gcaaagttac ttgagttaat aaaaaaaaaa aaaaaaaaaa aa                         1542
```

<210> SEQ ID NO 35
<211> LENGTH: 388
<212> TYPE: PRT
<213> ORGANISM: Hordeum vulgare

<400> SEQUENCE: 35

```
Met Arg Lys Pro Val Glu Cys Pro Ala Thr Lys Cys Ser Gly Gly Val
 1               5                  10                  15

Ala Pro Gly Asn Ser Asn Val Ala Ala Ala Ala Lys Leu Arg Lys
            20                  25                  30

Gly Leu Trp Ser Pro Glu Glu Asp Glu Arg Leu Val Ala Tyr Met Leu
        35                  40                  45

Arg Ser Gly Gln Gly Ser Trp Ser Asp Val Ala Arg Asn Ala Gly Leu
    50                  55                  60

Gln Arg Cys Gly Lys Ser Cys Arg Leu Arg Trp Ile Asn Tyr Leu Arg
65                  70                  75                  80

Pro Asp Leu Lys Arg Gly Ala Phe Ser Pro His Glu Glu Asp Leu Ile
                85                  90                  95

Val Asn Leu His Ala Ile Leu Gly Asn Arg Trp Ser Gln Ile Ala Ala
            100                 105                 110

Arg Leu Pro Gly Arg Thr Asp Asn Glu Ile Lys Asn Phe Trp Asn Ser
        115                 120                 125

Thr Ile Lys Lys Arg Leu Lys Met Asn Ser Ala Ser Ser Pro Ala
    130                 135                 140

Thr Thr Glu Cys Ala Ser Pro Pro Glu Pro Asn Leu Asp Gly Gly Ser
145                 150                 155                 160

Ala Ser Cys Leu Asp Leu Thr Ser Gln Glu Asp Gly Ser His His Ala
                165                 170                 175

Met Lys Ser Met Trp Met Asp Ser Ser Ser Ser Ser Ser Ser Ser
            180                 185                 190

Ser Met Gln Gln Gly Ser Arg Pro Ser Thr Met Ala Pro Ala Ala Asn
        195                 200                 205

Arg Gly Tyr Gly Gly Leu Leu Leu Pro Leu Pro Asp Gln Val Cys Gly
    210                 215                 220

Val Ala Pro Ser Thr His Thr Ser Leu Pro Pro Phe Phe Gln Asp His
225                 230                 235                 240

Ser Ser Phe Lys Gln Val Ser Pro Leu Arg Thr Gly Tyr Tyr Pro
                245                 250                 255

His Gly Met Ala Met Glu Gly Ala Gly Gly Cys Phe Met Gly Glu Glu
            260                 265                 270
```

```
Ala Val Gly Gly Gly Glu Arg Ser Val Val Phe Asn Val Pro Pro
            275                 280                 285

Leu Leu Glu Pro Met Ala Val Ala Leu Gln Asp Gln Thr Leu Met Ala
290                 295                 300

Ser Thr Gly Asn Ser Asn Asn Asn His Arg Asn Thr Asn Ser Thr Ala
305                 310                 315                 320

Glu Gly Thr Thr Leu Ser Ser Lys Asn Gly Cys Asn Ile Asn Asp Asp
                325                 330                 335

Asn Thr Ser Lys Asn Asn Ile Asn Ser Val Val Ser Tyr Trp Glu Gln
                340                 345                 350

His Gly Gln Gln Gln His Met Ser Arg Asn Val Val Met Gly Glu Trp
                355                 360                 365

Asp Leu Glu Glu Leu Met Lys Asp Val Ser Cys Leu Pro Phe Leu Asp
370                 375                 380

Phe Gln Val Glu
385

<210> SEQ ID NO 36
<211> LENGTH: 533
<212> TYPE: PRT
<213> ORGANISM: Arabidopsis thaliana

<400> SEQUENCE: 36

Met Glu Leu Gly Asp Thr Thr Ser Val Ile Pro Asp Ser Phe Met Gly
1               5                   10                  15

Tyr Arg Asp Asp Ile Thr Met Gln Met Ser Met Val Leu Asp Gln Ile
                20                  25                  30

Arg Ala Pro Leu Ile Val Pro Ala Leu Arg Leu Gly Val Tyr Ile Cys
            35                  40                  45

Leu Thr Met Ser Val Met Leu Phe Val Glu Arg Val Tyr Met Gly Ile
50                  55                  60

Val Ile Ser Leu Val Lys Leu Phe Gly Arg Lys Pro Asp Lys Arg Phe
65                  70                  75                  80

Lys Tyr Glu Pro Ile Lys Asp Asp Ile Glu Leu Gly Asn Ser Ala Tyr
                85                  90                  95

Pro Met Val Leu Ile Gln Ile Pro Met Phe Asn Glu Arg Glu Val Tyr
            100                 105                 110

Gln Leu Ser Ile Gly Ala Ala Cys Gly Leu Ser Trp Pro Ser Asp Arg
            115                 120                 125

Ile Val Ile Gln Val Leu Asp Asp Ser Thr Asp Pro Thr Ile Lys Asp
130                 135                 140

Leu Val Glu Met Glu Cys Ser Arg Trp Ala Ser Lys Gly Val Asn Ile
145                 150                 155                 160

Lys Tyr Glu Ile Arg Asp Asn Arg Asn Gly Tyr Lys Ala Gly Ala Leu
                165                 170                 175

Lys Glu Gly Met Lys Lys Ser Tyr Val Lys Ser Cys Asp Tyr Val Ala
            180                 185                 190

Ile Phe Asp Ala Asp Phe Gln Pro Glu Ala Asp Phe Leu Trp Arg Thr
            195                 200                 205

Val Pro Tyr Leu Leu His Asn Pro Lys Leu Ala Leu Val Gln Ala Arg
        210                 215                 220

Trp Lys Phe Val Asn Ser Asp Glu Cys Leu Met Thr Arg Met Gln Glu
225                 230                 235                 240

Met Ser Leu Asp Tyr His Phe Thr Val Glu Gln Glu Val Gly Ser Ser
                245                 250                 255
```

Thr Tyr Ala Phe Phe Gly Phe Asn Gly Thr Ala Gly Ile Trp Arg Ile
            260                 265                 270

Ser Ala Leu Asn Glu Ala Gly Gly Trp Lys Asp Arg Thr Val Glu
        275                 280                 285

Asp Met Asp Leu Ala Val Arg Ala Ser Leu Lys Gly Trp Lys Phe Leu
290                 295                 300

Tyr Leu Gly Ser Leu Lys Val Lys Asn Glu Leu Pro Ser Thr Phe Lys
305                 310                 315                 320

Ala Tyr Arg Tyr Gln Gln His Arg Trp Ser Cys Gly Pro Ala Asn Leu
                325                 330                 335

Phe Arg Lys Met Ala Phe Glu Ile Met Thr Asn Lys Asn Val Thr Leu
            340                 345                 350

Trp Lys Lys Val His Val Ile Tyr Ser Phe Phe Val Val Arg Lys Leu
        355                 360                 365

Val Ala His Ile Val Thr Phe Ile Phe Tyr Cys Val Ile Leu Pro Ala
    370                 375                 380

Thr Val Leu Val Pro Glu Val Thr Val Pro Lys Trp Gly Ala Val Tyr
385                 390                 395                 400

Ile Pro Ser Val Ile Thr Leu Leu Asn Ala Val Gly Thr Pro Arg Ser
                405                 410                 415

Leu His Leu Met Val Phe Trp Ile Leu Phe Glu Asn Val Met Ser Leu
            420                 425                 430

His Arg Thr Lys Ala Thr Phe Ile Gly Leu Leu Glu Gly Gly Arg Val
        435                 440                 445

Asn Glu Trp Ile Val Thr Glu Lys Leu Gly Asp Val Lys Ala Lys Ser
    450                 455                 460

Ala Thr Lys Thr Ser Lys Lys Val Ile Arg Phe Arg Phe Gly Asp Arg
465                 470                 475                 480

Ile His Val Leu Glu Leu Gly Val Gly Met Tyr Leu Leu Phe Val Gly
                485                 490                 495

Cys Tyr Asp Ala Phe Phe Gly Lys Asn His Tyr Tyr Leu Tyr Leu Phe
            500                 505                 510

Ala Gln Ala Ile Ala Phe Phe Ile Ala Gly Phe Gly Gln Ile Gly Thr
        515                 520                 525

Ile Val Pro Asn His
    530

<210> SEQ ID NO 37
<211> LENGTH: 2299
<212> TYPE: DNA
<213> ORGANISM: Arabidopsis thaliana

<400> SEQUENCE: 37
ctcacacaca cacacacaca caacactgtg tcttctctcc ctctgtttct gttttagat      60 ctctcttctc tcttctttct ttccaaaaat catcttctcc ttctccacct ttcattatct    120
ttcttctctt accaaaaccc tttaaataca aaaaaaaact aaaacacata aaaaaaatat    180
tgaattctcc tttttcccga caatctgagt ttctcaggca gagaagacag agattttcac    240
cgtaagggca aaaacgaaa  aactctgtct ctctgtttct gtttcgtcct tccttggctt    300
tgatttctta caccaaaaga gacatcttta agaatctca  cattgttccc tattgcttgt    360
ctcacaagag aatccttgat ctagggttct tgcttccctc ccctgttttt ttctttaaat    420
tcctcctctg ttttcttttt gttctcgtcg gagtaagaag agatggagct aggagatacg    480

| | |
|---|---|
| acgtcggtga ttccagactc gttcatggga tacagagacg acataacaat gcaaatgtca | 540 |
| atggttttgg atcagatacg agctccattg attgttccag cccttaggct cggtgtttac | 600 |
| atctgtttga caatgtcggt gatgctcttt gttgaaaggg tttacatggg aattgttatc | 660 |
| tctcttgtga agctgtttgg tcgaaaacca gataaacgtt tcaaatatga accaatcaaa | 720 |
| gatgacatcg agcttggaaa ctctgcttac ccgatggttc ttattcaaat cccaatgttc | 780 |
| aacgaacgag aggtttatca actatctatt ggagctgctt gtggactctc atggccttct | 840 |
| gatcgaatcg ttattcaagt tcttgatgat tccactgatc caacgatcaa agatctagtg | 900 |
| gagatggagt gtagcaggtg ggcgagtaaa ggagtaaaca tcaagtatga gatcagagac | 960 |
| aacagaaatg gatacaaagc aggagctttg aaagaaggaa tgaagaagag ttatgtcaaa | 1020 |
| agctgcgatt acgttgcaat cttcgacgct gattttcaac ctgaagcgga ttttctatgg | 1080 |
| agaaccgtac cgtatctact ccataaccct aagcttgctc ttgttcaagc tcgctggaaa | 1140 |
| ttcgtaaatt cggatgaatg tttgatgaca aggatgcaag aaatgtcttt ggattatcat | 1200 |
| tttacggtgg aacaagaagt tggttcttct acttacgctt tcttcggatt caatggaact | 1260 |
| gcgggaatat ggagaatatc ggcattaaac gaagctggtg gttggaaaga tagaacgacc | 1320 |
| gtggaagata tggatttggc cgtgagagct agtctcaagg gttggaaatt cttgtacctc | 1380 |
| ggttctttga aggttaaaaa cgagttgcca agtacattca aggcttatag gtatcaacag | 1440 |
| cacaggtggt catgtggtcc agctaatctt ttcaggaaaa tggcattcga atcatgact | 1500 |
| aataagaacg tgactttgtg gaagaaagtt catgtgatat atagcttctt cgtggttaga | 1560 |
| aagctagtgg cacacattgt taccttcatc ttctactgtg tgatcttacc cgctacagtt | 1620 |
| cttgtaccgg aagttactgt tccgaaatgg ggagcggttt acattccttc agtcattact | 1680 |
| ctcctcaacg ccgttgggac accaaggtca ttgcatctta tggtcttttg gattctgttc | 1740 |
| gagaatgtga tgtctcttca cagaacaaaa gctaccttta tcggtttact cgaaggagga | 1800 |
| agagttaatg agtggattgt tacagagaag ctggggagatg ttaaggctaa atcagccacc | 1860 |
| aagacttcaa agaaggttat tcgtttttaga tttggagata gaattcatgt gttggaactc | 1920 |
| ggtgtaggaa tgtatctgtt atttgtggga tgttatgacg cgtttttttgg gaagaatcat | 1980 |
| tattatctat accttttcgc acaagcaatc gcgttcttca ttgcgggatt cgggcaaatt | 2040 |
| gggacaattg tgcctaacca ttgaagggaa aaaggagttt tcgagcgacg aattgctcga | 2100 |
| ggataagaag atgatttgtt ttctttcttt ttggattcgc tagctattta aattcttgtt | 2160 |
| ggtgtgaata gagagaattg atgataccat tgttacagaa atggtgtgtg tagtgtggaa | 2220 |
| gataaaggat acttatagta aagaagaaat atactttgaa ggttttttttc agattccttg | 2280 |
| aaggcaaatg attttttgac | 2299 |

<210> SEQ ID NO 38
<211> LENGTH: 1965
<212> TYPE: DNA
<213> ORGANISM: Arabidopsis thaliana

<400> SEQUENCE: 38

| | |
|---|---|
| atcaccaaga gaagcaacga aatgtttgga tcacatggat cctttttcctt taacccaaaa | 60 |
| ctaatgaccg tataagagtc aacttcagcc gttgagcagt cctatttttc cagctatgtg | 120 |
| tttcattttta tcatcgtttt aaaaatgatc gagatccatt tactttttta gtcaacatta | 180 |
| tttcctttaa attgcgattt gaatatatta acttaaaaga ttacgaagta aaaatgattg | 240 |
| atgaacgaag tcgaaacgtg cttcgaagtt tatgaaataa ttgacttttt gtatacttaa | 300 |

```
aaaaatttga ctttaaacaa acagaaaact ttttatttat ggtacttaat tagaatataa    360
caaactggac cgtcggtggg atttgaagca tcatggcaaa tgtgcgttgt tttaaaatgt    420
cttgaatatt cattttctcc tttggagagc ttctgttcga ttttgattgg tcgaaatata    480
tgacataaca tatttccact gaattgtaaa taatgtatta ggtatagtgg catataactc    540
aatgctaaaa acatatatca atttactgga tttcacaaaa ttgtaactca atgttactct    600
atatatggac cactgcatga tatccatgtc ttgtactaag gattcgatca ttcgattatc    660
ctcatcagag atgttcgcta tcttgtcaat agatgaggac aaacaatatg agacgatata    720
ttttcctcga gaaatgaacc attagaatca ctctactttt ggaattaacc ggttatgcaa    780
gtccatatga tttgtataaa tactgatata cataatgctc atctataatg catagttttt    840
tcattcagct ctaaaatatt ataagtaatg ttattgagcc tcgattgatt gattgacaaa    900
aaaaaaaaat gttattgagc cttcgattct tttttttgagc ctttaattgg tagttctata    960
ttagattaca tattatatca actgattaat cttcgatttc ttgagcttaa aaataaaata   1020
aaataataaa cgctggctag caaattgttt tgactgagat ggtcctatag ttttggacgc   1080
ctagacggct ataaactatc gagttttaac cttatacata attcatagtt gttacgaatt   1140
ataattaggc aattacacat ttgtattata ttatacatct atgtcacctc gagaagattg   1200
aagcattttt tttaacaatg acatttttat tttttaagaa aattatttta tcagaaactt   1260
aaaataacaa tttgttttgt atcttcgcct ggacgtcatt aatgtttgtg tcgttcaata   1320
atgtttggta gttatatata gaaagagcaa atttatggtt gattgatggt gcaaaaaaat   1380
tcatttctct atattctaga gaaataaaat aaaagaataa tggaatatta aatagagtct   1440
aaaacaatat acacaaggac agagccttta tatataaaga cattgatctc tctctgattt   1500
ctcacacaca cacacacaca caacactgtg tcttctctcc ctctgtttct gtttttagat   1560
ctctcttctc tcttcttttct ttccaaaaat catcttctcc ttctccacct ttcattatct   1620
ttcttctctt accaaaaccc tttaaataca aaaaaaaact aaaacacata aaaaaaatat   1680
tgaattctcc ttttttcccga caatctgagt ttctcaggca gagaagacag agattttcac   1740
cgtaagggca aaaaacgaaa aactctgtct ctctgtttct gtttcgtcct tccttggctt   1800
tgatttctta caccaaaaga gacatcttta aagaatctca cattgttccc tattgcttgt   1860
ctcacaagag aatccttgat ctagggttct tgcttccctc ccctgttttt ttctttaaat   1920
tcctcctctg ttttcttttt gttctcgtcg gagtaagaag agatg                   1965
```

<210> SEQ ID NO 39
<211> LENGTH: 33
<212> TYPE: DNA
<213> ORGANISM: Artificial Sequence
<220> FEATURE:
<223> OTHER INFORMATION: A synthetic oligonucleotide

<400> SEQUENCE: 39
caccatcacc aagagaagca acgaaatgtt tgg                                 33

<210> SEQ ID NO 40
<211> LENGTH: 35
<212> TYPE: DNA
<213> ORGANISM: Artificial Sequence
<220> FEATURE:
<223> OTHER INFORMATION: A synthetic oligonucleotide

<400> SEQUENCE: 40

```
ctcttcttac tccgacgaga acaaaaagaa aacag                          35

<210> SEQ ID NO 41
<211> LENGTH: 24
<212> TYPE: DNA
<213> ORGANISM: Artificial Sequence
<220> FEATURE:
<223> OTHER INFORMATION: A synthetic oligonucleotide

<400> SEQUENCE: 41
caccatggca aacgcagaga agac                                      24

<210> SEQ ID NO 42
<211> LENGTH: 18
<212> TYPE: DNA
<213> ORGANISM: Artificial Sequence
<220> FEATURE:
<223> OTHER INFORMATION: A synthetic oligonucleotide

<400> SEQUENCE: 42
tcatgtctta aaggacgc                                             18

<210> SEQ ID NO 43
<211> LENGTH: 31
<212> TYPE: DNA
<213> ORGANISM: Artificial Sequence
<220> FEATURE:
<223> OTHER INFORMATION: A synthetic oligonucleotide

<400> SEQUENCE: 43
caccatggag aagaggagct ctattaaaaa c                              31

<210> SEQ ID NO 44
<211> LENGTH: 19
<212> TYPE: DNA
<213> ORGANISM: Artificial Sequence
<220> FEATURE:
<223> OTHER INFORMATION: A synthetic oligonucleotide

<400> SEQUENCE: 44
ctatagaaac aaacaaaac                                            19

<210> SEQ ID NO 45
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 45
tcgtcattcg atgaatcttc c                                         21

<210> SEQ ID NO 46
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 46
agacacatac cattcaagcc c                                         21

<210> SEQ ID NO 47
<211> LENGTH: 24
<212> TYPE: DNA
<213> ORGANISM: Artificial Sequence
```

-continued

<220> FEATURE:
<223> OTHER INFORMATION: A synthetic oligonucleotide

<400> SEQUENCE: 47
tgattccatt atatagcact agcg                                              24

<210> SEQ ID NO 48
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 48
gatctccagt cttgaacgac g                                                 21

<210> SEQ ID NO 49
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 49
tgtgattcaa gggtggaagt c                                                 21

<210> SEQ ID NO 50
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 50
ttgttccgtt tggtggttta c                                                 21

<210> SEQ ID NO 51
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 51
aaatgaattt gtgttgtttg gg                                                22

<210> SEQ ID NO 52
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 52
cggtttaccc ttaccagctt c                                                 21